US011345964B2

(12) United States Patent
Albitar et al.

(10) Patent No.: US 11,345,964 B2
(45) Date of Patent: *May 31, 2022

(54) BCR-ABL TRUNCATION MUTATIONS

(71) Applicant: Quest Diagnostics Investments LLC, Secaucus, NJ (US)

(72) Inventors: Maher Albitar, Coto De Caza, CA (US); Wanlong Ma, Aliso Viejo, CA (US)

(73) Assignee: Quest Diagnostics Investments, LLC, Secaucus, NJ (US)

(*) Notice: Subject to any disclaimer, the term of this patent is extended or adjusted under 35 U.S.C. 154(b) by 142 days.

This patent is subject to a terminal disclaimer.

(21) Appl. No.: 16/153,094

(22) Filed: Oct. 5, 2018

(65) Prior Publication Data

US 2019/0112662 A1    Apr. 18, 2019

Related U.S. Application Data

(63) Continuation of application No. 15/342,321, filed on Nov. 3, 2016, now Pat. No. 10,093,980, which is a continuation of application No. 12/892,679, filed on Sep. 28, 2010, now Pat. No. 9,488,656.

(60) Provisional application No. 61/247,930, filed on Sep. 30, 2009.

(51) Int. Cl.
    C12Q 1/68       (2018.01)
    C12Q 1/6883     (2018.01)
    G01N 33/574     (2006.01)
    C12Q 1/6816     (2018.01)
    C12Q 1/686      (2018.01)

(52) U.S. Cl.
    CPC ......... *C12Q 1/6883* (2013.01); *C12Q 1/686* (2013.01); *C12Q 1/6816* (2013.01); *G01N 33/5748* (2013.01); *C12Q 2600/106* (2013.01); *C12Q 2600/118* (2013.01); *C12Q 2600/156* (2013.01); *C12Q 2600/158* (2013.01); *G01N 2800/52* (2013.01); *G01N 2800/54* (2013.01)

(58) Field of Classification Search
    None
    See application file for complete search history.

(56) References Cited

U.S. PATENT DOCUMENTS

| | | | |
|---|---|---|---|
| 4,798,885 A | 1/1989 | Mason et al. |
| 4,874,853 A | 10/1989 | Rossi |
| 4,946,778 A | 8/1990 | Ladner et al. |
| 4,952,496 A | 8/1990 | Studier et al. |
| 5,057,410 A | 10/1991 | Kawasaki et al. |
| 5,963,456 A | 10/1999 | Klein et al. |
| 6,001,230 A | 12/1999 | Burolla |
| 6,217,731 B1 | 4/2001 | Kane et al. |
| 6,329,179 B1 | 12/2001 | Kopreski |
| 6,582,908 B2 | 6/2003 | Fodor et al. |
| 6,773,882 B2 | 8/2004 | Hogan et al. |
| 6,849,400 B1 | 2/2005 | Harvey et al. |
| 6,916,634 B2 | 7/2005 | Kopreski |
| 6,939,671 B2 | 9/2005 | Kopreski |
| 7,521,213 B2 | 4/2009 | Hantash |
| 7,585,626 B1 | 9/2009 | Hantash et al. |
| 8,603,740 B2 | 12/2013 | Ma |
| 9,488,656 B2 | 11/2016 | Albitar et al. |
| 9,593,378 B2 | 3/2017 | Ma |
| 9,702,877 B2 | 7/2017 | Albitar |
| 9,957,574 B2 | 5/2018 | Ma |
| 10,093,980 B2 | 10/2018 | Albitar et al. |
| 2003/0148345 A1 | 8/2003 | Kopreski |
| 2003/0158105 A1 | 8/2003 | Sawyers et al. |
| 2004/0106140 A1 | 6/2004 | Thill |
| 2005/0176101 A1 | 8/2005 | West |
| 2005/0202519 A1 | 9/2005 | Barthe et al. |
| 2006/0269956 A1 | 11/2006 | Sawyers et al. |
| 2006/0292576 A1 | 12/2006 | Albitar et al. |
| 2007/0083334 A1 | 4/2007 | Mintz et al. |
| 2010/0113470 A1 | 5/2010 | Albitar |

FOREIGN PATENT DOCUMENTS

| | | |
|---|---|---|
| EP | 0 367 76 A2 | 9/1981 |
| EP | 0 117 060 A3 | 8/1984 |
| EP | 0 117 058 B1 | 9/1989 |
| GB | 2 211 504 A | 7/1989 |

(Continued)

OTHER PUBLICATIONS

Ma et al; Acta Haematol. vol. 121, pp. 27-31, Mar. 31, 2009.*
Gruber et al; Leukemia, vol. 20, pp. 2057-2060; 2006.*
Azam et al., Activity of dual SRC-ABL inhibitors highlights the role of BCR/ABL kinase dynamics in drug resistance, PNAS, 103(24):9244-9249 (2006).
Bradeen et al., Comparison of imatinib mesylate, dasatinib (BMS-354825), and nilotinib (AMN107) in an N-ethyl-N-nitrosourea (ENU)-based mutagenesis screen: high efficacy of drug combinations, Blood, 108:2332-2338 (2006).

(Continued)

Primary Examiner — Jehanne S Sitton
(74) Attorney, Agent, or Firm — Foley & Lardner LLP

(57) ABSTRACT

Truncation variants of BCR-ABL mRNA that produces BCR-ABL proteins with a truncated C-terminus and its role in resistance to treatment with kinase inhibitors is described. Vectors for expressing the truncated gene products are described as well as recombinant cells that express the truncated gene products from cDNA constructs. Also provided are methods compositions and kits for detecting the BCR-ABL truncation variants. Also provided are methods for determining the prognosis of a patient diagnosed as having myeloproliferative disease, and methods for predicting the likelihood for resistance to a treatment with tyrosine kinase inhibitor in a patient diagnosed as having myeloproliferative disease. Additionally, methods for screening BCR-ABL tyrosine kinase domain inhibitors which rely on the recombinant cells are also disclosed.

26 Claims, 5 Drawing Sheets

Specification includes a Sequence Listing.

(56) References Cited

FOREIGN PATENT DOCUMENTS

| | | |
|---|---|---|
| WO | WO-2009/029321 A2 | 3/2009 |
| WO | WO-2009/061890 | 5/2009 |

OTHER PUBLICATIONS

Branford et al., Detection of BCR-ABL mutations in patients with CML treated with imatinib is virtually always accompanied by clinical resistance, and mutations in the ATP phosphate-binding loop (P-loop) are associated with a poor prognosis, Blood, 102:276-283 (2003).
Branford et al., High frequency of point mutations clustered within the adenosine triphosphate-binding region of BCR/ABL in patients with chronic myeloid leukemia or Ph-positive acute lymphoblastic leukemia who develop imatinib (ST1571) resistance, Blood, 99: 3472-3475 (2002).
Burgess et al., Comparative analysis of two clinically active BCR-ABL kinase inhibitors reveals the role of conformation-specific binding in resistance, PNAS, 102(9):3395-3400 (2005).
Capdeville et al., Glivec (STI571, Imatinib), a Rationally Developed, Targeted Anticancer Drug, Nat. Rev. Drug Discov., 1:493 (2002).
Catovsk D., "Ph1 positive acute leukemia and chronic granulocytic leukemia: one or two disease." Br. J. Haematol 42: 493-498 (1979).
Chu et al., Dasatinib in Chronic Myelogenous Leukemia, N. Engl. J. Med., 355: 1062-1064(2006).
Clark S. S. et al., "Unique forms of the abl tryrosine kinase distinguish PH-positive CML from PH-positive ALL." Science 235:85-88, (1987).
Cross, et al., Competitive polymerase chain reaction to estimate the number of BCR-ABL transcripts in chronic myeloid leukemia patients after bone marrow transplantation. Blood 82: 1929-36, (1993).
Curvo et al., Leukemia Research, (2008), 32:508-510.
Deininger et al., The Tyrosine Kinase Inhibitor CGP57148B Selectively Inhibits the Growth of BCR-ABL-Positive Cells, Blood, 90: 3691-3698 (1997).
Deininger, et al., The development of imatinib as a therapeutic agent for chronic myeloid leukemia. Blood 105:2640-53 (2005).
Donato, N.J., BCR-ABL independence and LYN kinase overexpression in chronic myelogenous leukemia cells selected for resistance to STI571, Blood, 101: 690-698 (2003).
Eder et al., "Monitoring of BCR-ABL expression using Real-time RT-PCR in CML after bone marrow or peripheral blood stem cell transplantation." Leukemia 13:1383-1389 (1999).
Elefanty et al., bcr-abl, the hallmark of chronic myeloid leukaemia in man, induces multiple haemopoietic neoplasms in mice, Embo J., 9(4):1069-1078 (1990).
Emig et al. Accurate and rapid analysis of residual disease in patients with CML using specific fluorescent hybridization probes for real time quantitative RT-PCR. Leukemia, 13:1825-1832, 1999.
Ernst et al., Haematologica, (2008), 93(2):186-192.
Gorre et al., BCR-ABL point mutants isolated from patients with imatinib mesylate-resistant chronic myeloid leukemia remain sensitive to inhibitors of the BCR-ABL chaperone heat shock protein 90, Blood, 100: 3041-3044 (2002).
Gorre et al., Clinical Resistance to STI-571 Cancer Therapy Caused by BCR-ABL Gene Mutation or Amplification, Science, 293: 876-880 (2001).
Gruber et al., Leukemia, (2006), 20(11):2057-2060.
Gumireddy et al., A non-ATP-competitive inhibitor of BCR-ABL overrides imatinib resistance. PNAS, 102:1992, 2005.
Hariharan et al., cDNA sequence for human BCR, the gene that translocates to the abl oncogene in chronic myeloid leukemia. EMBO J. 6(1):115-119 (1987).
Hochhaus et al., Molecular and chromosomal mechanisms of resistance to imatinib (STI571) therapy, Leukemia. 16: 2190-2196 (2002).
Hochhaus, et al., Hematologic and Cytogenic Response Dynamics to Nilotinib (AMN107) Depend on the Type of BCR-ABL Mutations in Patients with Chronic Myelogenous Leukemia (CML) after Imatinib Failure, Blood, 108: 225a (2006).
Hughes et al., Monitoring CML patients responding to treatment with tyrosine kinase inhibitors: review and recommendations for harmonizing current methodology for detecting BCR-ABL transcripts and kinase domain mutations and for expressing results, Blood, 108: 28-37 (2006).
International Search Report dated Apr. 15, 2011 in application PCT/US2010/058987.
International Search Report dated Nov. 8, 2010 in application PCT/US2010/50539.
Kantarjian, et al., Quantitative polymerase chain reaction monitoring of BCR-ABL during therapy with imatinib mesylate (STI571; gieevec) in chronic-phase chronic myelogenous leukemia. Clin. Cancer Res. 9, 160-6 (2003).
Kawasaki et al., "Diagnosis of chronic myelogenous and acute lymphocytic by detection of leukemia-specific mRNA sequences in vitro." Proc. Natl. Acad. Sci USA 85: 5698-5702 (1988).
Klein et al., Oncogene, (2006), 25(7): 1118-1124.
Konopka J.B. et al., An alternative of the human c-abl protein in K562 leukemia cells unmasks associated Tyrosine kinase activity. Cell 37:1035-1042 (1984).
Kreuzer et al., "Applicability of an Absolute Quantitative Procedure to Monitor Intra-individual bcr/abl Transcript Kinetics In Clinical Samples from Chronic Myelogenous Leukemia Patients" Int. J. Cancer: 86:741-746 (2000).
Kuroda et al., Bim and Bad mediate imatinib-induced killing of BCR/ABL+ leukemic cells, and resistance due to their loss is overcome by a BH3 mimetic, Proc. Natl. Acad. Sci., U.S.A. 103:14097 (2006).
Kurzrock et al., The Molecular Genetics of Philadelphia Chromosome-Positive Leukemias, N. Engl. J. Med., 319: 990-998 (1988).
Laudadio et al., Consultations in Molecular Diagnostics, An Intron-Derived Insertion/Truncation Mutation in the BCR-ABL Kinase Domain in Chronic Myeloid Leukemia Patients Undergoing Kinase Inhibitor Therapy, J. Mol. Diag., 10(2): 177-180 (2008).
Lee et al., BCR-ABL alternative splicing as a common mechanism for imatinib resistance: evidence from molecular dynamics simulations, Mol. Cancer Ther. 7(12):3834-3841 (2008).
Lerma et al., Novel compounds with antiproliferative activity against imatinib-resistant cell lines, Mol. Cancer Ther., 6(2): 655-66 (2007).
Levinson et al., A Src-Like Inactive Conformation in the Abi Tyrosine Kinase Domain, PLoS Biol., 4: e144 (2006).
Lin et al., Proliferation and apoptosis in acute and chronic leukemias and myelodysplastic syndrome, Leuk Res., 26(6):551-9 (2002).
Lozzio, C.B. and Lozzio, B.B., Human chronic myelogenous leukemia cell-line with positive Phiiadeiphia chromosome, Blood, 45(3):321-334 (1975).
Ma et al., Three novel alternative splicing mutations in BCR-ABL 1 detected in CML patients with resistance to kinase inhibitors, presented at 51st ASH annual meeting and exposition (2009).
Ma et al., BCR-ABL Truncation due to Premature Translation Termination as a Mechanism of Resistance to Kinase Inhibitors, Acta Haematol., 121:27-31, Mar. 31, 2009.
Mahon, F.X., Blood, Selection and characterization of BCR-ABL positive cell lines with differential sensitivity to the tyrosine kinase inhibitor STI571: diverse mechanisms of resistance, 96:1070-1079 (2000).
Manley, P.W., Imatinib: a selective tyrosine kinase inhibitor, Eur. J. Cancer, 38: S19-S27 (2002).
Melo, J.V. & Chuah, C., Resistance to imatinib mesylate in chronic myeloid leukaemia, Cancer Lett., 249:121-132 (2007).
Mensink et al., Quantitation of minimal residual diseases in Philadelphia chromosome positive chronic myeloid leukemia patients using real time quantitative PCR. British J. Haematology 102:768-774 (1998)._ .
Moore, et al., Design of PCR primers that detect only mRNA in the presence of DNA. Nucleic Acids Res. 18:1921, 1991.
Nagar et al., Crystal Structures of the Kinase Domain of c-Abl in Complex with the Small Molecule Inhibitors PD173955 and Imatinib (STI-571), Cancer Res., 62: 4236-4243 (2002).

(56) References Cited

OTHER PUBLICATIONS

Nagar, B., Structural Basis for the Autoinhibition of C-Abl Tyrosine Kinase, Cell, 112: 859-871 (2003).
O'Hare et al., Combined Abl Inhibitor Therapy for Minimizing Drug Resistance in Chronic Myeloid Leukemia: Src/Abl Inhibitors Are Compatible with Imatinib, Clin. Cancer Res., 11(19):6987-6993 (2005).
O'Hare et al., Bcr-Abl kinase domain mutations, drug resistance, and the road to a cure for chronic myeloid leukemia, Blood, 110:2242-2249 (2007).
O'Hare, et al., AMN107: tightening the grip of imatinib. Cancer Cell 7:117-9 (2005).
Priest et al. "Philadelphia chromosome positive childhood acute lymphocytic leukemia." Blood 56: 15-22 (1980).
Ren et al., Abl protein-tyrosine kinase selects the Crk adapter as a substrate using SH3-binding sites, Genes Dev., 8(7): 783-95 (1994).
Rogers, et al., Relative increase in leukemia-specific DNA in peripheral blood plasma from patients with acute myeloid leukemia and myelodysplasia. Blood 103, 2799-2801 (2004).
Rowley, J.D., A New Consistent Chromosomal Abnormality in Chronic Myelogenous Leukaemia identified by Quinacrine Fluorescence and Giemsa Staining, Nature, 243: 290-3 (1973).
Shah et al., Sequential ABL kinase inhibitor therapy selects for compound drug-resistant BCR-ABL mutations with altered oncogenic potency, J. Clin. Invest., 117:2562-2569 (2007).
Shtivelman et al., "Alternative splicing of RNAs transcribed from the human abl gene and from the bcr-abl fused gene." Cell, 47:277-284 (1986).
Sooknanan, et al., Detection and direct sequence identification of BCR-ABL mRNA in PH+ chronic myeloid leukemia. Experimental Hematology 21:1719-1724, 1993.
Stroun, et al., Neoplastic characteristics of the DNA found in the plasma of cancer patients. Oncology 46:318-322, 1989.
Thomazy et al., Use of plasma RNA for real-time quantitative RT-PCR to monitor imatinib therapy in patients with chronic myeloid leukemia. Blood (ASH Annual Meeting Abstracts), 104: Abstract 1099, 2004.
US Office Action dated Jan. 8, 2009 in U.S. Appl. No. 11/301,272.
US Office Action dated May 11, 2011 in U.S. Appl. No. 12/472,319.
US Office Action dated Nov. 12, 2009 in U.S. Appl. No. 11/301,272.
US Office Action dated Dec. 6, 2010 in U.S. Appl. No. 12/472,319.
US Office Action dated Apr. 29, 2008 in U.S. Appl. No. 11/301,272.
Volpe et al, Cancer Res, (2007), 67(11):5300-5307.
Weisberg et al., AMN107 (nilotinib): a novel and selective inhibitor of BCR-ABL, Br. J. Cancer, 94:1765-1769 (2006).
Weisberg et al., Beneficial effects of combining nilotinib and imatinib in preclinical models of BCR-ABL + leukemias, Blood, 109:2112-2120 (2007).
Wertheim, et al., Blood, (2003), 102:2220-2228.
Alderborn et al., "Determination of Single-Nucleotide Polymorphisms by Real-time Pyrophosphate DNA Sequencing," Genome Res. (2000), 10:1249-1265.
Caceres et al, "Alternative splicing: multiple control mechanisms and involvement in human disease," Trends in Genetics 2002 18:186-193.
Chang et al., "Phenotypic expression in E. Coli of a DNA sequence coding for mouse dihydrofolate reductase," Nature (1978), 275:617-624.
Cote et al., "Generation of human monoclonal antibodies reactive with cellular antigens," Proc. Natl. Acad. Sci. (1983), 80:2026-2030.
deBoer et al., "The tac promoter: A functional hybrid derived from the trp and lac promoters," Proc. Natl. Acad. Sci. USA, vol. 80, pp. 21-25, Jan. 1983.
Drexler, H.G., The Leukemia-Lymphoma Cell Line Factsbook (2000), Academic Press.
Duffaud et al., "Expression and Secretion of Foreign Proteins in Escherichia coli," Meth. in Enzymology, 153:492-507, 1987.

GenBank Accession No. U07563.1, Human Proto-oncogene tyrosine-protein kinase (ABL) gene, exon 1a and exons 2-10, complete cds, printed Aug. 8, 2012. 33 pages.
Gething et al., "Cell-surface expression of influenza haemagglutinin from a cloned DNA copy of the RNA Gene," Nature (1981), 293:620-625.
Goeddel et al., "Direct expression in Escherichia coli of a DNA sequence coding for human growth hormone," Nature (1979), 281:544-548.
Gruber et al., "A novel Bcr-Abl splice isoform is associated with the L248V mutation in CML patients with acquired resistance to imatinib," Leukemia, Nov. 2006 vol. 20 No. 11, pp. 2057-2060.
H. Erlich, PCR Technology, Principles and Application for DNA Amplifications, 1989.
Heid, et al., "Real Time Quantitative PCR," Genome Res 6:986-994, 1996.
Hitzeman et al., "Isolation and Characterization of the Yeast 3-Phosphoglycerokinase Gene (PGK) by and Immunological Screening Technique," J. Biol. Chem, (1980), 255:12073-12080.
Holland, et al., "Isolation and Indentification of Yeast Messenger Ribonucleic Acids Coding for Enolase, Glyceraldehyde-3-Phosphate Dehydrogenase and Phosphoglycerate Kinase," Biochemistry (1978), 17:4900-4907.
Huse et al., "Generation of a Large Combinatorial Library of the Immunoglobulin Repertoire in Phage Lambda," Science, 1989; 246:1275-1281.
Kanehisa, M., "Use of Statistical Criteria for Screening Potential Homologies in Nucleic Acid Sequences," Polynucleotides Res. (1984), 12(1):203-213.
Kingsman et al., "Replication in Saccharomyces cerevisiae of Plasmid pBR313 Carrying DNA from the Yeast trpl Region," Gene (1979), 7:141-152; Elsevier/North-Holland Biomedical Press, Amsterdam—Printed in the Netherlands.
Kohler et al., "Continuous cultures of fused cells secreting antibody of predefined specificity," Nature (1975), 256:495-497.
Kozbor et al., "The Production of Monoclonal antibodies from human lymphocytes," Immunology Today (1983), 4(3):72-79.
Mantei et al., "Rabbit β-globin mRNA Production in mouse L cells transformed with cloned rabbit β-globin chromosomal DNA," Nature, Sep. 6, 1979, 281:40-46.
Marasco et al. (ed.), Intracellular Antibodies: Research and Disease Applications, Springer-Verlag New York, Inc. (1998) (ISBN: 3540641513).
McKenzie et al., "Mutants of the Formyltetrahydrofolate interconversion pathway of saccharomyces cerevisiae," Genetics (1977), 86:85-102.
Morrison et al., "Chimeric human antibody molecules: Mouse antigen-binding domains with human constant region domains," Proc. Natl. Acad. Sci. USA Nov. 1984, 81:6851-6855.
Mosmann, Tim, "Rapid Colorimetric Assay for Cellular Growth and Survival: Application to Proliferation and Cytotoxicity Assays," J. Immunol. Meth. 1983; 65:55-63.
Mulligan et al., "Synthesis of rabbit β-globin in cultured monkey kidney cells following infection with a SV40 β-globin recombinant genome," Nature, Jan. 11, 1979, vol. 277:108-114.
NCBI GenBank Accession No. AB069693, Homo Sapiens mRNA for bcr/abl e8a2 fusion protein, partial cds; http://www.ncbi.nlm.nih.gov/nuccore/AB069693.1?report=gbwithparts&log$=seqview, printed Aug. 8, 2012, 2 pages.
NCBI GenBank Accession No. AF113911, Homo sapiens BCR-ABL1 e1a2 chimeric protein (BCR/ABL fusion) mRNA, partial cds; http://www.ncbi.nlm.nih.gov/nuccore/AF113911.1?report=gbwithparts&log$=seqview, printed Aug. 8, 2012 2 pages.
NCBI GenBank Accession No. AF251769, Homo sapiens bcr/abl e1-a3 chimeric fusion protein (BCR/ABLe1-a3) mRNA, partial cds; http://www.ncbi.nlm.nih.gov/nuccore/AF251769.1?report=gbwithparts&log$=seqview, printed Aug. 8, 2012 1 page.
NCBI GenBank Accession No. AF487522, Homo sapiens BCRe18/ABLe3 fusion protein (BCR/ABL fusion) mRNA, partial cds; http://www.ncbi.nlm.nih.gov/nuccore/AF487522.1?report=gbwithparts&log$=seqview, printed Aug. 8, 2012 1 page.

(56) References Cited

OTHER PUBLICATIONS

NCBI GenBank Accession No. AY789120, *Homo sapiens* BCR/ABL fusion mRNA sequence; http://www.ncbi.nlm.nih.gov/nuccore/AY789120.1?report=gbwithparts&log$=seqview, printed Aug. 8, 2012 1 page.
NCBI GenBank Accession No. DQ898313, *Homo sapiens* isolate e1a4 BCR/ABL fusion protein (BCR/ABL fusion) mRNA, partial cds, alternatively spliced; http://www.ncbi.nlm.nih.gov/nuccore/dq898313, printed Aug. 8, 2012 2 pages.
NCBI GenBank Accession No. DQ898314, *Homo sapiens* isolate e13a4 BCR/ABL fusion protein (BCR/ABL fusion) mRNA, partial cds, alternatively spliced; http://www.ncbi.nlm.nih.gov/nuccore/DQ898314.1?report=gbwithparts&log$=seqview, printed Aug. 8, 2012 2 pages.
NCBI GenBank Accession No. DQ898315, *Homo sapiens* isolate e14a4 BCR/ABL fusion protein (BCR/ABL fusion) mRNA, partial cds alternatively spliced; http://www.ncbi.nlm.nih.gov/nuccore/DQ898315.1?report=gbwithparts&log$=seqview, printed Aug. 8, 2012 2 pages.
NCBI GenBank Accession No. DQ912588. *Homo sapiens* BCR/ABL fusion protein e1a5 (BCR/ABL fusion) mRNA, partial cds, alternatively spliced; http://www.ncbi.nlm.nih.gov/nuccore/DQ912588.1?report=gbwithparts&log$=seqview, printed Aug. 8, 2012 1 page.
NCBI GenBank Accession No. DQ912589, *Homo sapiens* BCR/ABL fusion protein e13a5 (BCR/ABL fusion) mRNA, partial cds, alternatively spliced; http://www.ncbi.nlm.nih.gov/nuccore/DQ912589.1?report=gbwithaparts&log$=seqview, printed Aug. 8, 2012 1 page.
NCBI GenBank Accession No. DQ912590, *Homo sapiens* BCR/ABL fusion protein e14a5 (BCR/ABL fusion) mRNA, partial cds, alternatively spliced; http://www.ncbi.nlm.nih.gov/nuccore/DQ912590.1?report=gbwithparts&log$=seqview, printed Aug. 8, 2012 1 page.
NCBI GenBank Accession No. EF158045, *Homo sapiens* BCR/ABL p210 fusion protein (BCR/ABL fusion) mRNA, partial cds; http://www.ncbi.nlm.nih.gov/nuccore/EF158045.1?report=gbwithparts&log$=seqview, printed Aug. 8, 2012 1 page.
NCBI GenBank Accession No. EF423615, *Homo sapiens* BCR/ABL fusion protein (BCR/ABL fusion) mRNA, partial cds; http://www.ncbi.nlm.nih.gov/nuccore/EF423615?report=gbwithparts&log$=seqview, printed Aug. 8, 2012 1 page.
NCBI GenBank Accession No. EU216058, *Homo sapiens* BCR/ABL fusion protein isoform X1 (BCR/ABL fusion) mRNA, complete cds; http://www.ncbi.nlm.nih.gov/nuccore/EU216058.1?report=gbwithparts&log$=seqview, printed Aug. 8, 2012 2 pages.
NCBI GenBank Accession No. EU216059, *Homo sapiens* BCR/ABL fusion protein isoform X2 (BCR/ABL fusion) mRNA, complete cds; http://www.ncbi.nlm.nih.gov/nuccore/EU216059.1?report=gbwithparts&log$=seqview, printed Aug. 8, 2012 2 pages.
NCBI GenBank Accession No. EU216060, *Homo sapiens* BCR/ABL fusion protein isoform X3 (BCR/ABL fusion) mRNA, complete cds; http://www.ncbi.nlm.nih.gov/nuccore/Eu216060, printed Aug. 8, 2012 3 pages.
NCBI GenBank Accession No. EU216061, *Homo sapiens* BCR/ABL fusion protein isoform X4 (BCR/ABL fusion) mRNA, complete cds; http://www.ncbi.nlm.nih.gov/nuccore/Eu216061, printed Aug. 8, 2012 2 pages.
NCBI GenBank Accession No. EU216062, *Homo sapiens* BCR/ABL fusion protein isoform X5 (BCR/ABL fusion) mRNA, complete cds; http://www.ncbi.nlm.nih.gov/nuccore/Eu216062, printed Aug. 8, 2012 2 pages.
NCBI GenBank Accession No. EU216063, *Homo sapiens* BCR/ABL fusion protein isoform X6 (BCR/ABL fusion) mRNA, complete cds; http://www.ncbi.nlm.nih.gov/nuccore/Eu216063, printed Aug. 8, 2012 2 pages.
NCBI GenBank Accession No. EU216064, *Homo sapiens* BCR/ABL fusion protein isoform X7(BCR/ABL fusion) mRNA, complete cds; http://www.ncbi.nlm.nih.gov/nuccore/Eu216064, printed Aug. 8, 2012 2 pages.
NCBI GenBank Accession No. EU216065, *Homo sapiens* BCR/ABL fusion protein isoform X8 (BCR/ABL fusion) mRNA, complete cds; http://www.ncbi.nlm.nih.gov/nuccore/Eu216065, printed Aug. 8, 2012 2 pages.
NCBI GenBank Accession No. EU216066. *Homo sapiens* BCR/ABL fusion protein isoform X9 (BCR/ABL fusion) mRNA, complete cds; http://www.ncbi.nlm.nih.gov/nuccore/Eu216066, printed Aug. 8, 2012 3 pages.
NCBI GenBank Accession No. EU216067, *Homo sapiens* BCR/ABL fusion protein isoform Y1 (BCR/ABL fusion) mRNA, complete cds; http://www.ncbi.nlm.nih.gov/nuccore/Eu216067, printed Aug. 8, 2012 2 pages.
NCBI GenBank Accession No. EU216068, *Homo sapiens* BCR/ABL fusion protein isoform Y2 (BCR/ABL fusion) mRNA, complete cds; http://www.ncbi.nlm.nih.gov/nuccore/Eu216068, printed Aug. 8, 2012 2 pages.
NCBI GenBank Accession No. EU216069, *Homo sapiens* BCR/ABL fusion protein isoform Y3 (bcr/ABL fusion) mRNA, complete cds; http://www.ncbi.nlm.nih.gov/nuccore/Eu216069, printed Aug. 8, 2012 2 pages.
NCBI GenBank Accession No. EU216070, *Homo sapiens* BCR/ABL fusion protein isoform Y4 (BCR/ABL fusion) mRNA, complete cds; http://www.ncbi.nlm.nih.gov/nuccore/Eu216070; printed Aug. 8, 2012 2 pages .
NCBI GenBank Accession No. EU216071, *Homo sapiens* BCR/ABL fusion protein isoform Y5 (BCR/ABL fusion) mRNA, complete cds; http://www.ncbi.nlm.nih.gov/nuccore/Eu216071, printed Aug. 8, 2012 3 pages.
NCBI GenBank Accession No. EU236680, *Homo sapiens* BCR/ABL b3a3 fusion protein (BCR/ABL fusion) mRNA, partial cds; htt://www.ncbi.nlm.nih.gov/nuccore/eu236680, printed Aug. 8, 2012 2 paqes.
NCBI GenBank Accession No. M14752, Human c-abl gene, complete cds; http://www.ncbi.nlm.nih.gov/nuccore/m14752, printed Aug. 8, 2012 2 pages.
NCBI GenBank Accession No. M15025, Human BCR/ABL mRNA (product of translocation t(22q11;9q34)), 5'end; www.ncbi.nlm.nih.gov/nuccore/m15025, printed Aug. 8, 2012, 2 pages.
NCBI GenBank Accession No. M17541, Human bcr/abl fusion protein (product of translocation t(22q11; 9q34)), exons 1 and 2; http://www.ncbi.nlm.nih.gov/nuccore/m17541, printed Aug. 8, 2012 1 page.
NCBI GenBank Accession No. M17542, Human bcr/abl protein gene (product of tranlocation t(22q11; 9q34)), exons 1 and 2, http://www.ncbi.nlm.nih.gov/nuccore/m17542, printed Aug. 8, 2012 1 page.
NCBI GenBank Accession No. M30829, Human bcr/abl fusion protein mRNA, partial cds, clone K28; http://www.ncbi.nlm.nih.gov/nuccore/m30829, printed Aug. 8, 2012 1 page.
NCBI GenBank Accession No. M30832, Human bcr/abl fusion protein, partial cds, clone E3; http://www.ncbi.nlm.nih.gov/nuccore/m30832, printed Aug. 8, 2012, 1 page.
NCBI GenBank Accession No. S72478, Bcr . . . Abl {b3/a3 junction, translocation breakpoint} [human, Japanese CML patient 1 and ALL patient 2, peripheral blood, monoculear cells, mRNA Mutant, 3 genes, 140 nt]; http://www.ncbi.nlm.nih.gov/nuccore/s72478, printed Aug. 8, 2012 1 page.
NCBI GenBank Accession No. S72479, BCR . . . ABL {e1/a3 junction, translocation breakpoint} [human, Japanese ALL patient 3, bone marow, mononuclear cells, mRNA Mutant, 3 genes, 131 nt]. http://www.ncbi.nlm.nih.gov/nuccore/s72479, printed Aug. 8, 2012 1 page.
NCBI GenBank Accession Nos. EU216072, Humo sapiens BCR/ABL fusion protein isoform Y6 (BCR/ABL fusion) mRNA, complete cds; http://www.ncbi.nlm.nih.gov/nuccore/eu216072, printed Aug. 8, 2012 2 pages.
NCBI Protein Database Accession No. AAA35594, BCR-ABL protein, partial (*Homo sapiens*); http:www.ncbi.nlm.nih.gov/protein/AAA35594.1?report=gpwithparts&log$=seqview, printed Aug. 8, 2012 1 page.
NCBI Protein Database Accession No. ABX82702, BCR/ABL fusion protein isoform X3 [*Homo Sapiens*]; http://www.ncbi.nlm.nih.gov/protein/abx82702, printed Aug. 8, 2012, 2 pages.

(56) References Cited

OTHER PUBLICATIONS

NCBI Protein Database Accession No. ABX82708, BCR/ABL fusion protein isoform X9 [*Homo sapiens*]; http://www.ncbi.nlm.nih.gov/protein/abx82708, printed Aug. 8, 2012, 2 pages.

Neuberger et al., "Recombinant antibodies possessing novel effector functions," Nature, Dec. 13, 1984, 312:604-608.

Okayama, "High-Efficiency Cloning of Full-Lenghth DNA," Mol. Cell. Biol. Feb. 1982, vol. 2:161-170.

Phillips G.J., "Green fluorescent protein—a bright idea for the study of bacterial protein localization," FEMS Microbiol. Lett. 2001; 204(1):9-18.

Sambrook, et al., Molecular Cloning: A Laboratory Manual (1989), Second Edition, Cold Spring Harbor Press, Plainview, NY.

Sanger et al., "DNA sequencing with chain-terminating inhibitors," PNAS USA, Dec. 1977, 74(12):5463-5467.

Stinchcomb et al., "Isolation and Characterisation of a yeast chromosomal replicator," Nature, Nov. 1979, 282:39-43.

Stoilov et al., "Defects in Pre-mRNA Processing as Causes of and Predisposition to Diseases," DNA and Cell Biology, 2002 21 (11):803-818.

Sun et al., "Modulation of the Cytotoxicity of 3'-Azido-3'-deoxythymidine and Methotrexate after Transduction of Folate Receptor cDNA into Human Cervical Carcinoma: Identification of a Correlation between Folate Receptor Expression and Thymidine Kinase Activity," Cancer Res. Feb. 15, 1999; 59:940-946.

Takeda et al., "Construction of chimaeric processed immunoglobulin genes containing mouse variable and human constant region sequences," Nature, Apr. 4, 1985, 314:452-454.

Tyagi et al., "Multicolor molecular beacons for allele discrimination," Nature Biotechnology, Jan. 1998, 16:49-53.

Urlaub et al., "Isolation of Chinese hamster cell mutants deficient in dihydrofolate reductase activity," Proc. Natl Acad. Sci. USA, Jul. 1980, pp. 4216-4220, vol. 77, No. 7.

Wong et al., "Human GM-CSF: Molecular Cloning of the Complementary DNA and Purification of the Natural and Recombinant Proteins," Science, 1985; 228:810-815.

Wong et al., "The BCR-ABL Story: Bench to Bedside and back," Annu. Rev. Immunol. 2004; 22:247-306.

Wu et al., "Alternatively Spliced Genes," Encyclopedia of Molecular and Cell Biology and Molecular Medicine, vol. 1, 2nd ed., 125-177 (2004).

Zimmermann et al., "A simplified protocol for fast plasmid DNA sequencing," Nucleic Acids Res. vol. 18, No. 4, p. 1067, Submitted Jan. 19, 1990, © 1990 Oxford University Press.

Evans et al., Pharmacogenomics: Translating Functional Genomics into Rational Therapeutics Science vol. 286:487-491 (1999).

Quintas-Cardama et al., Phase I/II study of subcutaneous homoharringtonine in patients with chronic myeloid leukemia who have failed prior therapy, Cancer, 109(2):248-255 (2006).

Tokarski et al., The structure of dasatinib (BMS-354825) bound to activated ABL kinase domain elucidates its inhibitory activity against imatinib-resistant ABL mutants, Cancer Research, 66(11):5790-5797 (2006).

US Office Action dated Mar. 14, 2012 in U.S. Appl. No. 12/472,319.

US Office Action dated Jul. 6, 2011 in U.S. Appl. No. 11/301,272.

Juppner, "Functional Properties of the PTH/PTHrP Receptor", Bone, Aug. 1995, vol. 17, No. 2 Supplement, pp. 39S-42S.

Mummidi, et al. "Evolution of Human and Non-human Primate CC Chemokine Receptor 5 Gene and mRNA", The Journal of Biological Chemistry, Jun. 2000, vol. 275, No. 25, pp. 18945-18961.

Office Action issued in U.S. Appl. No. 12/472,319 dated Aug. 19, 2014.

Office Action issued in U.S. Appl. No. 13/512,945 dated Aug. 28, 2014.

Office Action issued in U.S. Appl. No. 12/892,679 dated Nov. 27, 2012.

Office Action issued in U.S. Appl. No. 12/892,679 dated Aug. 5, 2013.

Office Action issued in U.S. Appl. No. 12/892,679 dated Jan. 28, 2014.

Office Action issued in U.S. Appl. No. 12/892,679 dated Sep. 30, 2014.

Office Action issued in U.S. Appl. No. 12/892,679 dated Jun. 19, 2015.

Notice of Allowance issued in U.S. Appl. No. 12/892,679 dated Jun. 21, 2016.

Bolufer et al., "Rapid quantitative detection of BCR-ABL transcripts in chronic myeloid leukemia patients by real-time reverse transcriptase polymerase-chain reaction using fluorescently labeled probes," Haematologica, 2000, 85:1248-1254.

Bubnoff et al., "Resistance of Philadelphia-chromosome positive leukemia towards the kinase inhibitory imatinib (STI571, Glivec); a targeted oncoprotein strikes back", Leukemia, vol. 17, 2003, pp. 829-838.

Dhingra et al., "Hybridization Protection Assay: A Rapid, Sensitive, and Specific Method for Detection of Philadelphia Chromosome-Positive Leukemias," Blood, Jan. 15, 1991, 77(2):238-242.

Iqbal et al., "Two different point mutations in ABL gene ATP-binding domain conferring Primary Imatinib resistance in a Chronic Myeloid Leukemia (CML) patient: A case report" Biol. Proced. Online, vol. 6, No. 1, 2004, pp. 144-148.

US Office Action in U.S. Appl. No. 15/429,640 dated Jul. 27, 2017.

US Final Office Action in U.S. Appl. No. 12/472,319 dated Dec. 20, 2016.

US Notice of Allowance on U.S. Appl. No. 12/472,319 dated Mar. 9, 2017.

US Notice of Allowance on U.S. Appl. No. 14/076,324 dated Oct. 31, 2016.

US Notice of Allowance on U.S. Appl. No. 15/429,640 dated Dec. 27, 2017.

US Office Action on U.S. Appl. No. 12/472,319 dated Jul. 11, 2016.

US Final Office Action on U.S. Appl. No. 14/076,324 dated Aug. 11, 2016.

US Office Action on U.S. Appl. No. 14/954,203 dated Dec. 28, 2016.

US Final Office Action on U.S. Appl. No. 14/954,203 dated May 22, 2017.

"Chemotherapy Drugs"; STI-571, 2005[online][retrieved on May 19, 2010], Available on the Internet: <URL: http://www.chemocare.com/bio/sti.asp >.

ABI prism user bulletin #5 (1998).

Abravaya, et al., "Detection of point mutations with a modified ligase chain reaction (Gap-LCR)"; Nucleic Acids Research 23:675-682, 1995.

Albitar, M. et al., "Free circulating soluble CD52 as a tumor marker in chronic lymphocytic leukemia and its implication in therapy with anti-CD52 antibodies"; Cancer 101, 999-1008 (2004).

Aldea et al., "Rapid detection of herpes simplex virus DNA in genital ulcers by real-time PCR using SYSBR green 1 dye as the detection signal"; J. Clin. Microbiol. 40(3):1060-1062 (2002).

Antony et al., "A Molecular Beacon Strategy for the Thermodynamic Characterization of Triplex DNA: Triplex formation at the promoter Region of Cyclin D1"; Biochemistry, 40:9387-9395 (2001).

Bao et al., "SNP identification in unamplified human genomic DNA with gold nanoparticle probes"; Nucleic Acids Research, 33:e15 (2005).

Boom, et al., "Rapid and simple method for purification of nucleic acids"; J Clin Micro 28:495-503, 1990.

Boom, et al., "Rapid purification of hepatitis B virus DNA from serum"; J Clin Micro 29:1804-1811, 1991.

Branford et al., "Real-time quantitative PCR analysis can be used as a primary screen to identify patients with CML treated with imatinib who have BCR-ABL kinase domain mutations"; Blood, vol. 104, No. 9, Nov. 1, 2004 (Nov. 1, 2004), pp. 2926-2932.

Buchman, et al., A., "Selective RNA amplification: A novel method using dUMP-containing primers and uracil DNA glycosylase"; PCR Methods Applic 3:28-31, 1993.

Buck et al., Design Strategies and Performance of Custom DNA Sequencing Primers, BioTechniques, 1999, 27:528-536.

Cheung, et al., "Rapid and sensitive method for detection of hepatitis C virus RNA by using silica particles"; J Clin Micro 32:2593-2597, 1994.

(56) References Cited

OTHER PUBLICATIONS

Chirgwin, et al., "Isolation of biologically active ribonucleic acid from sources enriched in ribonuclease"; Biochemistry 18:5294-5299, 1979.
Chomczynski and Mackey, "Modification of the TRI reagent$2122 procedure for isolation of RNA from polysaccharide- and proteoglycan-rich sources"; BioTechniques 19:942-945, 1995.
Chomczynski and Mackey, "Substitution of choroform by bromo-chloropropane in the single-step method of RNA isolation"; Analytical Biochemistry 225:163-164, 1995.
Chomczynski and Sacchi, "Single-step method of RNA isolation by acid guanidinium thiocyanate-phenol-chloroform extraction"; Analytical Biochemistry 162:156-159, 1987.
Chomczynski, "A reagent for the single-step simultaneous isolation of RNA, DNA and proteins from cell and tissue samples"; Biotech 15:532-537, 1993.
Cole et al., "The EBV-Hybridoma Technique and Its Application to Human Lung Cancer, Monoclonal Antibodies and Cancer Therapy"; Alan R. Liss, Inc., pp. 77-96 (1985).
Ercolani et al., "Isolation and complete sequence of a functional human Glyceraldehyde 3 phosphate dehydrogenase gene"; J. Biol. Chem. 263(30):15335-15341 (1988).
Final Office Action on U.S. Appl. No. 15/952,436 dated Mar. 18, 2020.
Fiser, A. & Sali, A., "Modeller: Generation and Refinement of Homology-Based Protein Structure Models"; Methods Enzymol., 374: 461-491 (2003).
Fournie, et al., "Recovery of nanogram quantities of DNA from plasma and quantitative measurement using labeling by nick translation"; Analytical Biochemistry 158:250-256, 1986.
Galea-Lauri, "Immunological weapons against acute myeloid leukaemia"; Immunology (2002); 107:20-27.
GenBank Record G03845, human STS WI-3568, sequence tagged site, Oct. 19, 1995, 1 page.
Gibson et al., "A novel method for real-time quantitative RT-PCR"; Genomic Res. 6: 995-1001 (1996).
Guilhot, F., and Roy, L., "Chronic myeloid leukemia" in Textbook of Malignant Hematology Ch. 41, pp. 696-734, 2nd Ed. (Degos et al., eds), Taylor and Francis Medical Books, 2005.
Hamaguchi et al., "Aptamer Beacons for the Direct Detection of Proteins"; Analytical Biochemistry 294:126-131 (2001).
Hay et al., "Bone Morphogenetic Protein Receptor IB Signaling Mediates Apoptosis Independently of Differentiation in Osteoblastic Cells"; J. Biol. Chem., 279: 1650-1658 (2004).
Hoelzer, D. and Gokbuget, N., "Acute lymphoblastic leukemia in adults" in Textbook of Malignant Hematology Ch. 32, pp. 500-520, 2nd Ed. (Degos et al., eds), Taylor and Francis Medical Books, 2005.
Imai, et al., "Detection of HIV-1 RNA in heparinized plasma of HIV-1 seropositive individuals"; J Virol Methods 36:181-184, 1992.
International Search Report dated Jun. 7, 2010 in application PCT/US2009/061539.
Kaboev et al., "PCR hot start using primers with the structure of molecular beacons (hairpin-like structure)"; Nucleic Acids Research 28(21):e94 (2000).
Kampke et al., "Efficient primer design algorithms"; Bioinformatics, 17:214-225, (2000).
Karet, et al., "Quantification of mRNA in human tissue using fluorescent nested reverse-transcriptase polymerase chain reaction"; Analytical Biochemistry 220:384-390, 1994.
Kaspers, GJL and Ravindranath, Y., "Acute myeloid leukemia in children and adolescents" in Textbook of Malignant Hematology Ch. 37, pp. 617-632, 2nd Ed. (Degos et al., eds), Taylor and Francis Medical Books, 2005.
Kievits et al., "NASBA$2122 isothermal enzymatic in vitro nucleic acid amplification optimized for the diagnosis of HIV-1 infection"; J Virological Methods 35:273-286, 1991.
Komarova et al., "Combination of Two but Not Three Current Targeted Drugs Can Improve Therapy of Chronic Myeloid Leukemia"; PLoS One, 4(2) e4423:1-5 (2009).

Larkin et al., "Clustal Wand Clustal X version 2.0, Bioinformatics"; 23:2947-2948 (2007).
Lee et al., "Age-related telomere length dynamics in peripheral blood mononuclear cells of healthy cynomolgus monkeys measured by Flow FISH"; Immunology, 105:458-465, (2002).
Lesniak et al., "Calcyclin (S100A6) expression is stimulated by agents evoking oxidative stress via the antioxidant response element," Bioehimica et Biophysica Acta, 2005, 1744:29-37.
Lowe et al., A computer program for selection of oligonucleotide primers for polymerase chain reactions, Nucleic Acids Research, 1990, 18(7):1757-1761.
NEB Catalog, New England Biolabs, 1996/1997 (1996), p. 111.
Non-Final Office Action in U.S. Appl. No. 13/512,945 dated Jan. 16, 2014.
Non-Final Office Action on U.S. Appl. No. 15/952,436 dated Oct. 4, 2019.
Notice of Allowance in U.S. Appl. No. 15/643,937 dated Apr. 10, 2020.
Notice of Allowance in U.S. Appl. No. 12/981,416 dated Aug. 9, 2013.
Poddar, S.K. and Le, C.T., "Bordetella pertussis detection by spectrofluorometry using polymerase chain reaction (PCR) and a molecular beacon probe"; Molecular and Cellular Probes 15:161-167 (2001).
Rao et al., "Genotyping single nucleotide polymorphisms directly from genomic DNA by invasive cleavage reaction on microspheres"; Nucleic Acids Research, 31(11):e66 (2003).
Rashtchian, "Amplification of RNA"; PCR Methods Applic 4:S83-S91, 1994.
Robertson and Walsh-Weller, "An Introduction to PCR Primer Design and Optimization of Amplification Reactions"; Methods of Mol. Biol., 98:121-126.
Rothstein et al., "Chronic inhibition of superoxide dismutase produces apoptotic death of spinal neurons," PNAS USA, May 1994, 91:4155-4159.
Smirnov, I. and Shafer, R.H., "Effect of Loop Sequence and Size on DNA Aptamer Stability"; Biochemistry 39:1462-1468 (2000).
The Leukemia & Lymphoma Society, Fighting Blood Cancers, Facts 2009-2010, pp. 1-25.
Urdea et al., "Direct and quantitative detection of HIV-1 RNA in human plasma with a branched DNA signal amplification assay"; AIDS 7 (suppl 2):S11-S14, 1993.
Urdea, et al., "Branched DNA amplification multimers for the sensitive, direct detection of human hepatitis viruses"; Nucleic Acids Research Symposium Series 24:197-200, 1991.
US Notice of Allowance (Corrected) in U.S. Appl. No. 15/429,640 dated Jan. 24, 2018.
US Notice of Allowance in U.S. Appl. No. 15/342,321 dated May 22, 2018.
US Office Action dated Jan. 11, 2008 in U.S. Appl. No. 11/301,272.
US Office Action in U.S. Appl. No. 14/076,324 dated Apr. 18, 2016.
US Office Action in U.S. Appl. No. 15/342,321 dated Oct. 4, 2017.
US Office Action in U.S. Appl. No. 15/643,937 dated Feb. 6, 2019.
US Office Action in U.S. Appl. No. 11/301,272 dated Jun. 2, 2015.
US Office Action in U.S. Appl. No. 12/472,319 dated Jun. 3, 2015.
US Office Action dated Jun. 16, 2011 in U.S. Appl. No. 11/301,272.
Vandamme, et al., "Detection of HIV-1 RNA in plasma and serum samples using the NASBA amplification system compared to RNA-PCR"; J Virological Methods 52:121-132, 1995.
Wang et al., "Primers are Decisive for Sensitivity of PCR"; Biotechniques, 17:82-85 (1994).
Wang, et al., "Quantitation of mRNA by the polymerase chain reaction"; Proc Natl Acad Sci USA 86:9717-9721, 1989.
Wiedmann et al., "Ligase Chain Reaction (LCR) Overview and Applications"; PCR Methods Appl. 3:S51-S64, (1994).
Yamamoto, R. and Kumar, P.K.R., "Molecular beacon aptamer fluoresces in the presence of Tat protein of HIV-1"; Genes to Cells, 5:389-396 (2000).
Zhang et al., "Reproducible and inexpensive probe preparation for oligonucleotide arrays"; Nucleic Acids Research, 29(13):e66 (2001).
Dieffenbach et al., "General concepts for PCR primer design," PCR Methods Appl., 1993, 3:s30-s37.

(56) References Cited

OTHER PUBLICATIONS

Roux, K.H., "Optimization and troubleshooting in PCR," PCR Methods Appl., 1995, 4:s185-s194.

* cited by examiner

FIG. 2A: Del 2595-2779

FIG. 2B: Del 2596-2597

FIG. 2C: 2417insCAGG
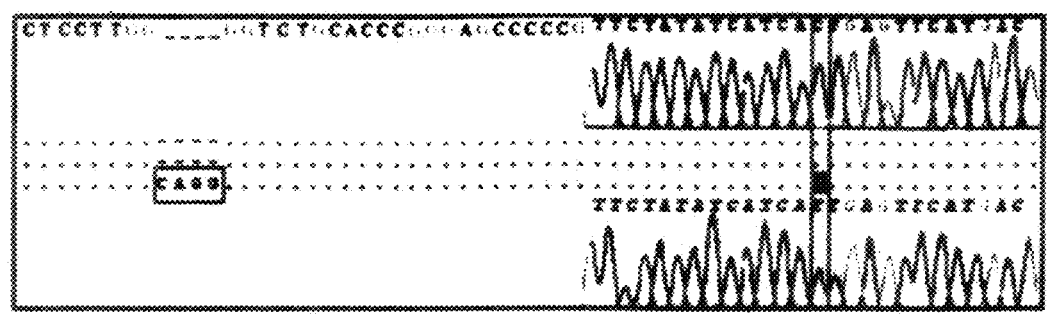
FIG. 2D: C2506T
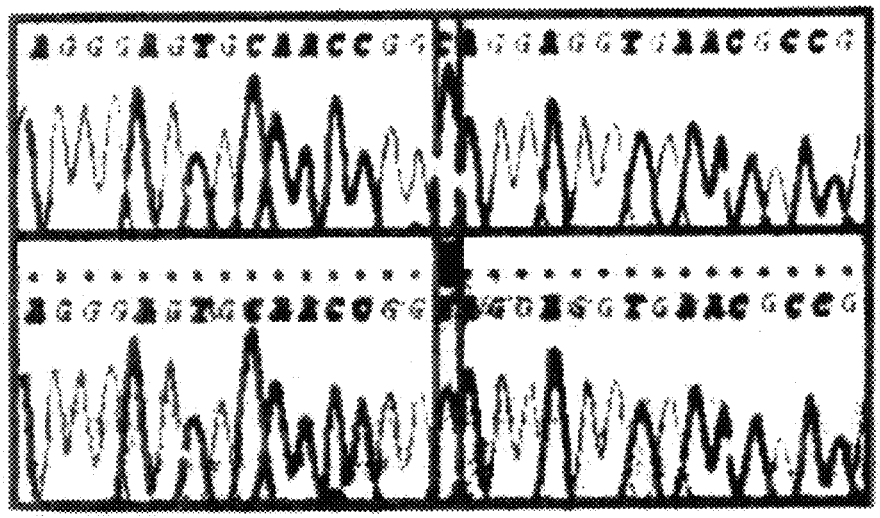

FIG. 2E: Sequence Analysis of Del 2596-2597by ABI Prism® SeqScape software
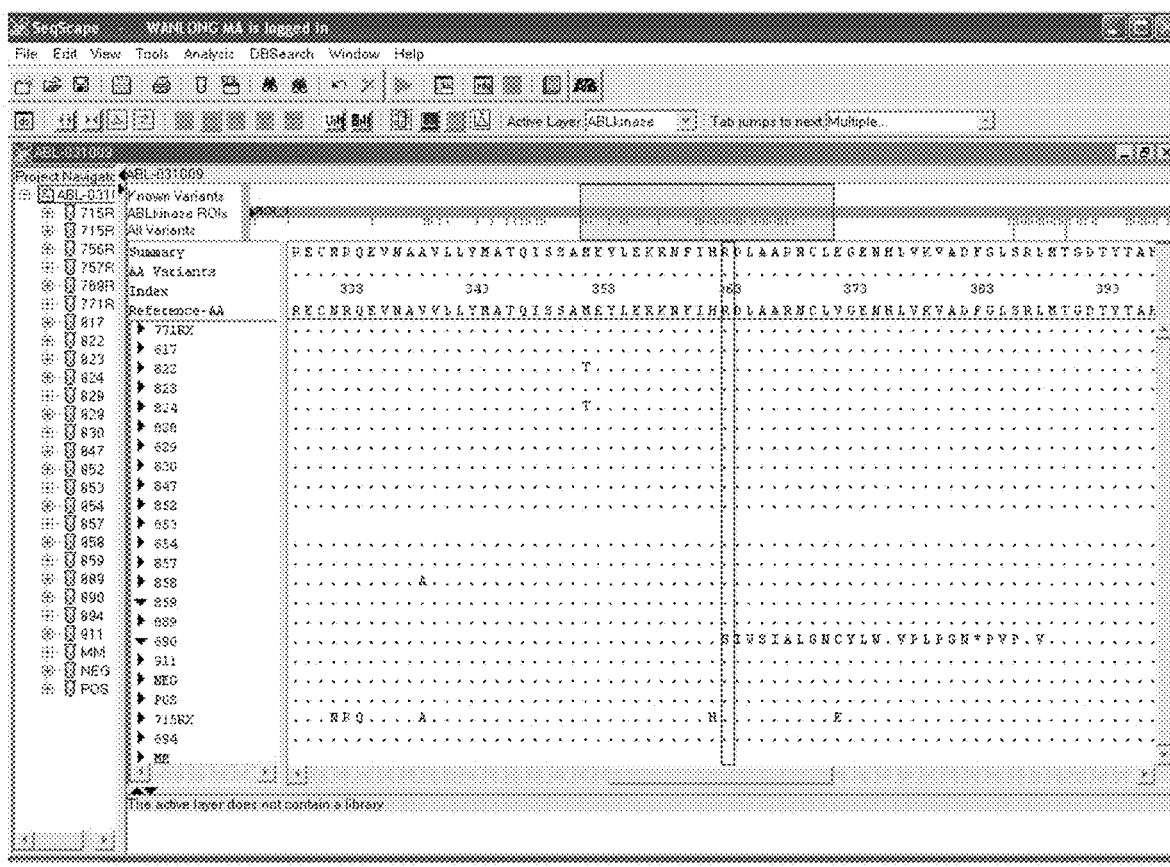

SEQUENCE LISTING

<160> NUMBER OF SEQ ID NOS: 28

<210> SEQ ID NO 1
<211> LENGTH: 4902
<212> TYPE: DNA
<213> ORGANISM: Homo sapiens

<400> SEQUENCE: 1

```
atggtggacc cggtgggctt cgcggaggcg tggaaggcgc agttcccgga ctcagagccc      60
ccgcgcatgg agctgcgctc agtgggcgac atcgagcagg agctggagcg ctgcaaggcc     120
tccattcggc gcctggagca ggaggtgaac caggagcgct tccgcatgat ctacctgcag     180
acgttgctgg ccaaggaaaa gaagagctat gaccggcagc gatggggctt ccggcgcgcg     240
gcgcaggccc ccgacggcgc ctccgagccc cgagcgtccg cgtcgcgccc gcagccagcg     300
cccgccgacg gagccgaccc gccgcccgcc gaggagcccg aggcccggcc cgacggcgag     360
ggttctccgg gtaaggccag gcccgggacc gcccgcaggc ccggggcagc cgcgtcgggg     420
gaacgggacg accggggacc ccccgccagc gtggcggcgc tcaggtccaa cttcgagcgg     480
atccgcaagg gccatggcca gcccgggcg gacgccgaga agcccttcta cgtgaacgtc     540
gagtttcacc acgagcgcgg cctggtgaag gtcaacgaca aagaggtgtc ggaccgcatc     600
agctccctgg gcagccaggc catgcagatg gagcgcaaaa agtcccagca cggcgcgggc     660
tcgagcgtgg gggatgcatc caggccccct taccggggac gctcctcgga gagcagctgc     720
```

```
ggcgtcgacg gcgactacga ggacgccgag ttgaaccccc gcttcctgaa ggacaacctg    780
atcgacgcca atggcggtag caggcccct tggccgcccc tggagtacca gccctaccag      840
agcatctacg tcggggcat gatggaaggg gagggcaagg gcccgctcct gcgcagccag      900
agcacctctg agcaggagaa gcgccttacc tggccccgca ggtcctactc cccccggagt    960
tttgaggatt gcggaggcgg ctatacccg gactgcagct ccaatgagaa cctcacctcc     1020
agcgaggagg acttctcctc tggccagtcc agccgcgtgt ccccaagccc caccacctac   1080
cgcatgttcc gggacaaaag ccgctctccc tcgcagaact cgcaacagtc cttcgacagc    1140
agcagtcccc ccacgccgca gtgccataag cggcaccggc actgcccggt tgtcgtgtcc    1200
gaggccacca tcgtgggcgt ccgcaagacc gggcagatct ggcccaacga tggcgagggc    1260
gccttccatg gagacgcaga tggctcgttc ggaacaccac ctggatacgg ctgcgctgca    1320 gacccgggcag aggagcagcg ccggcaccaa gatgggctgc cctacattga tgactcgccc   1380
tcctcatcgc cccacctcag cagcaagggc aggggcagcc gggatgcgct ggtctcggga    1440
gccctggagt ccactaaagc gagtgagctg gacttggaaa agggcttgga gatgagaaaa    1500
tgggtcctgt cgggaatcct ggctagcgag gagacttacc tgagccacct ggaggcactg    1560
ctgctgccca tgaagccttt gaaagccgct gccaccacct ctcagccggt gctgacgagt    1620
cagcagatcg agaccatctt cttcaaagtg cctgagctct acgagatcca caaggagttc    1680
tatgatgggc tcttccccg cgtgcagcag tggagccacc agcagcgggt gggcgacctc    1740
ttccagaagc tggccagcca gctgggtgtg taccgggtct taggctataa tcacaatggg    1800
gaatggtgtg aagcccaaac caaaatggc caaggctggg tcccaagcaa ctacatcacg    1860
ccagtcaaca gtctggagaa acactcctgg taccatgggc ctgtgtcccg caatgccgct    1920
gagtatctgc tgagcagcgg gatcaatggc agcttcttgg tgcgtgagag tgagagcagt    1980
cctggccaga ggtccatctc gctgagatac gaagggaggg tgtaccatta caggatcaac    2040
actgcttctg atggcaagct ctacgtctcc tccgagagcc gcttcaacac cctgccgag     2100 ttggttcatc atcattcaac ggtggccgac gggctcatca ccacgctcca ttatccagcc    2160
ccaaagcgca caagcccac tgtctatggt gtgtcccca actacgacaa gtgggagatg     2220
gaacgcacgg acatcaccat gaagcacaag ctgggcgggg gccagtacgg ggaggtgtac    2280
gagggcgtgt ggaagaaata cagcctgacg gtggccgtga agaccttgaa ggaggacacc    2340
atggaggtgg aagagttctt gaaagaagct gcagtcatga agagatcaa acaccctaac    2400 ctggtgcagc tccttgggt ctgcacccgg gagcccccgt tctatatcat cactgagttc     2460
atgacctacg ggaacctcct ggactacctg agggagtgca accggcagga ggtgaacgcc    2520
gtggtgctgc tgtacatggc cactcagatc tcgtcagcca tggagtacct ggagaagaaa    2580
aacttcatcc acagagatct tgctgcccga aactgcctgg taggggagaa ccacttggtg    2640
aaggtagctg attttggcct gagcaggttg atgacagggg acacctacac agcccatgct    2700
ggagccaagt tccccatcaa atggactgca cccgagagcc tggcctacaa caagttctcc    2760
atcaagtccg acgtctggc atttggagta ttgctttggg aaattgctac ctatggcatg    2820
tccccttacc cgggaattga cctgtcccag gtgtatgagc tgctagagaa ggactaccgc    2880
atggagcgcc cagaaggctg cccagagaag gtctatgaac tcatgcgagc atgttggcag    2940
tggaatccct ctgaccggcc ctcctttgct gaaatccacc aagcctttga aacaatgttc    3000
caggaatcca gtatctcaga cgaagtggaa aaggagctgg ggaaacaagg cgtccgtggg    3060
gctgtgagta ccttgctgca ggccccagag ctgcccacca agacgaggac ctccaggaga    3120
```

-continued

```
gctgcagagc acagagacac cactgacgtg cctgagatgc ctcactccaa gggccaggga    3180
gagagcgatc ctctggacca tgagcctgcc gtgtctccat tgctccctcg aaaagagcga    3240
ggtcccccgg agggcggcct gaatgaagat gagcgccttc ccccaaaga caaaagacc      3300 aacttgttca gcgccttgat caagaagaag aagaagacag ccccaacccc tcccaaacgc    3360
agcagctcct tccgggagat ggacggccag ccggagcgca gagggccgg cgaggaagag     3420 ggccgagaca tcagcaacgg ggcactggct ttcaccccct tggacacagc tgacccagcc    3480
aagtccccaa agcccagcaa tggggctggg gtccccaatg gagccctccg ggagtccggg    3540
ggctcaggct tccggtctcc ccacctgtgg aagaagtcca gcacgctgac cagcagccgc    3600
ctagccaccg gcgaggagga gggcggtggc agctccagca gcgcttcct gcgctcttgc     3660 tccgcctcct gcgttcccca tggggccaag gacacggagt ggaggtcagt cacgctgcct    3720
cgggacttgc agtccacggg aagacagttt gactcgtcca catttggagg gcacaaaagt    3780
gagaagccgg ctctgcctcg gaagagggca ggggagaaca ggtctgacca ggtgaccccga    3840 ggcacagtaa cgcctccccc caggctggtg aaaagaatg aggaagctgc tgatgaggtc     3900
ttcaaagaca tcatggagtc cagcccgggc tccagcccgc ccaacctgac tccaaaaccc    3960
ctccggcggc aggtcaccgt ggcccctgcc tcgggcctcc cccacaagga agaagctgga   4020
aagggcagtg cctagggac ccctgctgca gctgagccag tgaccccac cagcaaagca     4080 ggctcaggtg caccagggggg caccagcaag ggccccgccg aggagtccag agtgaggagg   4140
cacaagcact cctctgagtc gccagggagg acaagggga aattgtccag gctcaaacct    4200
gccccgccgc cccaccagc agcctctgca gggaaggctg gaggaaagcc ctcgcagagc    4260
ccgagccagg aggcggccgg ggaggcagtc ctgggcgcaa agacaaaagc cacgagtctg    4320
gttgatgctg tgaacagtga cgctgccaag cccagccagc cgggagaggg cctcaaaaag    4380
cccgtgctcc cggccactcc aaagccacag tccgccaagc cgtcggggac ccccatcagc    4440
ccagcccccg ttccctccac gttgccatca gcatcctcgg ccctggcagg ggaccagccg    4500
tcttccaccg ccttcatccc tctcatatca acccgagtgt ctcttcggaa aacccgccag    4560
cctccagagc ggatcgccag cggcgccatc accaagggc tggtcctgga cagcaccgag    4620
gcgctgtgcc tcgccatctc taggaactcc gagcagatgg ccagccacag cgcagtgctg    4680
gaggccggca aaaacctcta cacgttctgc gtgagctatg tggattccat ccagcaaatg    4740
aggaacaagt ttgccttccg agaggccatc aacaaactgg agaataatct ccgggagctt    4800
cagatctgcc cggcgacagc aggcagtggt ccggcggcca ctcaggactt cagcaagctc    4860
ctcagttcgg tgaaggaaat cagtgacata gtgcagaggt ag                       4902
```

<210> SEQ ID NO 2
<211> LENGTH: 1633
<212> TYPE: PRT
<213> ORGANISM: Homo sapiens

<400> SEQUENCE: 2

```
Met Val Asp Pro Val Gly Phe Ala Glu Ala Trp Lys Ala Gln Phe Pro
1               5                   10                  15

Asp Ser Glu Pro Pro Arg Met Glu Leu Arg Ser Val Gly Asp Ile Glu
            20                  25                  30

Gln Glu Leu Glu Arg Cys Lys Ala Ser Ile Arg Arg Leu Glu Gln Glu
        35                  40                  45

Val Asn Gln Glu Arg Phe Arg Met Ile Tyr Leu Gln Thr Leu Leu Ala
```

```
            50                  55                  60
Lys Glu Lys Lys Ser Tyr Asp Arg Gln Arg Trp Gly Phe Arg Arg Ala
 65                  70                  75                  80

Ala Gln Ala Pro Asp Gly Ala Ser Glu Pro Arg Ala Ser Ala Ser Arg
                 85                  90                  95

Pro Gln Pro Ala Pro Ala Asp Gly Ala Asp Pro Pro Ala Glu Glu
                100                 105                 110

Pro Glu Ala Arg Pro Asp Gly Glu Gly Ser Pro Gly Lys Ala Arg Pro
                115                 120                 125

Gly Thr Ala Arg Arg Pro Gly Ala Ala Ala Ser Gly Glu Arg Asp Asp
                130                 135                 140

Arg Gly Pro Pro Ala Ser Val Ala Ala Leu Arg Ser Asn Phe Glu Arg
145                 150                 155                 160

Ile Arg Lys Gly His Gly Gln Pro Gly Ala Asp Ala Glu Lys Pro Phe
                165                 170                 175

Tyr Val Asn Val Glu Phe His His Glu Arg Gly Leu Val Lys Val Asn
                180                 185                 190

Asp Lys Glu Val Ser Asp Arg Ile Ser Ser Leu Gly Ser Gln Ala Met
                195                 200                 205

Gln Met Glu Arg Lys Lys Ser Gln His Gly Ala Gly Ser Ser Val Gly
210                 215                 220

Asp Ala Ser Arg Pro Pro Tyr Arg Gly Arg Ser Ser Glu Ser Ser Cys
225                 230                 235                 240

Gly Val Asp Gly Asp Tyr Glu Asp Ala Glu Leu Asn Pro Arg Phe Leu
                245                 250                 255

Lys Asp Asn Leu Ile Asp Ala Asn Gly Gly Ser Arg Pro Pro Trp Pro
                260                 265                 270

Pro Leu Glu Tyr Gln Pro Tyr Gln Ser Ile Tyr Val Gly Gly Met Met
                275                 280                 285

Glu Gly Glu Gly Lys Gly Pro Leu Leu Arg Ser Gln Ser Thr Ser Glu
                290                 295                 300

Gln Glu Lys Arg Leu Thr Trp Pro Arg Arg Ser Tyr Ser Pro Arg Ser
305                 310                 315                 320

Phe Glu Asp Cys Gly Gly Gly Tyr Thr Pro Asp Cys Ser Ser Asn Glu
                325                 330                 335

Asn Leu Thr Ser Ser Glu Glu Asp Phe Ser Ser Gly Gln Ser Ser Arg
                340                 345                 350

Val Ser Pro Ser Pro Thr Thr Tyr Arg Met Phe Arg Asp Lys Ser Arg
                355                 360                 365

Ser Pro Ser Gln Asn Ser Gln Gln Ser Phe Asp Ser Ser Pro Pro
                370                 375                 380

Thr Pro Gln Cys His Lys Arg His Arg His Cys Pro Val Val Val Ser
385                 390                 395                 400

Glu Ala Thr Ile Val Gly Val Arg Lys Thr Gly Gln Ile Trp Pro Asn
                405                 410                 415

Asp Gly Glu Gly Ala Phe His Gly Asp Ala Asp Gly Ser Phe Gly Thr
                420                 425                 430

Pro Pro Gly Tyr Gly Cys Ala Ala Asp Arg Ala Glu Glu Gln Arg Arg
                435                 440                 445

His Gln Asp Gly Leu Pro Tyr Ile Asp Asp Ser Pro Ser Ser Ser Pro
                450                 455                 460

His Leu Ser Ser Lys Gly Arg Gly Ser Arg Asp Ala Leu Val Ser Gly
465                 470                 475                 480
```

```
Ala Leu Glu Ser Thr Lys Ala Ser Glu Leu Asp Leu Glu Lys Gly Leu
            485             490             495

Glu Met Arg Lys Trp Val Leu Ser Gly Ile Leu Ala Ser Glu Glu Thr
            500             505             510

Tyr Leu Ser His Leu Glu Ala Leu Leu Pro Met Lys Pro Leu Lys
            515             520             525

Ala Ala Ala Thr Thr Ser Gln Pro Val Leu Thr Ser Gln Gln Ile Glu
            530             535             540

Thr Ile Phe Phe Lys Val Pro Glu Leu Tyr Glu Ile His Lys Glu Phe
545             550             555             560

Tyr Asp Gly Leu Phe Pro Arg Val Gln Gln Trp Ser His Gln Gln Arg
            565             570             575

Val Gly Asp Leu Phe Gln Lys Leu Ala Ser Gln Leu Gly Val Tyr Arg
            580             585             590

Val Leu Gly Tyr Asn His Asn Gly Glu Trp Cys Glu Ala Gln Thr Lys
            595             600             605

Asn Gly Gln Gly Trp Val Pro Ser Asn Tyr Ile Thr Pro Val Asn Ser
            610             615             620

Leu Glu Lys His Ser Trp Tyr His Gly Pro Val Ser Arg Asn Ala Ala
625             630             635             640

Glu Tyr Leu Leu Ser Ser Gly Ile Asn Gly Ser Phe Leu Val Arg Glu
            645             650             655

Ser Glu Ser Ser Pro Gly Gln Arg Ser Ile Ser Leu Arg Tyr Glu Gly
            660             665             670

Arg Val Tyr His Tyr Arg Ile Asn Thr Ala Ser Asp Gly Lys Leu Tyr
            675             680             685

Val Ser Ser Glu Ser Arg Phe Asn Thr Leu Ala Glu Leu Val His His
            690             695             700

His Ser Thr Val Ala Asp Gly Leu Ile Thr Thr Leu His Tyr Pro Ala
705             710             715             720

Pro Lys Arg Asn Lys Pro Thr Val Tyr Gly Val Ser Pro Asn Tyr Asp
            725             730             735

Lys Trp Glu Met Glu Arg Thr Asp Ile Thr Met Lys His Lys Leu Gly
            740             745             750

Gly Gly Gln Tyr Gly Glu Val Tyr Glu Gly Val Trp Lys Lys Tyr Ser
            755             760             765

Leu Thr Val Ala Val Lys Thr Leu Lys Glu Asp Thr Met Glu Val Glu
            770             775             780

Glu Phe Leu Lys Glu Ala Ala Val Met Lys Glu Ile Lys His Pro Asn
785             790             795             800

Leu Val Gln Leu Leu Gly Val Cys Thr Arg Glu Pro Pro Phe Tyr Ile
            805             810             815

Ile Thr Glu Phe Met Thr Tyr Gly Asn Leu Leu Asp Tyr Leu Arg Glu
            820             825             830

Cys Asn Arg Gln Glu Val Asn Ala Val Val Leu Leu Tyr Met Ala Thr
            835             840             845

Gln Ile Ser Ser Ala Met Glu Tyr Leu Glu Lys Lys Asn Phe Ile His
            850             855             860

Arg Asp Leu Ala Ala Arg Asn Cys Leu Val Gly Glu Asn His Leu Val
865             870             875             880

Lys Val Ala Asp Phe Gly Leu Ser Arg Leu Met Thr Gly Asp Thr Tyr
            885             890             895
```

```
Thr Ala His Ala Gly Ala Lys Phe Pro Ile Lys Trp Thr Ala Pro Glu
            900                 905                 910

Ser Leu Ala Tyr Asn Lys Phe Ser Ile Lys Ser Asp Val Trp Ala Phe
        915                 920                 925

Gly Val Leu Leu Trp Glu Ile Ala Thr Tyr Gly Met Ser Pro Tyr Pro
    930                 935                 940

Gly Ile Asp Leu Ser Gln Val Tyr Glu Leu Leu Glu Lys Asp Tyr Arg
945                 950                 955                 960

Met Glu Arg Pro Glu Gly Cys Pro Glu Lys Val Tyr Glu Leu Met Arg
                965                 970                 975

Ala Cys Trp Gln Trp Asn Pro Ser Asp Arg Pro Ser Phe Ala Glu Ile
            980                 985                 990

His Gln Ala Phe Glu Thr Met Phe Gln Glu Ser Ser Ile Ser Asp Glu
        995                 1000                1005

Val Glu Lys Glu Leu Gly Lys Gln Gly Val Arg Gly Ala Val Ser
    1010                1015                1020

Thr Leu Leu Gln Ala Pro Glu Leu Pro Thr Lys Thr Arg Thr Ser
    1025                1030                1035

Arg Arg Ala Ala Glu His Arg Asp Thr Thr Asp Val Pro Glu Met
    1040                1045                1050

Pro His Ser Lys Gly Gln Gly Glu Ser Asp Pro Leu Asp His Glu
    1055                1060                1065

Pro Ala Val Ser Pro Leu Leu Pro Arg Lys Glu Arg Gly Pro Pro
    1070                1075                1080

Glu Gly Gly Leu Asn Glu Asp Glu Arg Leu Leu Pro Lys Asp Lys
    1085                1090                1095

Lys Thr Asn Leu Phe Ser Ala Leu Ile Lys Lys Lys Lys Lys Thr
    1100                1105                1110

Ala Pro Thr Pro Pro Lys Arg Ser Ser Ser Phe Arg Glu Met Asp
    1115                1120                1125

Gly Gln Pro Glu Arg Arg Gly Ala Gly Glu Glu Gly Arg Asp
    1130                1135                1140

Ile Ser Asn Gly Ala Leu Ala Phe Thr Pro Leu Asp Thr Ala Asp
    1145                1150                1155

Pro Ala Lys Ser Pro Lys Pro Ser Asn Gly Ala Gly Val Pro Asn
    1160                1165                1170

Gly Ala Leu Arg Glu Ser Gly Gly Ser Gly Phe Arg Ser Pro His
    1175                1180                1185

Leu Trp Lys Lys Ser Ser Thr Leu Thr Ser Ser Arg Leu Ala Thr
    1190                1195                1200

Gly Glu Glu Glu Gly Gly Gly Ser Ser Ser Lys Arg Phe Leu Arg
    1205                1210                1215

Ser Cys Ser Ala Ser Cys Val Pro His Gly Ala Lys Asp Thr Glu
    1220                1225                1230

Trp Arg Ser Val Thr Leu Pro Arg Asp Leu Gln Ser Thr Gly Arg
    1235                1240                1245

Gln Phe Asp Ser Ser Thr Phe Gly Gly His Lys Ser Glu Lys Pro
    1250                1255                1260

Ala Leu Pro Arg Lys Arg Ala Gly Glu Asn Arg Ser Asp Gln Val
    1265                1270                1275

Thr Arg Gly Thr Val Thr Pro Pro Pro Arg Leu Val Lys Lys Asn
    1280                1285                1290

Glu Glu Ala Ala Asp Glu Val Phe Lys Asp Ile Met Glu Ser Ser
```

```
            1295                1300                1305

Pro Gly Ser Ser Pro Pro Asn Leu Thr Pro Lys Pro Leu Arg Arg
        1310                1315                1320

Gln Val Thr Val Ala Pro Ala Ser Gly Leu Pro His Lys Glu Glu
    1325                1330                1335

Ala Gly Lys Gly Ser Ala Leu Gly Thr Pro Ala Ala Ala Glu Pro
1340                1345                1350

Val Thr Pro Thr Ser Lys Ala Gly Ser Gly Ala Pro Gly Gly Thr
        1355                1360                1365

Ser Lys Gly Pro Ala Glu Glu Ser Arg Val Arg Arg His Lys His
    1370                1375                1380

Ser Ser Glu Ser Pro Gly Arg Asp Lys Gly Lys Leu Ser Arg Leu
1385                1390                1395

Lys Pro Ala Pro Pro Pro Pro Ala Ala Ser Ala Gly Lys Ala
        1400                1405                1410

Gly Gly Lys Pro Ser Gln Ser Pro Ser Gln Glu Ala Ala Gly Glu
    1415                1420                1425

Ala Val Leu Gly Ala Lys Thr Lys Ala Thr Ser Leu Val Asp Ala
1430                1435                1440

Val Asn Ser Asp Ala Ala Lys Pro Ser Gln Pro Gly Glu Gly Leu
        1445                1450                1455

Lys Lys Pro Val Leu Pro Ala Thr Pro Lys Pro Gln Ser Ala Lys
    1460                1465                1470

Pro Ser Gly Thr Pro Ile Ser Pro Ala Pro Val Pro Ser Thr Leu
1475                1480                1485

Pro Ser Ala Ser Ser Ala Leu Ala Gly Asp Gln Pro Ser Ser Thr
        1490                1495                1500

Ala Phe Ile Pro Leu Ile Ser Thr Arg Val Ser Leu Arg Lys Thr
    1505                1510                1515

Arg Gln Pro Pro Glu Arg Ile Ala Ser Gly Ala Ile Thr Lys Gly
1520                1525                1530

Val Val Leu Asp Ser Thr Glu Ala Leu Cys Leu Ala Ile Ser Arg
        1535                1540                1545

Asn Ser Glu Gln Met Ala Ser His Ser Ala Val Leu Glu Ala Gly
    1550                1555                1560

Lys Asn Leu Tyr Thr Phe Cys Val Ser Tyr Val Asp Ser Ile Gln
1565                1570                1575

Gln Met Arg Asn Lys Phe Ala Phe Arg Glu Ala Ile Asn Lys Leu
        1580                1585                1590

Glu Asn Asn Leu Arg Glu Leu Gln Ile Cys Pro Ala Thr Ala Gly
    1595                1600                1605

Ser Gly Pro Ala Ala Thr Gln Asp Phe Ser Lys Leu Leu Ser Ser
1610                1615                1620

Val Lys Glu Ile Ser Asp Ile Val Gln Arg
        1625                1630

<210> SEQ ID NO 3
<211> LENGTH: 4717
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
```

```
atggtggacc cggtgggctt cgcggaggcg tggaaggcgc agttcccgga ctcagagccc    60
ccgcgcatgg agctgcgctc agtgggcgac atcgagcagg agctgagcg ctgcaaggcc   120 tccattcggc gcctggagca ggaggtgaac caggagcgct tccgcatgat ctacctgcag   180
acgttgctgg ccaaggaaaa gaagagctat gaccggcagc gatggggctt ccggcgcgcg   240
gcgcaggccc ccgacggcgc ctccgagccc cgagcgtccg cgtcgcgccc gcagccagcg   300
cccgccgacg gagccgaccc gccgcccgcc gaggagcccg aggccggcc cgacggcgag   360 ggttctccgg gtaaggccag gcccgggacc gcccgcaggc ccggggcagc cgcgtcgggg   420
gaacgggacg accggggacc ccccgccagc gtggcggcgc tcaggtccaa cttcgagcgg   480
atccgcaagg gccatggcca gcccggggcg gacgccgaga agcccttcta cgtgaacgtc   540
gagtttcacc acgagcgcgg cctggtgaag gtcaacgaca aagaggtgtc ggaccgcatc   600
agctccctgg gcagccaggc catgcagatg gagcgcaaaa agtcccagca cggcgcgggc   660
tcgagcgtgg gggatgcatc caggccccct taccggggac gctcctcgga gagcagctgc   720
ggcgtcgacg gcgactacga ggacgccgag ttgaaccccc gcttcctgaa ggacaacctg   780
atcgacgcca atggcggtag caggcccct tggccgcccc tggagtacca gccctaccag   840
agcatctacg tcgggggcat gatggaaggg gagggcaagg gcccgctcct cgcgcagccag   900 agcacctctg agcaggagaa gcgccttacc tggccccgca ggtcctactc ccccggagt   960 tttgaggatt gcggaggcgg ctataccccg gactgcagct ccaatgagaa cctcacctcc   1020
agcgaggagg acttctcctc tggccagtcc agccgcgtgt ccccaagccc caccacctac   1080
cgcatgttcc gggacaaaag ccgctctccc tcgcagaact cgcaacagtc cttcgacagc   1140
agcagtcccc ccacgccgca gtgccataag cggcaccggc actgcccggt tgtcgtgtcc   1200
gaggccacca tcgtgggcgt ccgcaagacc gggcagatct ggcccaacga tggcgagggc   1260
gccttccatg gagacgcaga tggctcgttc ggaacaccac ctggatacgg ctgcgctgca   1320
gaccgggcag aggagcagcg ccggcaccaa gatgggctgc cctacattga tgactcgccc   1380
tcctcatcgc cccacctcag cagcaagggc aggggcagcc gggatgcgct ggtctcggga   1440
gccctggagt ccactaaagc gagtgagctg gacttggaaa agggcttgga gatgagaaaa   1500
tgggtcctgt cgggaatcct ggctagcgag gagacttacc tgagccacct ggaggcactg   1560
ctgctgccca tgaagccttt gaaagccgct gccaccacct tcagccggt gctgacgagt   1620 cagcagatcg agaccatctt cttcaaagtg cctgagctct acgagatcca aaggagttc   1680 tatgatgggc tcttccccg cgtgcagcag tggagccacc agcagcgggt gggcgacctc   1740
ttccagaagc tggccagcca gctgggtgtg taccgggtct taggctataa tcacaatggg   1800
gaatggtgtg aagcccaaac caaaatggc caaggctggg tcccaagcaa ctacatcacg   1860
ccagtcaaca gtctggagaa acactcctgg taccatgggc ctgtgtcccg caatgccgct   1920
gagtatctgc tgagcagcgg gatcaatggc agcttcttgg tgcgtgagag tgagagcagt   1980
cctggccaga ggtccatctc gctgagatac gaagggaggg tgtaccatta caggatcaac   2040
actgcttctg atggcaagct ctacgtctcc tccgagagcc gcttcaacac cctggccgag   2100
ttggttcatc atcattcaac ggtggccgac gggctcatca ccacgctcca ttatccagcc   2160
ccaaagcgca caagcccac tgtctatggt gtgtccccca actacgacaa gtgggagatg   2220
gaacgcacgg acatcaccat gaagcacaag ctgggcgggg gccagtacgg ggaggtgtac   2280
gagggcgtgt ggaagaaata cagcctgacg gtggccgtga gaccttgaa ggaggacacc   2340 atggaggtgg aagagttctt gaaagaagct gcagtcatga aagagatcaa acaccctaac   2400
```

```
ctggtgcagc tccttggggt ctgcacccgg gagcccccgt tctatatcat cactgagttc    2460
atgacctacg ggaacctcct ggactacctg agggagtgca accggcagga ggtgaacgcc    2520
gtggtgctgc tgtacatggc cactcagatc tcgtcagcca tggagtacct ggagaagaaa    2580
aacttcatcc acagcatttg gagtattgct ttgggaaatt gctacctatg gcatgtcccc    2640
ttacccggga attgacctgt cccaggtgta tgagctgcta gagaaggact accgcatgga    2700
gcgcccagaa ggctgcccag agaaggtcta tgaactcatg cgagcatgtt ggcagtggaa    2760
tccctctgac cggccctcct ttgctgaaat ccaccaagcc tttgaaacaa tgttccagga    2820
atccagtatc tcagacgaag tggaaaagga gctggggaaa caaggcgtcc gtggggctgt    2880
gagtaccttg ctgcaggccc agagctgcc caccaagacg aggacctcca ggagagctgc    2940
agagcacaga gacaccactg acgtgcctga gatgcctcac tccaagggcc agggagagag    3000
cgatcctctg gaccatgagc ctgccgtgtc tccattgctc cctcgaaaag agcgaggtcc    3060
cccggagggc ggcctgaatg aagatgagcg ccttctcccc aaagacaaaa agaccaactt    3120
gttcagcgcc ttgatcaaga gaagaagaa gacagcccca ccccctccca aacgcagcag    3180
ctccttccgg gagatggacg gccagccgga gcgcagaggg gccggcgagg aagagggccg    3240
agacatcagc aacggggcac tggctttcac ccccttggac acagctgacc cagccaagtc    3300
cccaaagccc agcaatgggg ctggggtccc caatggagcc ctccgggagt ccgggggctc    3360
aggcttccgg tctccccacc tgtggaagaa gtccagcacg ctgaccagca gccgcctagc    3420
caccggcgag gaggagggcg gtggcagctc agcaagcgc ttcctgcgct cttgctccgc    3480
ctcctgcgtt cccatggggg ccaaggacac ggagtggagg tcagtcacgc tgcctcggga    3540
cttgcagtcc acgggaagac agtttgactc gtccacattt ggagggcaca aaagtgagaa    3600
gccggctctg cctcggaaga gggcagggga gaacaggtct gaccaggtga cccgaggcac    3660
agtaacgcct ccccccaggc tggtgaaaaa gaatgaggaa gctgctgatg aggtcttcaa    3720
agacatcatg gagtccagcc cgggctccag cccgcccaac ctgactccaa aacccctccg    3780
gcggcaggtc accgtggccc ctgcctcggg cctcccccac aaggaagaag ctggaaaggg    3840
cagtgcctta gggacccctg ctgcagctga gccagtgacc cccaccagca aagcaggctc    3900
aggtgcacca gggggcacca gcaagggccc cgccgaggag tccagagtga ggaggcacaa    3960
gcactcctct gagtcgccag ggaggacaa ggggaaattg tccaggctca acctgccccc    4020
gccgccccca ccagcagcct ctgcaggaa ggctggagga aagccctcgc agagcccgag    4080
ccaggaggcg gccggggagg cagtcctggg cgcaaagaca aaagccacga gtctggttga    4140
tgctgtgaac agtgacgctg ccaagcccag ccagccggga gagggcctca aaaagcccgt    4200
gctcccggcc actccaaagc cacagtccgc caagccgtcg ggaccccca tcagcccagc    4260 ccccgttccc tccacgttgc catcagcatc ctcggccctg cagggggacc agccgtcttc    4320
caccgccttc atccctctca tatcaacccg agtgtctctt cggaaaaccc gccagcctcc    4380
agagcggatc gccagcggcg ccatcaccaa gggcgtggtc ctggacagca ccgaggcgct    4440
gtgcctcgcc atctctagga actccgagca gatggccagc cacagcgcag tgctggaggc    4500
cggcaaaaac ctctacacgt tctgcgtgag ctatgtggat tccatccagc aaatgcagat    4560
aggaacaagt ttgccttccg agaggccatc aacaaactgg agaataatct ccgggagctt    4620
ctgcccggcg acagcaggca gtggtccggc ggcactcag gacttcagca agctcctcag    4680
ttcggtgaag gaaatcagtg acatagtgca gaggtag                             4717
```

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 4
aacttcatcc acagcatttg gagtattgc                                           29

<210> SEQ ID NO 5
<211> LENGTH: 884
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 5

Met Val Asp Pro Val Gly Phe Ala Glu Ala Trp Lys Ala Gln Phe Pro
1               5                   10                  15

Asp Ser Glu Pro Pro Arg Met Glu Leu Arg Ser Val Gly Asp Ile Glu
            20                  25                  30

Gln Glu Leu Glu Arg Cys Lys Ala Ser Ile Arg Arg Leu Glu Gln Glu
        35                  40                  45

Val Asn Gln Glu Arg Phe Arg Met Ile Tyr Leu Gln Thr Leu Leu Ala
    50                  55                  60

Lys Glu Lys Lys Ser Tyr Asp Arg Gln Arg Trp Gly Phe Arg Arg Ala
65                  70                  75                  80

Ala Gln Ala Pro Asp Gly Ala Ser Glu Pro Arg Ala Ser Ala Ser Arg
                85                  90                  95

Pro Gln Pro Ala Pro Ala Asp Gly Ala Asp Pro Pro Ala Glu Glu
            100                 105                 110

Pro Glu Ala Arg Pro Asp Gly Glu Gly Ser Pro Gly Lys Ala Arg Pro
        115                 120                 125

Gly Thr Ala Arg Arg Pro Gly Ala Ala Ala Ser Gly Glu Arg Asp Asp
    130                 135                 140

Arg Gly Pro Pro Ala Ser Val Ala Ala Leu Arg Ser Asn Phe Glu Arg
145                 150                 155                 160

Ile Arg Lys Gly His Gly Gln Pro Gly Ala Asp Ala Glu Lys Pro Phe
                165                 170                 175

Tyr Val Asn Val Glu Phe His His Glu Arg Gly Leu Val Lys Val Asn
            180                 185                 190

Asp Lys Glu Val Ser Asp Arg Ile Ser Ser Leu Gly Ser Gln Ala Met
        195                 200                 205

Gln Met Glu Arg Lys Lys Ser Gln His Gly Ala Gly Ser Ser Val Gly
    210                 215                 220

Asp Ala Ser Arg Pro Pro Tyr Arg Gly Arg Ser Ser Glu Ser Ser Cys
225                 230                 235                 240

Gly Val Asp Gly Asp Tyr Glu Asp Ala Glu Leu Asn Pro Arg Phe Leu
                245                 250                 255

Lys Asp Asn Leu Ile Asp Ala Asn Gly Gly Ser Arg Pro Pro Trp Pro
            260                 265                 270

Pro Leu Glu Tyr Gln Pro Tyr Gln Ser Ile Tyr Val Gly Gly Met Met
        275                 280                 285

Glu Gly Glu Gly Lys Gly Pro Leu Leu Arg Ser Gln Ser Thr Ser Glu

```
             290                 295                 300
    Gln Glu Lys Arg Leu Thr Trp Pro Arg Arg Ser Tyr Ser Pro Arg Ser
    305                 310                 315                 320

Phe Glu Asp Cys Gly Gly Tyr Thr Pro Asp Cys Ser Ser Asn Glu
                    325                 330                 335

Asn Leu Thr Ser Ser Glu Glu Asp Phe Ser Ser Gly Gln Ser Ser Arg
                    340                 345                 350

Val Ser Pro Ser Pro Thr Thr Tyr Arg Met Phe Arg Asp Lys Ser Arg
                    355                 360                 365

Ser Pro Ser Gln Asn Ser Gln Gln Ser Phe Asp Ser Ser Ser Pro Pro
                    370                 375                 380

Thr Pro Gln Cys His Lys Arg His Arg His Cys Pro Val Val Val Ser
    385                 390                 395                 400

Glu Ala Thr Ile Val Gly Val Arg Lys Thr Gly Gln Ile Trp Pro Asn
                    405                 410                 415

Asp Gly Glu Gly Ala Phe His Gly Asp Ala Asp Gly Ser Phe Gly Thr
                    420                 425                 430

Pro Pro Gly Tyr Gly Cys Ala Ala Asp Arg Ala Glu Glu Gln Arg Arg
                    435                 440                 445

His Gln Asp Gly Leu Pro Tyr Ile Asp Asp Ser Pro Ser Ser Ser Pro
    450                 455                 460

His Leu Ser Ser Lys Gly Arg Gly Ser Arg Asp Ala Leu Val Ser Gly
    465                 470                 475                 480

Ala Leu Glu Ser Thr Lys Ala Ser Glu Leu Asp Leu Glu Lys Gly Leu
                    485                 490                 495

Glu Met Arg Lys Trp Val Leu Ser Gly Ile Leu Ala Ser Glu Glu Thr
                    500                 505                 510

Tyr Leu Ser His Leu Glu Ala Leu Leu Pro Met Lys Pro Leu Lys
                    515                 520                 525

Ala Ala Ala Thr Thr Ser Gln Pro Val Leu Thr Ser Gln Gln Ile Glu
    530                 535                 540

Thr Ile Phe Phe Lys Val Pro Glu Leu Tyr Glu Ile His Lys Glu Phe
    545                 550                 555                 560

Tyr Asp Gly Leu Phe Pro Arg Val Gln Gln Trp Ser His Gln Gln Arg
                    565                 570                 575

Val Gly Asp Leu Phe Gln Lys Leu Ala Ser Gln Leu Gly Val Tyr Arg
                    580                 585                 590

Val Leu Gly Tyr Asn His Asn Gly Glu Trp Cys Glu Ala Gln Thr Lys
                    595                 600                 605

Asn Gly Gln Gly Trp Val Pro Ser Asn Tyr Ile Thr Pro Val Asn Ser
    610                 615                 620

Leu Glu Lys His Ser Trp Tyr His Gly Pro Val Ser Arg Asn Ala Ala
    625                 630                 635                 640

Glu Tyr Leu Leu Ser Ser Gly Ile Asn Gly Ser Phe Leu Val Arg Glu
                    645                 650                 655

Ser Glu Ser Ser Pro Gly Gln Arg Ser Ile Ser Leu Arg Tyr Glu Gly
                    660                 665                 670

Arg Val Tyr His Tyr Arg Ile Asn Thr Ala Ser Asp Gly Lys Leu Tyr
                    675                 680                 685

Val Ser Ser Glu Ser Arg Phe Asn Thr Leu Ala Glu Leu Val His His
                    690                 695                 700

His Ser Thr Val Ala Asp Gly Leu Ile Thr Thr Leu His Tyr Pro Ala
    705                 710                 715                 720
```

```
Pro Lys Arg Asn Lys Pro Thr Val Tyr Gly Val Ser Pro Asn Tyr Asp
                725                 730                 735

Lys Trp Glu Met Glu Arg Thr Asp Ile Thr Met Lys His Lys Leu Gly
            740                 745                 750

Gly Gly Gln Tyr Gly Glu Val Tyr Glu Gly Val Trp Lys Lys Tyr Ser
        755                 760                 765

Leu Thr Val Ala Val Lys Thr Leu Lys Glu Asp Thr Met Glu Val Glu
    770                 775                 780

Glu Phe Leu Lys Glu Ala Ala Val Met Lys Glu Ile Lys His Pro Asn
785                 790                 795                 800

Leu Val Gln Leu Leu Gly Val Cys Thr Arg Glu Pro Pro Phe Tyr Ile
                805                 810                 815

Ile Thr Glu Phe Met Thr Tyr Gly Asn Leu Leu Asp Tyr Leu Arg Glu
            820                 825                 830

Cys Asn Arg Gln Glu Val Asn Ala Val Val Leu Leu Tyr Met Ala Thr
        835                 840                 845

Gln Ile Ser Ser Ala Met Glu Tyr Leu Glu Lys Lys Asn Phe Ile His
    850                 855                 860

Ser Ile Trp Ser Ile Ala Leu Gly Asn Cys Tyr Leu Trp His Val Pro
865                 870                 875                 880

Leu Pro Gly Asn
```

<210> SEQ ID NO 6
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 6

```
Glu Tyr Leu Glu Lys Lys Asn Phe Ile His Ser Ile Trp Ser Ile Ala
1               5                   10                  15

Leu Gly Asn Cys Tyr Leu Trp His Val Pro Leu Pro Gly Asn
            20                  25                  30
```

<210> SEQ ID NO 7
<211> LENGTH: 4900
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7

```
atggtggacc cggtgggctt cgcggaggcg tggaaggcgc agttcccgga ctcagagccc     60
ccgcgcatgg agctgcgctc agtgggcgac atcgagcagg agctggagcg ctgcaaggcc    120
tccattcggc gcctggagca ggaggtgaac caggagcgct tccgcatgat ctacctgcag    180
acgttgctgg ccaaggaaaa gaagagctat gaccggcagc gatggggctt ccggcgcgcg    240
gcgcaggccc ccgacggcgc ctccgagccc cgagcgtccg cgtcgcgccc gcagccagcg    300
cccgccgacg gagccgaccc gccgcccgcc gaggagcccc aggcccggcc cgacggcgag    360
ggttctccgg gtaaggccag gcccgggacc gcccgcaggc ccggggcagc cgcgtcgggg    420
gaacgggacg accgggggacc cccgccagc gtggcggcgc tcaggtccaa cttcgagcgg    480
atccgcaagg gccatggcca gccgggggcg gacgccgaga agcccttcta cgtgaacgtc    540
```

```
gagtttcacc acgagcgcgg cctggtgaag gtcaacgaca aagaggtgtc ggaccgcatc    600
agctccctgg gcagccaggc catgcagatg gagcgcaaaa agtcccagca cggcgcgggc    660
tcgagcgtgg gggatgcatc caggccccct taccggggac gctcctcgga gagcagctgc    720
ggcgtcgacg gcgactacga ggacgccgag ttgaaccccc gcttcctgaa ggacaacctg    780
atcgacgcca atggcggtag caggccccct tggccgcccc tggagtacca gccctaccag    840
agcatctacg tcgggggcat gatggaaggg gagggcaagg gcccgctcct gcgcagccag    900
agcacctctg agcaggagaa gcgccttacc tggccccgca ggtcctactc cccccggagt    960
tttgaggatt gcggaggcgg ctataccccg gactgcagct ccaatgagaa cctcacctcc   1020
agcgaggagg acttctcctc tggccagtcc agccgcgtgt ccccaagccc caccacctac   1080
cgcatgttcc gggacaaaag ccgctctccc tcgcagaact cgcaacagtc cttcgacagc   1140
agcagtcccc ccacgccgca gtgccataag cggcaccggc actgcccggt tgtcgtgtcc   1200
gaggccacca tcgtgggcgt ccgcaagacc gggcagatct ggcccaacga tggcgagggc   1260
gccttccatg gagacgcaga tggctcgttc ggaacaccac ctggatacgg ctgcgctgca   1320
gaccgggcag aggagcagcg ccggcaccaa gatgggctgc cctacattga tgactcgccc   1380
tcctcatcgc cccacctcag cagcaagggc aggggcagcc gggatgcgct ggtctcggga   1440
gccctggagt ccactaaagc gagtgagctg gacttggaaa agggcttgga gatgagaaaa   1500
tgggtcctgt cgggaatcct ggctagcgag gagacttacc tgagccacct ggaggcactg   1560
ctgctgccca tgaagccttt gaaagccgct gccaccacct tcagccggt gctgacgagt   1620 cagcagatcg agaccatctt cttcaaagtg cctgagctct acgagatcca caggagttc   1680 tatgatgggc tcttcccccg cgtgcagcag tggagccacc agcagcgggt gggcgacctc   1740
ttccagaagc tggccagcca gctgggtgtg taccgggtct taggctataa tcacaatggg   1800
gaatggtgtg aagcccaaac caaaaatggc caaggctggg tcccaagcaa ctacatcacg   1860
ccagtcaaca gtctggagaa acactcctgg taccatgggc ctgtgtcccg caatgccgct   1920
gagtatctgc tgagcagcgg gatcaatggc agcttcttgg tgcgtgagag tgagagcagt   1980
cctggccaga ggtccatctc gctgagatac gaagggaggg tgtaccatta caggatcaac   2040
actgcttctg atggcaagct ctacgtctcc tccgagagcc gcttcaacac cctggccgag   2100
ttggttcatc atcattcaac ggtggccgac gggctcatca ccacgctcca ttatccagcc   2160
ccaaagcgca caagcccac tgtctatggt gtgtccccca actacgacaa gtgggagatg   2220
gaacgcacgg acatcaccat gaagcacaag ctgggcgggg gccagtacgg ggaggtgtac   2280
gagggcgtgt ggaagaaata cagcctgacg gtggccgtga agaccttgaa ggaggacacc   2340
atggaggtgg aagagttctt gaaagaagct gcagtcatga aagagatcaa acaccctaac   2400
ctggtgcagc tccttgggt ctgcacccgg gagcccccgt tctatatcat cactgagttc   2460
atgacctacg gaaccctcct ggactacctg agggagtgca accggcagga ggtgaacgcc   2520
gtggtgctgc tgtacatggc cactcagatc tcgtcagcca tggagtacct ggagaagaaa   2580
aacttcatcc acagatcttg ctgcccgaaa ctgcctggta ggggagaacc acttggtgaa   2640
ggtagctgat tttggcctga gcaggttgat gacaggggac acctcacag cccatgctgg   2700 agccaagttc cccatcaaat ggactgcacc cgagagcctg gcctacaaca gttctccat   2760 caagtccgac gtctgggcat ttggagtatt gctttgggaa attgctacct atggcatgtc   2820
cccttacccg ggaattgacc tgtcccaggt gtatgagctg ctagagaagg actaccgcat   2880
ggagcgccca gaaggctgcc cagagaaggt ctatgaactc atgcgagcat gttggcagtg   2940
```

-continued

```
gaatccctct gaccggccct cctttgctga aatccaccaa gcctttgaaa caatgttcca   3000
ggaatccagt atctcagacg aagtggaaaa ggagctgggg aaacaaggcg tccgtggggc   3060
tgtgagtacc ttgctgcagg ccccagagct gcccaccaag acgaggacct ccaggagagc   3120
tgcagagcac agagacacca ctgacgtgcc tgagatgcct cactccaagg gccagggaga   3180
gagcgatcct ctggaccatg agcctgccgt gtctccattg ctccctcgaa agagcgagg   3240 tcccccggag ggcggcctga atgaagatga gcgccttctc cccaaagaca aaagaccaa   3300 cttgttcagc gccttgatca agaagaagaa gaagacagcc ccaaccctc ccaaacgcag    3360 cagctccttc cggagatgg acggccagcc ggagcgcaga ggggccggcg aggaagaggg    3420
ccgagacatc agcaacgggg cactggcttt caccccttg gacacagctg acccagccaa    3480
gtccccaaag cccagcaatg ggctggggt cccaatgga gccctccggg agtccggggg    3540
ctcaggcttc cggtctcccc acctgtggaa gaagtccagc acgctgacca gcagccgcct   3600
agccaccggc gaggaggagg gcggtggcag ctccagcaag cgcttcctgc gctcttgctc   3660
cgcctcctgc gttccccatg gggccaagga cacggagtgg aggtcagtca cgctgcctcg   3720
ggacttgcag tccacgggaa gacagtttga ctcgtccaca tttggagggc acaaaagtga   3780
gaagccggct ctgcctcgga gagggcagg ggagaacagg tctgaccagg tgacccgagg    3840
cacagtaacg cctcccccca ggctggtgaa aaagaatgag gaagctgctg atgaggtctt   3900
caaagacatc atggagtcca gcccgggctc cagcccgccc aacctgactc caaaacccct   3960
ccggcggcag gtcaccgtgg ccctgcctc gggcctcccc cacaaggaag aagctggaaa   4020
gggcagtgcc ttagggaccc ctgctgcagc tgagccagtg accccacca gcaaagcagg   4080 ctcaggtgca ccaggggca ccagcaaggg ccccgccgag gagtccagag tgaggaggca    4140
caagcactcc tctgagtcgc cagggaggga caaggggaaa ttgtccaggc tcaaacctgc   4200
cccgccgccc ccaccagcag cctctgcagg gaaggctgga ggaaagccct cgcagagccc   4260
gagccaggag gcggccgggg aggcagtcct gggcgcaaag acaaaagcca cgagtctggt   4320
tgatgctgtg aacagtgacg ctgccaagcc cagccagccg ggagagggcc tcaaaaagcc   4380
cgtgctcccg gccactccaa agccacagtc cgccaagccc tcggggaccc ccatcagccc   4440 agccccgtt ccctccacgt tgccatcagc atcctcggcc ctggcagggg accagccgtc    4500
ttccaccgcc ttcatccctc tcatatcaac ccgagtgtct cttcggaaaa cccgccagcc   4560
tccagagcgg atcgccagcg cgccatcac caagggcgtg gtcctggaca gcaccgaggc    4620
gctgtgcctc gccatctcta ggaactccga gcagatggcc agccacagcg cagtgctgga   4680
ggccggcaaa aacctctaca cgttctgcgt gagctatgtg gattccatcc agcaaatgag   4740
gaacaagttt gccttccgag aggccatcaa caaactggaa aataatctcc gggagcttca   4800
gatctgcccg gcgacagcag gcagtggtcc ggcggccact caggacttca gcaagctcct   4860
cagttcggtg aaggaaatca gtgacatagt gcagaggtag                          4900
```

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8

```
aacttcatcc acagatcttg ctgcccgaaa                                      30
```

<210> SEQ ID NO 9
<211> LENGTH: 882
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 9

```
Met Val Asp Pro Val Gly Phe Ala Glu Ala Trp Lys Ala Gln Phe Pro
1               5                  10                  15

Asp Ser Glu Pro Pro Arg Met Glu Leu Arg Ser Val Gly Asp Ile Glu
            20                  25                  30

Gln Glu Leu Glu Arg Cys Lys Ala Ser Ile Arg Arg Leu Glu Gln Glu
        35                  40                  45

Val Asn Gln Glu Arg Phe Arg Met Ile Tyr Leu Gln Thr Leu Leu Ala
    50                  55                  60

Lys Glu Lys Lys Ser Tyr Asp Arg Gln Arg Trp Gly Phe Arg Arg Ala
65                  70                  75                  80

Ala Gln Ala Pro Asp Gly Ala Ser Glu Pro Arg Ala Ser Ala Ser Arg
                85                  90                  95

Pro Gln Pro Ala Pro Ala Asp Gly Ala Asp Pro Pro Ala Glu Glu
            100                 105                 110

Pro Glu Ala Arg Pro Asp Gly Glu Gly Ser Pro Gly Lys Ala Arg Pro
        115                 120                 125

Gly Thr Ala Arg Arg Pro Gly Ala Ala Ser Gly Glu Arg Asp Asp
    130                 135                 140

Arg Gly Pro Pro Ala Ser Val Ala Ala Leu Arg Ser Asn Phe Glu Arg
145                 150                 155                 160

Ile Arg Lys Gly His Gly Gln Pro Gly Ala Asp Ala Glu Lys Pro Phe
                165                 170                 175

Tyr Val Asn Val Glu Phe His His Glu Arg Gly Leu Val Lys Val Asn
            180                 185                 190

Asp Lys Glu Val Ser Asp Arg Ile Ser Ser Leu Gly Ser Gln Ala Met
        195                 200                 205

Gln Met Glu Arg Lys Lys Ser Gln His Gly Ala Gly Ser Ser Val Gly
    210                 215                 220

Asp Ala Ser Arg Pro Pro Tyr Arg Gly Arg Ser Ser Glu Ser Ser Cys
225                 230                 235                 240

Gly Val Asp Gly Asp Tyr Glu Asp Ala Glu Leu Asn Pro Arg Phe Leu
                245                 250                 255

Lys Asp Asn Leu Ile Asp Ala Asn Gly Gly Ser Arg Pro Pro Trp Pro
            260                 265                 270

Pro Leu Glu Tyr Gln Pro Tyr Gln Ser Ile Tyr Val Gly Gly Met Met
        275                 280                 285

Glu Gly Glu Gly Lys Gly Pro Leu Leu Arg Ser Gln Ser Thr Ser Glu
    290                 295                 300

Gln Glu Lys Arg Leu Thr Trp Pro Arg Arg Ser Tyr Ser Pro Arg Ser
305                 310                 315                 320

Phe Glu Asp Cys Gly Gly Gly Tyr Thr Pro Asp Cys Ser Ser Asn Glu
                325                 330                 335

Asn Leu Thr Ser Ser Glu Glu Asp Phe Ser Ser Gly Gln Ser Ser Arg
            340                 345                 350

Val Ser Pro Ser Pro Thr Thr Tyr Arg Met Phe Arg Asp Lys Ser Arg
```

-continued

```
                355                 360                 365
Ser Pro Ser Gln Asn Ser Gln Gln Ser Phe Asp Ser Ser Pro Pro
        370                 375                 380
Thr Pro Gln Cys His Lys Arg His Arg His Cys Pro Val Val Val Ser
385                 390                 395                 400
Glu Ala Thr Ile Val Gly Val Arg Lys Thr Gly Gln Ile Trp Pro Asn
                405                 410                 415
Asp Gly Glu Gly Ala Phe His Gly Asp Ala Asp Gly Ser Phe Gly Thr
                    420                 425                 430
Pro Pro Gly Tyr Gly Cys Ala Ala Asp Arg Ala Glu Glu Gln Arg Arg
            435                 440                 445
His Gln Asp Gly Leu Pro Tyr Ile Asp Asp Ser Pro Ser Ser Ser Pro
        450                 455                 460
His Leu Ser Ser Lys Gly Arg Gly Ser Arg Asp Ala Leu Val Ser Gly
465                 470                 475                 480
Ala Leu Glu Ser Thr Lys Ala Ser Glu Leu Asp Leu Glu Lys Gly Leu
                    485                 490                 495
Glu Met Arg Lys Trp Val Leu Ser Gly Ile Leu Ala Ser Glu Glu Thr
                500                 505                 510
Tyr Leu Ser His Leu Glu Ala Leu Leu Leu Pro Met Lys Pro Leu Lys
            515                 520                 525
Ala Ala Ala Thr Thr Ser Gln Pro Val Leu Thr Ser Gln Gln Ile Glu
        530                 535                 540
Thr Ile Phe Phe Lys Val Pro Glu Leu Tyr Glu Ile His Lys Glu Phe
545                 550                 555                 560
Tyr Asp Gly Leu Phe Pro Arg Val Gln Gln Trp Ser His Gln Gln Arg
                    565                 570                 575
Val Gly Asp Leu Phe Gln Lys Leu Ala Ser Gln Leu Gly Val Tyr Arg
                580                 585                 590
Val Leu Gly Tyr Asn His Asn Gly Glu Trp Cys Glu Ala Gln Thr Lys
            595                 600                 605
Asn Gly Gln Gly Trp Val Pro Ser Asn Tyr Ile Thr Pro Val Asn Ser
        610                 615                 620
Leu Glu Lys His Ser Trp Tyr His Gly Pro Val Ser Arg Asn Ala Ala
625                 630                 635                 640
Glu Tyr Leu Leu Ser Ser Gly Ile Asn Gly Ser Phe Leu Val Arg Glu
                    645                 650                 655
Ser Glu Ser Ser Pro Gly Gln Arg Ser Ile Ser Leu Arg Tyr Glu Gly
                660                 665                 670
Arg Val Tyr His Tyr Arg Ile Asn Thr Ala Ser Asp Gly Lys Leu Tyr
            675                 680                 685
Val Ser Ser Glu Ser Arg Phe Asn Thr Leu Ala Glu Leu Val His His
        690                 695                 700
His Ser Thr Val Ala Asp Gly Leu Ile Thr Thr Leu His Tyr Pro Ala
705                 710                 715                 720
Pro Lys Arg Asn Lys Pro Thr Val Tyr Gly Val Ser Pro Asn Tyr Asp
                    725                 730                 735
Lys Trp Glu Met Glu Arg Thr Asp Ile Thr Met Lys His Lys Leu Gly
                740                 745                 750
Gly Gly Gln Tyr Gly Glu Val Tyr Glu Gly Val Trp Lys Lys Tyr Ser
            755                 760                 765
Leu Thr Val Ala Val Lys Thr Leu Lys Glu Asp Thr Met Glu Val Glu
        770                 775                 780
```

Glu Phe Leu Lys Glu Ala Ala Val Met Lys Glu Ile Lys His Pro Asn
785                 790                 795                 800

Leu Val Gln Leu Leu Gly Val Cys Thr Arg Glu Pro Pro Phe Tyr Ile
            805                 810                 815

Ile Thr Glu Phe Met Thr Tyr Gly Asn Leu Leu Asp Tyr Leu Arg Glu
        820                 825                 830

Cys Asn Arg Gln Glu Val Asn Ala Val Val Leu Leu Tyr Met Ala Thr
            835                 840                 845

Gln Ile Ser Ser Ala Met Glu Tyr Leu Glu Lys Lys Asn Phe Ile His
850                 855                 860

Arg Ser Cys Cys Pro Lys Leu Pro Gly Arg Gly Glu Pro Leu Gly Glu
865                 870                 875                 880

Gly Ser

<210> SEQ ID NO 10
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Ser Ser Ala Met Glu Tyr Leu Glu Lys Lys Asn Phe Ile His Arg Ser
1               5                   10                  15

Cys Cys Pro Lys Leu Pro Gly Arg Gly Glu Pro Leu Gly Glu Gly Ser
            20                  25                  30

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ser Cys Cys Pro Lys Leu Pro Gly Arg Gly Glu Pro Leu Gly Glu Gly
1               5                   10                  15

Ser

<210> SEQ ID NO 12
<211> LENGTH: 4906
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
atggtggacc cggtgggctt cgcggaggcg tggaaggcgc agttcccgga ctcagagccc      60
ccgcgcatgg agctgcgctc agtgggcgac atcgagcagg agctggagcg ctgcaaggcc     120
tccattcggc gcctggagca ggaggtgaac caggagcgct tccgcatgat ctacctgcag     180
acgttgctgg ccaaggaaaa gaagagctat gaccggcagc gatggggctt ccggcgcgcg     240
gcgcaggccc ccgacggcgc ctccgagccc gagcgtccg cgtcgcgccc gcagccagcg     300
cccgccgacg gagccgaccc ggccgcccgcc gaggagcccg aggccggcc cgacggcgag     360 ggttctccgg gtaaggccag gcccgggacc gcccgcaggc ccggggcagc cgcgtcgggg     420

```
gaacgggacg accgggaccc ccccgccagc gtggcggcgc tcaggtccaa cttcgagcgg    480
atccgcaagg gccatggcca gcccggggcg gacgccgaga agcccttcta cgtgaacgtc    540
gagtttcacc acgagcgcgg cctggtgaag gtcaacgaca aagaggtgtc ggaccgcatc    600
agctccctgg gcagccaggc catgcagatg gagcgcaaaa agtcccagca cggcgcgggc    660
tcgagcgtgg gggatgcatc caggcccccct taccggggac gctcctcgga gagcagctgc    720
ggcgtcgacg gcgactacga ggacgccgag ttgaaccccc gcttcctgaa ggacaacctg    780
atcgacgcca atggcggtag caggccccct tggccgcccc tggagtacca gccctaccag    840
agcatctacg tcgggggcat gatggaaggg gagggcaagg gcccgctcct gcgcagccag    900
agcacctctg agcaggagaa gcgccttacc tggccccgca ggtcctactc cccccggagt    960
tttgaggatt gcggaggcgg ctataccccg gactgcagct ccaatgagaa cctcacctcc   1020
agcgaggagg acttctcctc tggccagtcc agccgcgtgt ccccaagccc caccacctac   1080
cgcatgttcc gggacaaaag ccgctctccc tcgcagaact cgcaacagtc cttcgacagc   1140
agcagtcccc ccacgccgca gtgccataag cggcaccggc actgcccggt tgtcgtgtcc   1200
gaggccacca tcgtgggcgt ccgcaagacc gggcagatct ggcccaacga tggcgagggc   1260
gccttccatg gagacgcaga tggctcgttc ggaacaccac ctggatacgg ctgcgctgca   1320
gaccgggcag aggagcagcg ccggcaccaa gatgggctgc cctacattga tgactcgccc   1380
tcctcatcgc cccacctcag cagcaagggc aggggcagcc gggatgcgct ggtctcggga   1440
gccctggagt ccactaaagc gagtgagctg gacttggaaa agggcttgga tgagaaaa    1500 tgggtcctgt cgggaatcct ggctagcgag gagacttacc tgagccacct ggaggcactg   1560
ctgctgccca tgaagccttt gaaagccgct gccaccacct tcagccggt gctgacgagt   1620 cagcagatcg agaccatctt cttcaaagtg cctgagctct acgagatcca aaggagttc    1680 tatgatgggc tcttcccccg cgtgcagcag tggagccacc agcagcgggt gggcgaccc    1740 ttccagaagc tggccagcca gctgggtgtg taccgggtct taggctataa tcacaatggg   1800
gaatggtgtg aagcccaaac caaaaatggc caaggctggg tcccaagcaa ctacatcacg   1860
ccagtcaaca gtctggagaa acactcctgg taccatgggc ctgtgtcccg caatgccgct   1920
gagtatctgc tgagcagcgg gatcaatggc agcttcttgg tgcgtgagag tgagagcagt   1980
cctggccaga ggtccatctc gctgagatac gaagggaggg tgtaccatta caggatcaac   2040
actgcttctg atggcaagct ctacgtctcc tccgagagcc gcttcaacac cctggccgag   2100
ttggttcatc atcattcaac ggtggccgac gggctcatca ccacgctcca ttatccagcc   2160
ccaaagcgca caagcccac tgtctatggt gtgtcccca actacgacaa gtgggagatg   2220
gaacgcacgg acatcaccat gaagcacaag ctgggcgggg gccagtacgg ggaggtgtac   2280
gagggcgtgt ggaagaaata cagcctgacg gtggccgtga gaccttgaa ggaggacacc   2340 atggaggtgg aagagttctt gaaagaagct gcagtcatga aagagatcaa acaccctaac   2400
ctggtgcagc tccttggcag gggtctgcac ccggagcccc cgttctata tcatcactga    2460 gttcatgacc tacgggaacc tcctggacta cctgagggag tgcaaccggc aggaggtgaa   2520
cgccgtggtc tgctgtgtaca tggccactca gatctcgtca gccatggagt acctggagaa   2580
gaaaaacttc atccacagag atcttgctgc ccgaaactgc ctggtagggg agaaccactt   2640
ggtgaaggta gctgattttg gcctgagcag gttgatgaca ggacacct acacagccca    2700 tgctggagcc aagttcccca tcaaatgac tgcaccgag agcctggcct acaacaagtt    2760
ctccatcaag tccgacgtct gggcatttgg agtattgctt tgggaaattg ctacctatgg   2820
```

```
catgtccct  tacccgggaa  ttgacctgtc  ccaggtgtat  gagctgctag  agaaggacta     2880
ccgcatggag  cgcccagaag  gctgcccaga  gaaggtctat  gaactcatgc  gagcatgttg     2940
gcagtggaat  ccctctgacc  ggccctcctt  tgctgaaatc  caccaagcct  ttgaaacaat     3000
gttccaggaa  tccagtatct  cagacgaagt  ggaaaaggag  ctggggaaac  aaggcgtccg     3060
tggggctgtg  agtaccttgc  tgcaggcccc  agagctgccc  accaagacga  ggacctccag     3120
gagagctgca  gagcacagag  acaccactga  cgtgcctgag  atgcctcact  ccaagggcca     3180
gggagagagc  gatcctctgg  accatgagcc  tgccgtgtct  ccattgctcc  ctcgaaaaga     3240
gcgaggtccc  ccggagggcg  gcctgaatga  agatgagcgc  cttctcccca  aagacaaaaa     3300
gaccaacttg  ttcagcgcct  tgatcaagaa  gaagaagaag  acagccccaa  cccctcccaa     3360
acgcagcagc  tccttccggg  agatggacgg  ccagccggag  cgcagagggg  ccggcgagga     3420
agccagaggg  ccgagacatc  agcaacgggg  cactggcttt  cacccccttg  acacagctg     3480 acccaagtcc  ccaaagccca  gcaatggggc  tgggtcccc  aatggagccc  tccgggagtc     3540
cgggggctca  ggcttccggt  ctccccacct  gtggaagaag  tccagcacgc  tgaccagcag     3600
ccgcctagcc  accggcgagg  aggagggcgg  tggcagctcc  agcaagcgct  tcctgcgctc     3660
ttgctccgcc  tcctgcgttc  cccatggggc  caaggacacg  gagtggaggt  cagtcacgct     3720
gcctcgggac  ttgcagtcca  cgggaagaca  gtttgactcg  tccacatttg  gagggcacaa     3780
aagtgagaag  ccggctctgc  ctcggaagag  ggcaggggag  aacaggtctg  accaggtgac     3840
ccgaggcaca  gtaacgcctc  cccccaggct  ggtgaaaaag  aatgaggaag  ctgctgatga     3900
ggtcttcaaa  gacatcatgg  agtccagccc  gggctccagc  ccgcccaacc  tgactccaaa     3960
acccctccgg  cggcaggtca  ccgtggcccc  tgcctcgggc  ctcccccaca  aggaagaagc     4020
tggaaagggc  agtgccttag  ggaccctgc  tgcagctgag  ccagtgaccc  ccaccagcaa     4080
agcaggctca  ggtgcaccag  ggggcaccag  caagggcccc  gccgaggagt  ccagagtgag     4140
gaggcacaag  cactcctctg  agtcgccagg  gagggacaag  gggaaattgt  ccaggctcaa     4200
acctgccccg  ccgcccccac  cagcagcctc  tgcaggaag  gctggaggaa  agccctcgca     4260
gagcccgagc  caggaggcgg  ccggggaggc  agtcctgggc  gcaaagacaa  aagccacgag     4320
tctggttgat  gctgtgaaca  gtgacgctgc  caagcccagc  cagccgggag  agggcctcaa     4380
aaagcccgtg  ctcccggcca  ctccaaagcc  acagtccgcc  aagccgtcgg  ggacccccat     4440
cagcccagcc  ccgttccct  ccacgttgcc  atcagcatcc  tcggccctgg  cagggacca      4500 gccgtcttcc  accgccttca  tccctctcat  atcaaccga  gtgtctcttc  ggaaaacccg     4560
ccagcctcca  gagcggatcg  ccagcggcgc  catcaccaag  ggcgtggtcc  tggacagcac     4620
cgaggcgctg  tgcctcgcca  tctctaggaa  ctccgagcag  atggcagcc  acagcgcagt     4680 gctggaggcc  ggcaaaaacc  tctacacgtt  ctgcgtgagc  tatgtggatt  ccatccagca     4740
aatgaggaac  aagtttgcct  tccgagaggc  catcaacaaa  ctgagaata  atctccggga     4800 gcttcagatc  tgcccggcga  cagcaggcag  tggtccggcg  gccactcagg  acttcagcaa     4860
gctcctcagt  tcggtgaagg  aaatcagtga  catagtgcag  aggtag                     4906
```

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 13
ctggtgcagc tccttggcag gggtctgcac                                              30

<210> SEQ ID NO 14
<211> LENGTH: 819
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Met Val Asp Pro Val Gly Phe Ala Glu Ala Trp Lys Ala Gln Phe Pro
1               5                   10                  15

Asp Ser Glu Pro Pro Arg Met Glu Leu Arg Ser Val Gly Asp Ile Glu
            20                  25                  30

Gln Glu Leu Glu Arg Cys Lys Ala Ser Ile Arg Arg Leu Glu Gln Glu
        35                  40                  45

Val Asn Gln Glu Arg Phe Arg Met Ile Tyr Leu Gln Thr Leu Leu Ala
    50                  55                  60

Lys Glu Lys Lys Ser Tyr Asp Arg Gln Arg Trp Gly Phe Arg Arg Ala
65                  70                  75                  80

Ala Gln Ala Pro Asp Gly Ala Ser Glu Pro Arg Ala Ser Ala Ser Arg
                85                  90                  95

Pro Gln Pro Ala Pro Ala Asp Gly Ala Asp Pro Pro Ala Glu Glu
            100                 105                 110

Pro Glu Ala Arg Pro Asp Gly Glu Gly Ser Pro Gly Lys Ala Arg Pro
        115                 120                 125

Gly Thr Ala Arg Arg Pro Gly Ala Ala Ala Ser Gly Glu Arg Asp Asp
130                 135                 140

Arg Gly Pro Pro Ala Ser Val Ala Ala Leu Arg Ser Asn Phe Glu Arg
145                 150                 155                 160

Ile Arg Lys Gly His Gly Gln Pro Gly Ala Asp Ala Glu Lys Pro Phe
                165                 170                 175

Tyr Val Asn Val Glu Phe His His Glu Arg Gly Leu Val Lys Val Asn
            180                 185                 190

Asp Lys Glu Val Ser Asp Arg Ile Ser Ser Leu Gly Ser Gln Ala Met
        195                 200                 205

Gln Met Glu Arg Lys Lys Ser Gln His Gly Ala Gly Ser Ser Val Gly
    210                 215                 220

Asp Ala Ser Arg Pro Pro Tyr Arg Gly Arg Ser Ser Glu Ser Ser Cys
225                 230                 235                 240

Gly Val Asp Gly Asp Tyr Glu Asp Ala Glu Leu Asn Pro Arg Phe Leu
                245                 250                 255

Lys Asp Asn Leu Ile Asp Ala Asn Gly Gly Ser Arg Pro Pro Trp Pro
            260                 265                 270

Pro Leu Glu Tyr Gln Pro Tyr Gln Ser Ile Tyr Val Gly Gly Met Met
        275                 280                 285

Glu Gly Glu Gly Lys Gly Pro Leu Leu Arg Ser Gln Ser Thr Ser Glu
    290                 295                 300

Gln Glu Lys Arg Leu Thr Trp Pro Arg Arg Ser Tyr Ser Pro Arg Ser
305                 310                 315                 320

Phe Glu Asp Cys Gly Gly Gly Tyr Thr Pro Asp Cys Ser Ser Asn Glu
                325                 330                 335
```

```
Asn Leu Thr Ser Ser Glu Glu Asp Phe Ser Ser Gly Gln Ser Ser Arg
            340                 345                 350

Val Ser Pro Ser Pro Thr Thr Tyr Arg Met Phe Arg Asp Lys Ser Arg
        355                 360                 365

Ser Pro Ser Gln Asn Ser Gln Gln Ser Phe Asp Ser Ser Ser Pro Pro
        370                 375                 380

Thr Pro Gln Cys His Lys Arg His Arg His Cys Pro Val Val Val Ser
385                 390                 395                 400

Glu Ala Thr Ile Val Gly Val Arg Lys Thr Gly Gln Ile Trp Pro Asn
                405                 410                 415

Asp Gly Glu Gly Ala Phe His Gly Asp Ala Asp Gly Ser Phe Gly Thr
            420                 425                 430

Pro Pro Gly Tyr Gly Cys Ala Ala Asp Arg Ala Glu Glu Gln Arg Arg
            435                 440                 445

His Gln Asp Gly Leu Pro Tyr Ile Asp Asp Ser Pro Ser Ser Ser Pro
        450                 455                 460

His Leu Ser Ser Lys Gly Arg Gly Ser Arg Asp Ala Leu Val Ser Gly
465                 470                 475                 480

Ala Leu Glu Ser Thr Lys Ala Ser Glu Leu Asp Leu Glu Lys Gly Leu
                485                 490                 495

Glu Met Arg Lys Trp Val Leu Ser Gly Ile Leu Ala Ser Glu Glu Thr
            500                 505                 510

Tyr Leu Ser His Leu Glu Ala Leu Leu Leu Pro Met Lys Pro Leu Lys
        515                 520                 525

Ala Ala Ala Thr Thr Ser Gln Pro Val Leu Thr Ser Gln Gln Ile Glu
530                 535                 540

Thr Ile Phe Phe Lys Val Pro Glu Leu Tyr Glu Ile His Lys Glu Phe
545                 550                 555                 560

Tyr Asp Gly Leu Phe Pro Arg Val Gln Gln Trp Ser His Gln Gln Arg
                565                 570                 575

Val Gly Asp Leu Phe Gln Lys Leu Ala Ser Gln Leu Gly Val Tyr Arg
            580                 585                 590

Val Leu Gly Tyr Asn His Asn Gly Glu Trp Cys Glu Ala Gln Thr Lys
        595                 600                 605

Asn Gly Gln Gly Trp Val Pro Ser Asn Tyr Ile Thr Pro Val Asn Ser
        610                 615                 620

Leu Glu Lys His Ser Trp Tyr His Gly Pro Val Ser Arg Asn Ala Ala
625                 630                 635                 640

Glu Tyr Leu Leu Ser Ser Gly Ile Asn Gly Ser Phe Leu Val Arg Glu
                645                 650                 655

Ser Glu Ser Ser Pro Gly Gln Arg Ser Ile Ser Leu Arg Tyr Glu Gly
            660                 665                 670

Arg Val Tyr His Tyr Arg Ile Asn Thr Ala Ser Asp Gly Lys Leu Tyr
        675                 680                 685

Val Ser Ser Glu Ser Arg Phe Asn Thr Leu Ala Glu Leu Val His His
        690                 695                 700

His Ser Thr Val Ala Asp Gly Leu Ile Thr Thr Leu His Tyr Pro Ala
705                 710                 715                 720

Pro Lys Arg Asn Lys Pro Thr Val Tyr Gly Val Ser Pro Asn Tyr Asp
                725                 730                 735

Lys Trp Glu Met Glu Arg Thr Asp Ile Thr Met Lys His Lys Leu Gly
            740                 745                 750

Gly Gly Gln Tyr Gly Glu Val Tyr Glu Gly Val Trp Lys Lys Tyr Ser
```

```
                755                 760                 765
Leu Thr Val Ala Val Lys Thr Leu Lys Glu Asp Thr Met Glu Val Glu
        770                 775                 780

Glu Phe Leu Lys Glu Ala Ala Val Met Lys Glu Ile Lys His Pro Asn
785                 790                 795                 800

Leu Val Gln Leu Leu Gly Arg Gly Leu His Pro Gly Ala Pro Val Leu
                805                 810                 815

Tyr His His

<210> SEQ ID NO 15
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Val Met Lys Glu Ile Lys His Pro Asn Leu Val Gln Leu Leu Gly
1               5                   10                  15

Arg Gly Leu His Pro Gly Ala Pro Val Leu Tyr His His
            20                  25

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Gly Leu His Pro Gly Ala Pro Val Leu Tyr His His
1               5                   10

<210> SEQ ID NO 17
<211> LENGTH: 4902
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
atggtggacc cggtgggctt cgcggaggcg tggaaggcgc agttcccgga ctcagagccc      60
ccgcgcatgg agctgcgctc agtgggcgac atcgagcagg agctggagcg ctgcaaggcc     120
tccattcggc gcctggagca ggaggtgaac caggagcgct tccgcatgat ctacctgcag     180
acgttgctgg ccaaggaaaa gaagagctat gaccggcagc gatggggctt ccggcgcgcg     240
gcgcaggccc ccgacggcgc ctccgagccc cgagcgtccg cgtcgcgccc gcagccagcg     300
cccgccgacg gagccgaccc gccgcccgcc gaggagcccg aggcccggcc cgacggcgag     360
ggttctccgg gtaaggccag gcccgggacc gcccgcaggc ccggggcagc cgcgtcgggg     420
gaacgggacg accggggacc ccccgccagc gtggcggcgc tcaggtccaa cttcgagcgg     480
atccgcaagg ccatggcca gcccggggcg gacgccgaga gcccttcta cgtgaacgtc     540 gagtttcacc acgagcgcgg cctggtgaag gtcaacgaca agaggtgtc ggaccgcatc     600 agctccctgg gcagccaggc catgcagatg gagcgcaaaa agtccagca cggcgcgggc     660 tcgagcgtgg gggatgcatc caggcccct taccggggac gctcctcgga gagcagctgc     720
```

-continued

```
ggcgtcgacg gcgactacga ggacgccgag ttgaaccccc gcttcctgaa ggacaacctg    780
atcgacgcca atggcggtag caggcccccect tggccgcccc tggagtacca gccctaccag    840
agcatctacg tcggggggcat gatggaaggg gagggcaagg gcccgctcct gcgcagccag    900
agcacctctg agcaggagaa gcgccttacc tggccccgca ggtcctactc cccccggagt    960
tttgaggatt gcggaggcgg ctataccccg gactgcagct ccaatgagaa cctcacctcc    1020
agcgaggagg acttctcctc tggccagtcc agcgcgtgt ccccaagccc caccacctac    1080
cgcatgttcc gggacaaaag ccgctctccc tcgcagaact cgcaacagtc cttcgacagc    1140
agcagtcccc ccacgccgca gtgccataag cggcaccggc actgcccggt tgtcgtgtcc    1200
gaggccacca tcgtgggcgt ccgcaagacc gggcagatct ggcccaacga tggcgagggc    1260
gccttccatg gagacgcaga tggctcgttc ggaacaccac ctggatacgg ctgcgctgca    1320 gacccgggcag aggagcagcg ccggcaccaa gatgggctgc cctacattga tgactcgccc    1380
tcctcatcgc cccacctcag cagcaagggc aggggcagcc gggatgcgct ggtctcggga    1440
gccctggagt ccactaaagc gagtgagctg gacttggaaa agggcttgga gatgagaaaa    1500
tgggtcctgt cgggaatcct ggctagcgag gagacttacc tgagccacct ggaggcactg    1560
ctgctgccca tgaagccttt gaaagccgct gccaccacct ctcagccggt gctgacgagt    1620
cagcagatcg agaccatctt cttcaaagtg cctgagctct acgagatcca caggagttc    1680 tatgatgggc tcttccccccg cgtgcagcag tggagccacc agcagcgggt gggcgacctc    1740
ttccagaagc tggccagcca gctgggtgtg taccgggtct taggctataa tcacaatggg    1800
gaatggtgtg aagcccaaac caaaatggc caaggctggg tcccaagcaa ctacatcacg    1860
ccagtcaaca gtctggagaa acactcctgg taccatgggc ctgtgtcccg caatgccgct    1920
gagtatctgc tgagcagcgg gatcaatggc agcttcttgg tgcgtgagag tgagagcagt    1980
cctggccaga ggtccatctc gctgagatac gaagggaggg tgtaccatta caggatcaac    2040
actgcttctg atggcaagct ctacgtctcc tccgagagcc gcttcaacac cctgccgag    2100 ttggttcatc atcattcaac ggtggccgac gggctcatca ccacgctcca ttatccagcc    2160
ccaaagcgca caagcccac tgtctatggt gtgtcccca actacgacaa gtgggagatg    2220
gaacgcacgg acatcaccat gaagcacaag ctgggcgggg gccagtacgg ggaggtgtac    2280
gagggcgtgt ggaagaaata cagcctgacg gtggccgtga agaccttgaa ggaggacacc    2340
atggaggtgg aagagttctt gaaagaagct gcagtcatga aagagatcaa acaccctaac    2400
ctggtgcagc tccttgggt ctgcaccccgg gagcccccgt tctatatcat cactgagttc    2460
atgacctacg ggaacctcct ggactacctg agggagtgca accggtagga ggtgaacgcc    2520
gtggtgctgc tgtacatggc cactcagatc tcgtcagcca tggagtacct ggagaagaaa    2580
aacttcatcc acagagatct tgctgcccga aactgcctgg taggggagaa ccacttggtg    2640
aaggtagctg atttttggcct gagcaggttg atgacagggg acacctacac agcccatgct    2700
ggagccaagt tccccatcaa atggactgca cccgagagcc tggcctacaa caagttctcc    2760
atcaagtccg acgtctgggc atttggagta ttgctttggg aaattgctac ctatggcatg    2820
tccccttacc cgggaattga cctgtcccag gtgtatgagc tgctagagaa ggactaccgc    2880
atggagcgcc cagaaggctg cccagagaag gtctatgaac tcatgcgagc atgttggcag    2940
tggaatccct ctgaccggcc ctcctttgct gaaatccacc aagcctttga aacaatgttc    3000
caggaatcca gtatctcaga cgaagtggaa aaggagctgg ggaaacaagg cgtccgtggg    3060
gctgtgagta ccttgctgca ggccccagag ctgcccacca agacgaggac ctccaggaga    3120
```

```
gctgcagagc acagagacac cactgacgtg cctgagatgc ctcactccaa gggccaggga    3180
gagagcgatc ctctggacca tgagcctgcc gtgtctccat tgctccctcg aaaagagcga    3240
ggtcccccgg agggcggcct gaatgaagat gagcgccttc tccccaaaga caaaagacc     3300 aacttgttca gcgccttgat caagaagaag aagaagacag ccccaacccc tcccaaacgc    3360
agcagctcct tccgggagat ggacggccag ccggagcgca gagggccgg cgaggaagag     3420 ggccgagaca tcagcaacgg ggcactggct ttcacccct tggacacagc tgacccagcc     3480
aagtccccaa agcccagcaa tggggctggg gtccccaatg gagccctccg ggagtccggg    3540
ggctcaggct tccggtctcc ccacctgtgg aagaagtcca gcacgctgac cagcagccgc    3600
ctagccaccg gcgaggagga gggcggtggc agctccagca gcgcttcct gcgctcttgc     3660 tccgcctcct gcgttcccca tggggccaag gacacggagt ggaggtcagt cacgctgcct    3720
cgggacttgc agtccacggg aagacagttt gactcgtcca catttggagg gcacaaaagt    3780
gagaagccgg ctctgcctcg gaagagggca ggggagaaca ggtctgacca ggtgacccga    3840
ggcacagtaa cgcctccccc caggctggtg aaaaagaatg aggaagctgc tgatgaggtc    3900
ttcaaagaca tcatggagtc cagcccgggc tccagcccgc ccaacctgac tccaaacccc    3960
ctccggcggc aggtcaccgt ggcccctgcc tcgggcctcc cccacaagga agaagctgga    4020
aagggcagtg cctagggac ccctgctgca gctgagccag tgaccccccac cagcaaagca     4080 ggctcaggtg caccagggg caccagcaag ggccccgccg aggagtccag agtgaggagg      4140
cacaagcact cctctgagtc gccagggagg acaaggggga aattgtccag gctcaaacct    4200
gccccgccgc ccccaccagc agcctctgca gggaaggctg gaggaaagcc ctcgcagagc    4260
ccgagccagg aggcggccgg ggaggcagtc ctgggcgcaa agacaaaagc cacgagtctg    4320
gttgatgctg tgaacagtga cgctgccaag cccagccagc cgggagaggg cctcaaaaag    4380
cccgtgctcc cggccactcc aaagccacag tccgccaagc cgtcgggac ccccatcagc      4440 ccagccccg ttccctccac gttgccatca gcatcctcgg ccctggcagg ggaccagccg      4500
tcttccaccg ccttcatccc tctcatatca acccgagtgt ctcttcggaa aaccccgccag   4560 cctccagagc ggatcgccag cggcgccatc accaagggcg tggtcctgga cagcaccgag    4620
gcgctgtgcc tcgccatctc taggaactcc gagcagatgg ccagccacag cgcagtgctg    4680
gaggccggca aaaacctcta cacgttctgc gtgagctatg tggattccat ccagcaaatg    4740
aggaacaagt ttgccttccg agaggccatc aacaaactgg agaataatct ccgggagctt    4800
cagatctgcc cggcgacagc aggcagtggt ccggcggcca ctcaggactt cagcaagctc    4860
ctcagttcgg tgaaggaaat cagtgacata gtgcagaggt ag                       4902
```

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 18
agggagtgca accggtagga ggtgaacgcc                                     30

<210> SEQ ID NO 19
<211> LENGTH: 835
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Val Asp Pro Val Gly Phe Ala Glu Ala Trp Lys Ala Gln Phe Pro
1               5                   10                  15

Asp Ser Glu Pro Pro Arg Met Glu Leu Arg Ser Val Gly Asp Ile Glu
            20                  25                  30

Gln Glu Leu Glu Arg Cys Lys Ala Ser Ile Arg Arg Leu Glu Gln Glu
        35                  40                  45

Val Asn Gln Glu Arg Phe Arg Met Ile Tyr Leu Gln Thr Leu Leu Ala
    50                  55                  60

Lys Glu Lys Lys Ser Tyr Asp Arg Gln Arg Trp Gly Phe Arg Arg Ala
65                  70                  75                  80

Ala Gln Ala Pro Asp Gly Ala Ser Glu Pro Arg Ala Ser Ala Ser Arg
                85                  90                  95

Pro Gln Pro Ala Pro Ala Asp Gly Ala Asp Pro Pro Ala Glu Glu
            100                 105                 110

Pro Glu Ala Arg Pro Asp Gly Glu Gly Ser Pro Gly Lys Ala Arg Pro
            115                 120                 125

Gly Thr Ala Arg Arg Pro Gly Ala Ala Ser Gly Glu Arg Asp Asp
130                 135                 140

Arg Gly Pro Pro Ala Ser Val Ala Ala Leu Arg Ser Asn Phe Glu Arg
145                 150                 155                 160

Ile Arg Lys Gly His Gly Gln Pro Gly Ala Asp Ala Glu Lys Pro Phe
                165                 170                 175

Tyr Val Asn Val Glu Phe His His Glu Arg Gly Leu Val Lys Val Asn
            180                 185                 190

Asp Lys Glu Val Ser Asp Arg Ile Ser Ser Leu Gly Ser Gln Ala Met
        195                 200                 205

Gln Met Glu Arg Lys Lys Ser Gln His Gly Ala Gly Ser Ser Val Gly
    210                 215                 220

Asp Ala Ser Arg Pro Pro Tyr Arg Gly Arg Ser Ser Glu Ser Ser Cys
225                 230                 235                 240

Gly Val Asp Gly Asp Tyr Glu Asp Ala Glu Leu Asn Pro Arg Phe Leu
                245                 250                 255

Lys Asp Asn Leu Ile Asp Ala Asn Gly Gly Ser Arg Pro Pro Trp Pro
            260                 265                 270

Pro Leu Glu Tyr Gln Pro Tyr Gln Ser Ile Tyr Val Gly Gly Met Met
        275                 280                 285

Glu Gly Glu Gly Lys Gly Pro Leu Leu Arg Ser Gln Ser Thr Ser Glu
    290                 295                 300

Gln Glu Lys Arg Leu Thr Trp Pro Arg Arg Ser Tyr Ser Pro Arg Ser
305                 310                 315                 320

Phe Glu Asp Cys Gly Gly Gly Tyr Thr Pro Asp Cys Ser Ser Asn Glu
                325                 330                 335

Asn Leu Thr Ser Ser Glu Glu Asp Phe Ser Ser Gly Gln Ser Ser Arg
            340                 345                 350

Val Ser Pro Ser Pro Thr Thr Tyr Arg Met Phe Arg Asp Lys Ser Arg
        355                 360                 365

Ser Pro Ser Gln Asn Ser Gln Gln Ser Phe Asp Ser Ser Ser Pro Pro
370                 375                 380

Thr Pro Gln Cys His Lys Arg His Arg His Cys Pro Val Val Val Ser

```
            385                 390                 395                 400
Glu Ala Thr Ile Val Gly Val Arg Lys Thr Gly Gln Ile Trp Pro Asn
                    405                 410                 415

Asp Gly Glu Gly Ala Phe His Gly Asp Ala Asp Gly Ser Phe Gly Thr
                420                 425                 430

Pro Pro Gly Tyr Gly Cys Ala Ala Asp Arg Ala Glu Gln Arg Arg
            435                 440                 445

His Gln Asp Gly Leu Pro Tyr Ile Asp Ser Pro Ser Ser Ser Pro
        450                 455                 460

His Leu Ser Ser Lys Gly Arg Gly Ser Arg Asp Ala Leu Val Ser Gly
465                 470                 475                 480

Ala Leu Glu Ser Thr Lys Ala Ser Glu Leu Asp Leu Glu Lys Gly Leu
                485                 490                 495

Glu Met Arg Lys Trp Val Leu Ser Gly Ile Leu Ala Ser Glu Glu Thr
                500                 505                 510

Tyr Leu Ser His Leu Glu Ala Leu Leu Leu Pro Met Lys Pro Leu Lys
            515                 520                 525

Ala Ala Ala Thr Thr Ser Gln Pro Val Leu Thr Ser Gln Gln Ile Glu
        530                 535                 540

Thr Ile Phe Phe Lys Val Pro Glu Leu Tyr Glu Ile His Lys Glu Phe
545                 550                 555                 560

Tyr Asp Gly Leu Phe Pro Arg Val Gln Gln Trp Ser His Gln Gln Arg
                565                 570                 575

Val Gly Asp Leu Phe Gln Lys Leu Ala Ser Gln Leu Gly Val Tyr Arg
                580                 585                 590

Val Leu Gly Tyr Asn His Asn Gly Glu Trp Cys Glu Ala Gln Thr Lys
            595                 600                 605

Asn Gly Gln Gly Trp Val Pro Ser Asn Tyr Ile Thr Pro Val Asn Ser
        610                 615                 620

Leu Glu Lys His Ser Trp Tyr His Gly Pro Val Ser Arg Asn Ala Ala
625                 630                 635                 640

Glu Tyr Leu Leu Ser Ser Gly Ile Asn Gly Ser Phe Leu Val Arg Glu
                645                 650                 655

Ser Glu Ser Ser Pro Gly Gln Arg Ser Ile Ser Leu Arg Tyr Glu Gly
                660                 665                 670

Arg Val Tyr His Tyr Arg Ile Asn Thr Ala Ser Asp Gly Lys Leu Tyr
            675                 680                 685

Val Ser Ser Glu Ser Arg Phe Asn Thr Leu Ala Glu Leu Val His His
        690                 695                 700

His Ser Thr Val Ala Asp Gly Leu Ile Thr Thr Leu His Tyr Pro Ala
705                 710                 715                 720

Pro Lys Arg Asn Lys Pro Thr Val Tyr Gly Val Ser Pro Asn Tyr Asp
                725                 730                 735

Lys Trp Glu Met Glu Arg Thr Asp Ile Thr Met Lys His Lys Leu Gly
                740                 745                 750

Gly Gly Gln Tyr Gly Glu Val Tyr Glu Gly Val Trp Lys Lys Tyr Ser
            755                 760                 765

Leu Thr Val Ala Val Lys Thr Leu Lys Glu Asp Thr Met Glu Val Glu
        770                 775                 780

Glu Phe Leu Lys Glu Ala Ala Val Met Lys Glu Ile Lys His Pro Asn
785                 790                 795                 800

Leu Val Gln Leu Leu Gly Val Cys Thr Arg Glu Pro Pro Phe Tyr Ile
                805                 810                 815
```

Ile Thr Glu Phe Met Thr Tyr Gly Asn Leu Leu Asp Tyr Leu Arg Glu
            820                 825                 830

Cys Asn Arg
        835

<210> SEQ ID NO 20
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ser Ile Trp Ser Ile Ala Leu Gly Asn Cys Tyr Leu Trp His Val Pro
1               5                   10                  15

Leu Pro Gly Asn
            20

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tgaccaactc gtgtgtgaaa ctc                                           23

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tccacttcgt ctgagatact ggatt                                         25

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cgcaacaagc ccactgtct                                                19

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
caagtggttc tcccctacca                                               20

<210> SEQ ID NO 25
<211> LENGTH: 20

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tggtagggga gaaccacttg                                              20

<210> SEQ ID NO 26
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gaaaaactyc atccmcagmr wtykkrstry ysswwwskgm mwkkdmkrss wrwrscaykt   60 ssyswwrsy                                                          69

<210> SEQ ID NO 27
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
cattggagat tgctttggaa attgctacct atggtgcccc ttacc                  45

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
tttttttttt tttttttt                                                18
```

BCR-ABL TRUNCATION MUTATIONS

CROSS-REFERENCE TO RELATED APPLICATION

This application is a continuation of U.S. patent application Ser. No. 15/342,321, filed Nov. 3, 2016, which is a continuation of U.S. patent application Ser. No. 12/892,679, filed Sep. 28, 2010, now U.S. Pat. No. 9,488,656, which claims the benefit of U.S. Provisional Application 61/247,390 filed on Sep. 30, 2009 both of which are hereby incorporated by reference in their entirety.

The instant application contains a Sequence Listing which has been submitted in ASCII format via EFS-WEB and is hereby incorporated by reference in its entirety. Said ASCII copy, created on Sep. 27, 2018, is named sequence.txt and is 80 KB.

FIELD OF THE INVENTION

The present inventions relate to BCR-ABL variants and resistance to kinase inhibitor therapy.

BACKGROUND OF THE INVENTION

The following description is provided to assist the understanding of the reader. None of the information provided or references cited is admitted to be prior art to the present invention.

Myeloproliferative diseases such as Chronic Myelogenous Leukemia (CML), Acute Myelogenous Leukemia (AML) and Acute Lymphoblastic Leukemia (ALL) are associated with a specific chromosomal abnormality called Philadelphia chromosome. The genetic defect is caused by the reciprocal translocation designated t(9;22)(q34;q11), which refers to an exchange of genetic material between region q34 of chromosome 9 and region q11 of chromosome 22 (Rowley, J. D. Nature. 1973; 243: 290-3; Kurzrock et al. N. Engl. J. Med. 1988; 319: 990-998). This translocation results in a portion of the BCR ("breakpoint cluster region") gene from chromosome 22 (region q11) becoming fused with a portion of the ABL gene from chromosome 9 (region q34).

The fused "BCR-ABL" gene is located on chromosome 22, in which both BCR and ABL genes are shortened as a result of the translocation. The fused gene retains the tyrosine kinase domain of the ABL gene, which is constitutively active (Elefanty et al. EMBO J. 1990; 9: 1069-1078). This kinase activity activates various signal transduction pathways leading to uncontrolled cell growth and division (e.g., by promoting cell proliferation and inhibiting apoptosis). For example, BCR-ABL may cause undifferentiated blood cells to proliferate and fail to mature.

Treatment of myeloproliferative diseases may involve drug therapy (e.g., chemotherapy), bone marrow transplants, or a combination. Protein kinase inhibitors such as "imatinib mesylate" (also known as STI571 or 2-phenylaminopyrimidine or "imantinib" for short; marketed as a drug under the trade name "Gleevec" or "Glivec") have proven effective for treating CML (Deininger et al., Blood. 1997; 90: 3691-3698; Manley, P. W., Eur. J. Cancer. 2002; 38: S19-S27). Imatinib is an ATP competitive inhibitor of TYROSINE KINASE activity and functions by binding to the kinase domain of BCR-ABL and stabilizing the protein in its closed, inactive conformation. Monotherapy with imatinib has been shown to be effective for all stages of CML. Other kinase inhibitor drugs for treating myeloproliferative diseases include Nilotinib, Dasatinib, Bosutinib (SKI-606) and Aurora kinase inhibitor VX-680.

Resistance to imatinib remains a major problem in the management of patients with myeloproliferative diseases. Rates at which primary (e.g., failure to achieve any hematologic response) and secondary resistance (e.g., hematologic recurrence) occurs varies with the stage of diseases. Primary resistance has been reported in chronic-, accelerated-, or blast-phase at rates of 3%, 9%, and 51%, respectively (Melo, J. V. & Chuah, C. Cancer Lett. 2007; 249: 121-132; Hughes, T. Blood. 2006; 108: 28-37). Secondary resistance has been reported in these patients at rates of 22%, 32%, and 41%, respectively.

Mutations that result in kinase inhibitor resistance include mutations in the kinase domain of the BCR-ABL protein (Mahon, F. X. Blood. 2000; 96: 1070-1079); mutations that disrupt critical contact points between imatinib and the tyrosine kinase receptor or induce a transition from the inactive to the active protein configuration, preventing imatinib binding (Nagar, B. Cell. 2003; 112: 859-871; Nagar et al., Cancer Res. 2002; 62: 4236-4243; Branford S. Blood. 2002; 99: 3472-3475; Branford et al. Blood. 2003; 102: 276-283); the T315I mutation (Gorre et al. Science. 2001; 293: 876-880; Hochhaus et al. Leukemia. 2002; 16: 2190-2196); and P-loop mutations of BCR-ABL (Branford et al. Blood. 2002; 99: 3472-3475; Branford et al. Blood. 2003; 102: 276-283; and Gorre et al. Blood. 2002; 100: 3041-3044) The role of Src family kinases are another possible mechanism for imatinib resistance (Levinson et al., PLoS Biol. 2006; 4: e144). Overexpression and activation of LYN kinase has been implicated in imatinib-resistance (Donato, N. J. Blood. 2003; 101: 690-698).

Chu et al. (N. Engl. J. Med. 2006; 355: 10) report a truncation mutant of BCR-ABL in a CIVIL patient resistant to imatinib. Chu et al. report that the mutant results from a 35 base insertion of ABL intron 8 into the junction between exons 8 and 9, resulting in a new C-terminus and truncation of the normal C-terminus of the ABL portion of the fusion protein. Laudadio et al. (J. Mol. Diag. 2008; 10(2): 177-180) also reports a similar splice variant in CML patients that had undergone imatinib therapy. Guerrasio, et al. (Leukemia Research. 2008; 32: 505-520) report a truncation mutant in patients with imatinib resistance having an alternatively spliced transcript lacking exon 7.

SUMMARY OF THE INVENTION

Provided herein are compositions and methods based on BCR-ABL nucleic acid variants that result in truncation of the BCR-ABL protein and the finding that the BCR-ABL protein variants provide resistance to kinase domain inhibitors such as imatinib. Provided are 4 novel mutations in BCR-ABL nucleic acid: a deletion of nucleotides 2595-2779 (Del 2595-2779), insertion of tetranucleotides CAGG immediately after nucleotide position of 2417 (2417insCAGG), deletion of GA at nucleotide position 2596-2597 (Del 2596-2597), and a substitution of C to T at position 2506(C2506T) corresponding to SEQ ID NO: 1.

An isolated polynucleotide encoding at least a portion of the BCR-ABL nucleic acid in which the polynucleotide encodes the Del 2595-2779 mutation is provided. In one example, the polynucleotide includes a sequence that is substantially identical to SEQ ID NO: 4 over a stretch of 25 contiguous nucleotides. In one example, the sequence of isolated polynucleotide is SEQ ID NO: 3.

The Del 2595-2779 mutation results in a premature "TGA" stop codon at position 2836-2838 of SEQ ID NO: 3. This mutation results in a truncated BCR-ABL protein having new amino acids at the C-terminus. In one example, at least a portion of the truncated BCR-ABL protein is substantially identical to SEQ ID NO: 6 over a stretch of 15 contiguous amino acids. In one example, the truncated protein has the amino acid sequence of SEQ ID NO: 6. In one example, the new C-terminal sequence is SEQ ID NO: 20. In one example, the amino acid sequence of the truncated protein is SEQ ID NO: 5.

An isolated polynucleotide encoding at least a portion of the BCR-ABL nucleic acid in which the polynucleotide encodes the Del 2596-2597 mutation is also provided. In one example, the polynucleotide includes a sequence that is substantially identical to SEQ ID NO: 8 over a stretch of 20 contiguous nucleotides. In one example, the sequence of isolated polynucleotide is SEQ ID NO: 7.

The Del 2596-2597 mutation results in a premature "TGA" stop codon at position 2647-2649 of SEQ ID NO: 7. This mutation results in a truncated BCR-ABL protein having new amino acids at the C-terminus. In one example, at least a portion of the truncated BCR-ABL protein is substantially identical to SEQ ID NO: 10 over a stretch of 20 contiguous amino acids. In one example, the truncated protein has the amino acid sequence of SEQ ID NO: 9. In one example, the new C-terminal sequence is SEQ ID NO: 11.

An isolated polynucleotide encoding at least a portion of the BCR-ABL nucleic acid in which the polynucleotide encodes the 2417insCAGG mutation is also provided. In one example, the polynucleotide includes a sequence that is substantially identical to SEQ ID NO: 13 over a stretch of 20 contiguous nucleotides. In one example, the sequence of isolated polynucleotide is SEQ ID NO: 12.

The 2417insCAGG mutation results in a premature "TGA" stop codon at position 2647-2649 of SEQ ID NO: 12. This mutation results in a truncated BCR-ABL protein having new amino acids at the C-terminus. In one example, at least a portion of the truncated BCR-ABL protein is substantially identical to SEQ ID NO: 15 over a stretch of 20 contiguous amino acids. In one example, the truncated protein has the amino acid sequence of SEQ ID NO: 14. In one example, the new C-terminal amino acid sequence is SEQ ID NO: 16.

An isolated polynucleotide encoding at least a portion of the BCR-ABL nucleic acid in which the polynucleotide encodes the C2506T mutation is also provided. In one example, the polynucleotide includes a sequence that is substantially identical to SEQ ID NO: 18 over a stretch of 20 contiguous nucleotides. In one example, the sequence of isolated polynucleotide is SEQ ID NO: 17.

The C2506T mutation results in a premature "TAG" stop codon at position 2506-2508 of SEQ ID NO: 17. This mutation results in a truncated BCR-ABL protein having new amino acids at the C-terminus. In one example, at least a portion of the truncated BCR-ABL protein is substantially identical to SEQ ID NO: 19. In one example, the truncated protein has the amino acid sequence of SEQ ID NO: 19.

Also provided are methods for detecting the presence or absence of a mutation in BCR-ABL nucleic acid in an individual. The method includes a) providing a sample comprising BCR-ABL nucleic acid from the individual and b) detecting the presence or absence of BCR-ABL nucleic acid comprising all or portions of nucleic acid selected from the group consisting of SEQ ID NO: 4, SEQ ID NO: 8, SEQ ID NO: 13, and SEQ ID NO: 18; in which the presence of a nucleic acid comprising at least one of SEQ ID NO: 4, SEQ ID NO: 8, SEQ ID NO: 13, and SEQ ID NO: 18 is indicative of the presence of at least one of mutations Del 2595-2779, Del 2596-2597, 2417insCAGG and C2506T in BCR-ABL nucleic acid. In one example, detecting the presence of SEQ ID NO: 4 is indicative of the mutation Del 2595-2779 in BCR-ABL nucleic acid. In one example, detecting the presence of SEQ ID NO: 8 is indicative of the mutation Del 2596-2597 in BCR-ABL nucleic acid. In another example, detecting the presence of SEQ ID NO: 13 is indicative of the mutation 2417insCAGG in BCR-ABL nucleic acid. In another example, detecting the presence of SEQ ID NO: 18 is indicative of the mutation C2506T in BCR-ABL nucleic acid. In one example, the method includes sequencing BCR-ABL nucleic acid. In another example, the method includes assessing the size of said BCR-ABL nucleic acid. In one example, the BCR-ABL truncation mutations encode amino acid sequences comprising one or more amino acid sequences selected from the group consisting of SEQ ID NO: 6, SEQ ID NO: 10, SEQ ID NO: 15, and SEQ ID NO: 19.

Also provided are methods for predicting the likelihood for resistance to treatment with a tyrosine kinase inhibitor in a patient diagnosed as having a myeloproliferative disease. In one example, the method includes assessing the BCR-ABL nucleic acid of the patient for the presence or absence of one or more BCR-ABL mutations selected from the group consisting of Del 2595-2779, Del 2596-2597, 2417insCAGG, and C2506T; identifying the patient as having a likelihood of resistance to a tyrosine kinase inhibitor when one or more of the mutations are present. In another example, the method includes assessing a sample from the patient for the presence or absence of one or more BCR-ABL truncation mutant proteins encoded by BCR-ABL nucleic acid having one or more mutations selected from the group consisting of Del 2595-2779, 2417insCAGG, Del 2596-2597, and C2506T; b) identifying the patient as having a likelihood of resistance to a tyrosine kinase inhibitor when one or more of the truncation mutant proteins are present. In one example, the patient is administered with tyrosine kinase inhibitors. Exemplary tyrosine kinase inhibitors include but are not limited to imatinib, nilotinib, and dasatinib. In one example, the treatment regiment of the patient is modified when at least one of the mutations is identified.

Also provided are methods for determining the prognosis of a patient diagnosed as having a myeloproliferative disease. In one example, the method includes a) assessing the BCR-ABL nucleic acid of the patient for the presence or absence of one or more BCR-ABL truncation mutations selected from the group consisting of Del 2595-2779, 2417insCAGG, Del 2596-2597, and C2506T, b) identifying the patient as having poor prognosis when one or more such mutations are present in BCR-ABL nucleic acid relative to an individual without one or more of such mutations in BCR-ABL nucleic acid. In another example, the method includes assessing a sample from the patient for the presence or absence of one or more BCR-ABL truncation mutant proteins encoded by BCR-ABL nucleic acid having one or more mutations selected from the group consisting of Del 2595-2779, 2417insCAGG, Del 2596-2597, and C2506T; b) identifying the patient as having poor prognosis when one or more BCR-ABL truncation mutant proteins are present in the patient's sample relative to an individual without such BCR-ABL truncation mutant proteins.

Also provided are methods for altering the treatment of a patient diagnosed as having a myeloproliferative disease undergoing kinase inhibitor therapy. In one example, the method includes a) assessing the BCR-ABL nucleic acid of the patient for the presence or absence of one or more BCR-ABL truncation mutations selected from the group consisting of Del 2595-2779, 2417insCAGG, Del 2596-2597, and C2506T, b) identifying the patient as resistant to kinase inhibitors when one or more mutations are present, c) altering the treatment of the patient by substituting kinase inhibitors with alternative treatment. In another example, the method includes assessing a sample from the patient for the presence or absence of one or more BCR-ABL truncation mutant proteins encoded by BCR-ABL nucleic acid having one or more mutations in which one or more mutations is selected from the group consisting of Del 2595-2779, Del 2596-2597, 2417insCAGG, C2506T, b) identifying the patient as resistant to kinase inhibitors when one or more of such truncation mutant proteins are present, c) altering the treatment of the patient by substituting kinase inhibitors with alternative treatment. Exemplary alternative treatments include but are not limited to different tyrosine kinase inhibitor, different inhibitor for BCR-ABL (e.g., antibodies specific for BCR-ABL protein), and bone marrow transplant.

In some examples of the above aspects of the invention, the myeloproliferative disease is chronic myelogenous leukemia (CML) or acute lymphoblastic leukemia (ALL). In one example of the above aspects of the invention, the myeloproliferative disease is CIVIL. In another example of the above aspects of the invention, the myeloproliferative disease is ALL. In one example of the above aspects of the invention, the mutation in BCR-ABL nucleic acid is Del 2595-2779. In another example of the above aspects of the invention, the mutation in BCR-ABL nucleic acid is Del 2596-2597. In another example of the above aspects of the invention, the mutation in BCR-ABL nucleic acid is 2417insCAGG. In another example of the above aspects of the invention, the mutation in BCR-ABL nucleic acid is C2506T. In some example s of the above aspects of the invention, the tyrosine kinase inhibitor used in the treatment of a patient diagnosed as having a myeloproliferative disease is one or more selected from the group consisting of imatinib, nilotinib and dasatinib. In one example of the above aspects of the invention, the tyrosine kinase inhibitor is imatinib.

Also provided herein are antibodies that specifically bind to an epitope comprising the new C-terminus of the truncated BCR-ABL protein where the antibody specifically binds to the truncation mutant of BCR-ABL protein (e.g. Del 2595-2779, Del 2596-2597, 2417insCAGG, C2506T) and not to a BCR-ABL protein without such mutation. In one example, the antibody specifically binds to an epitope comprising SEQ ID NO: 11, 16, or 20.

Also provided herein is a vector including a recombinant polynucleotide, in which the recombinant polynucleotide having at least 50 contiguous nucleotides selected from the group consisting of SEQ ID NO: 3, 7, 12, and 17 or their complements. In one example, the polynucleotide is operably linked to an expression regulatory element, in which the expression regulatory element is capable of modulating the expression of said recombinant polynucleotide.

Also provided are genetically modified cells which include a recombinant nucleic acid, in which the recombinant nucleic acid that includes the nucleic acid sequence of the one or more of the BCR-ABL truncation mutations or their complements. In some examples, the genetically modified cells include a recombinant nucleic acid having a nucleotide sequence of SEQ ID NO: 3, SEQ ID NO: 7, SEQ ID NO: 12, or SEQ ID NO: 17. Also included are genetically modified cells that contain vectors comprising the nucleic acid sequences described above. In some examples the recombinant polynucleotide is a cDNA construct while in other examples, the recombinant polynucleotide is genomic construct. In some examples, the genetically modified cells are eukaryotic. In some examples, the recombinant polypeptide has kinase activity.

Also provided are methods of identifying a compound for treating a patient diagnosed as having a myeloproliferative disease, including contacting genetically modified cells with a candidate compound, and assessing the effect of the candidate compound on the cells, in which the candidate compound is identified as a compound for treating a patient with the myeloproliferative disease when the effect of the candidate compound on the genetically modified cells is beneficial in the treatment of the myeloproliferative disease. In some examples, the candidate compound is a protein kinase inhibitor. In some examples, the candidate compound is an inhibitor for BCR-ABL. In some examples, the candidate compound is selected from the group consisting of imatinib, dasatinib, bosutinib, and nilotinib.

In one example, the effect of the compound on the cells is a reduction in the viability or growth rate of the cells or reduction of at least one activity of the expressed recombinant polypeptide. In one example, the effect is a reduction in the viability of the genetically modified cells. In another example, the reduction in viability is reflected by an increase in apoptosis of the genetically modified cells. In one example, the effect is the effect on the kinase activity of the expressed recombinant polypeptide. In one example, the kinase activity is determined by testing the phosphorylation status of a substrate of BCR-ABL. In another example, the effect is a reduction in growth rate of the cells. In one example, the growth rate is measured by the amount of DNA synthesis. In one example, the cells are resistant to imatinib. In one example, the cells are CIVIL cells. In one example, the CIVIL cells are K562 cells.

In some examples, the presence or absence of the polypeptide is determined by assessing the size of the BCR-ABL protein. In another example, the presence or absence of the polypeptide is determined by western blotting. In another example, the presence or absence of the polypeptide is determined by flow cytometry. In some examples, the method simultaneously detects wild-type BCR-ABL protein and the truncation mutant of BCR-ABL protein.

As used herein, the term "subject" or "individual" refers to a human or any other animal that has cells that may contain a BCR-ABL translocation. A subject can be a patient, which refers to a human presenting to a medical provider for diagnosis or treatment of a disease. A human includes pre and post natal forms.

As used herein, the term "patient" refers to one who receives medical care, attention or treatment. As used herein, the term is meant to encompass a person diagnosed with a disease as well as a person who may be symptomatic for a disease but who has not yet been diagnosed.

As used herein, the term "sample" refers to any liquid or solid material obtained from an individual that contains nucleic acids and/or proteins. In preferred examples, a patient sample is obtained from a biological source (i.e., a "biological sample"), such as cells in culture, bodily fluids or a tissue sample from an animal, more preferably, a human. "Bodily fluids" may include, but are not limited to, blood, serum, plasma, saliva, cerebral spinal fluid, pleural fluid, tears, lactal duct fluid, lymph, sputum, urine, amniotic fluid, and semen. A sample may include a bodily fluid that is "acellular." An "acellular bodily fluid" includes less than about 1% (w/w) whole cellular material. Plasma or serum are examples of acellular bodily fluids. A sample may include a specimen of natural or synthetic origin.

As used herein, the term "nucleic acid" or "nucleic acid sequence" refers to an oligonucleotide, nucleotide or polynucleotide, and fragments or portions thereof, which may be single or double stranded, or partially double stranded and represent the sense or antisense strand. A nucleic acid may include DNA or RNA, and may be of natural or synthetic origin and may contain deoxyribonucleotides, ribonucleotides, or nucleotide analogs in any combination. Nucleic acid may comprise a detectable label. Although a sequence of the nucleic acids may be shown in the form of DNA, a person of ordinary skill in the art recognizes that the corresponding RNA sequence will have a similar sequence with the thymine being replaced by uracil i.e. "t" with "u".

Non-limiting examples of nucleic acid include a gene or gene fragment, genomic DNA, exons, introns, mRNA, tRNA, rRNA, ribozymes, cDNA, recombinant nucleic acid, branched nucleic acid, plasmids, vectors, isolated DNA of any sequence, isolated RNA of any sequence, synthetic nucleic acid, nucleic acid probes and primers. Nucleic acid may comprise modified nucleotides, such as methylated nucleotides and nucleotide analogs, uracyl, other sugars and linking groups such as fluororibose and thiolate, and nucleotide branches. A nucleic acid may be modified such as by conjugation, with a labeling component. Other types of modifications included in this definition are caps, substitution of one or more of the naturally occurring nucleotides with an analog, and introduction of chemical entities for attaching the polynucleotide to other molecules such as proteins, metal ions, labeling components, other nucleic acid or a solid support. Nucleic acid may include nucleic acid that has been amplified (e.g., using polymerase chain reaction).

A fragment of a nucleic acid generally contains at least about 15, 20, 25, 30, 35, 40, 45, 50, 75, 100, 200, 300, 400, 500, 1000 nucleotides or more. Larger fragments are possible and may include about 2,000, 2,500, 3,000, 3,500, 4,000, 5,000 7,500, or 10,000 bases.

A fragment of a polypeptide generally contains at least about 5, 10, 15, 20, 25, 30, 35, 40, 45, 50, 75, 100, 200, 300, 400, 500, 1000 amino acids or more. Larger fragments are possible and may include about 1200, 1500 or more amino acids.

As used herein, the term "wild-type" refers to a gene or a gene product that has the characteristics of that gene or gene product when isolated from a naturally occurring source. A wild-type gene is that which is most frequently observed in a population and is thus arbitrarily designated the "normal" or "wild-type" form of the gene. "Wild-type" may also refer to the sequence at a specific nucleotide position or positions, or the sequence at a particular codon position or positions, or the sequence at a particular amino acid position or positions.

As used herein, the term "mutant" or "modified" refers to a gene or gene product which displays modifications in sequence and or functional properties (i.e., altered characteristics) when compared to the wild-type gene or gene product. "Mutant" or "modified" also refers to the sequence at a specific nucleotide position or positions, or the sequence at a particular codon position or positions, or the sequence at a particular amino acid position or positions which displays modifications in sequence and or functional properties (i.e., altered characteristics) when compared to the wild-type gene or gene product.

As used herein, the term "mutation" refers to a nucleic acid with at least a single nucleotide variation relative to the normal sequence or wild-type sequence. In the context of polypeptide, "mutation" refers to at least a single amino acid variation in a polypeptide sequence relative to the normal sequence or wild-type sequence. A mutation may include a substitution, a deletion, an inversion or an insertion. With respect to an encoded polypeptide, a mutation may be "silent" and result in no change in the encoded polypeptide sequence or a mutation may result in a change in the encoded polypeptide sequence. For example, a mutation may result in a substitution in the encoded polypeptide sequence. A mutation may result in a frameshift with respect to the encoded polypeptide sequence.

As used herein, the convention "NTwt###NTmut" is used to indicate a mutation that results in the wild-type nucleotide NTwt at position ### in the nucleic acid being replaced with mutant NTmut. As used herein, the convention "AAwt###AAmut" is used to indicate a mutation that results in the wild-type amino acid AAwt at position ### in the polypeptide being replaced with mutant AAmut.

As used herein, the terms "protein," "peptide," "polypeptide," and "polypeptide fragment" are used interchangeably to refer to polymers of amino acids ("an amino acid sequence") of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation of modification, such as conjugation with a labeling or bioactive component.

As used herein, the terms "identity" and "identical" refer to a degree of identity between sequences. There may be partial identity or complete identity. A partially identical sequence is one that is less than 100% identical to another sequence. Preferably, partially identical sequences have an overall identity of at least 70% or at least 75%, more preferably at least 80% or at least 85%, most preferably at least 90% or at least 95% or at least 99%. Sequence identity determinations may be made for sequences which are not fully aligned. In such instances, the most related segments may be aligned for optimal sequence identity by and the overall sequence identity reduced by a penalty for gaps in the alignment.

The term "substantially identical" in the context of polynucleotides and means at least 65%, at least 70% or at least 75%, at least 80% or at least 85%, at least 90%, at least 95%, at least 99% or identical.

As used herein, the term "insertion" or "addition" refers to a change in an amino acid or nucleotide sequence resulting in the addition of one or more amino acid residues or nucleotides respectively, as compared to the naturally occurring molecule.

As used herein, the term "truncation" refers to a shortening in the amino acid sequence of protein or the nucleotide sequence of a nucleic acid or segment of a nucleic acid (e.g., a gene). A protein truncation may be the result of a truncation in the nucleic acid sequence encoding the protein, a substitution or other mutation that creates a premature stop codon without shortening the nucleic acid sequence, or from alternate splicing of RNA in which a substitution or other mutation that does not itself cause a truncation results in aberrant RNA processing.

As used herein, the term "truncation mutation" or "truncation mutant" in the context of BCR-ABL nucleic acid refers to a BCR-ABL nucleic acid lacking one or more nucleotides relative to the nucleic acid sequence of SEQ ID NO: 1 such that the BCR-ABL protein encoded by the nucleic acid will have truncated C-terminus as compared to SEQ ID NO: 2. Exemplary truncation mutation of BCR-ABL nucleic acid includes but are not limited to Del 2595-2779, Del 2596-2597, 2417insCAGG, and C2506T.

As used herein, the term "truncation mutation" or "truncation mutant" in the context of BCR-ABL protein refers to a BCR-ABL protein with a deletion of one or more amino acids at the C-terminal region of the protein as compared to the exemplary reference BCR-ABL protein amino acid sequence of SEQ ID NO: 2. In preferred examples, such truncation mutation may result from deletion of nucleotides 2595-2779 (Del 2595-2779), insertion of CAGG immediately after nucleotide 2417 (2417insCAGG), GA deletion at position 2596-2597 (Del 2596-2597), and substitution of C to T at nucleotide position 2506 (C2506T) of SEQ ID NO: 1.

Several variants of BCR-ABL protein without truncation mutation are known in the art. Exemplary BCR-ABL protein sequences include but are not limited to NCBI protein database accession numbers: ABX82708, ABX82702, and AAA35594.

As used herein, the term "hybridize" or "hybridization" refers to the pairing of substantially complementary nucleotide sequences (strands of nucleic acid) to form a duplex or heteroduplex through formation of hydrogen bonds between complementary base pairs. Hybridization and the strength of hybridization (i.e., the strength of the association between the nucleic acids) is influenced by such factors as the degree of complementary between the nucleic acids, stringency of the conditions involved, and the T. of the formed hybrid. An oligonucleotide or polynucleotide (e.g., a probe or a primer) that is specific for a target nucleic acid will "hybridize" to the target nucleic acid under suitable conditions. See e.g., Sambrook, et al., Molecular Cloning: A Laboratory Manual, Second Edition (1989), Cold Spring Harbor Press, Plainview, N.Y.

As used herein, the term "specific hybridization" refers to an indication that two nucleic acid sequences share a high degree of complementarity. Specific hybridization complexes form under permissive annealing conditions and remain hybridized after any subsequent washing steps. Permissive conditions for annealing of nucleic acid sequences are routinely determinable by one of ordinary skill in the art and may occur, for example, at 65° C. in the presence of about 6×SSC. Stringency of hybridization may be expressed, in part, with reference to the temperature under which the wash steps are carried out. Such temperatures are typically selected to be about 5° C. to 20° C. lower than the thermal melting point (Tm) for the specific sequence at a defined ionic strength and pH. The Tm is the temperature (under defined ionic strength and pH) at which 50% of the target sequence hybridizes to a perfectly matched probe. Equations for calculating Tm and conditions for nucleic acid hybridization are known in the art.

As used herein, the term "stringent hybridization conditions" refers to hybridization conditions at least as stringent as the following: hybridization in 50% formamide, 5×SSC, 50 mM $NaH_2PO_4$, pH 6.8, 0.5% SDS, 0.1 mg/mL sonicated salmon sperm DNA, and 5× Denhart's solution at 42° C. overnight; washing with 2×SSC, 0.1% SDS at 45° C.; and washing with 0.2×SSC, 0.1% SDS at 45° C. In another example, stringent hybridization conditions should not allow for hybridization of two nucleic acids which differ over a stretch of 20 contiguous nucleotides by more than two bases.

As used herein, the term "substantially complementary" refers to two sequences that hybridize under stringent hybridization conditions. The skilled artisan will understand that substantially complementary sequences need not hybridize along their entire length.

As used herein, the term "oligonucleotide" as used herein refers to a molecule that has a sequence of nucleic acid bases on a backbone comprised mainly of identical monomer units at defined intervals. The bases are arranged on the backbone in such a way that they can enter into a bond with a nucleic acid having a sequence of bases that are complementary to the bases of the oligonucleotide. The most common oligonucleotides have a backbone of sugar phosphate units. A distinction may be made between oligodeoxyribonucleotides that do not have a hydroxyl group at the 2' position and oligoribonucleotides that have a hydroxyl group in this position. Oligonucleotides also may include derivatives, in which the hydrogen of the hydroxyl group is replaced with organic groups, e.g., an allyl group. Oligonucleotides of the methods which function as primers or probes are generally at least about 10 to 15 nucleotides long and more preferably at least about 15 to 25 nucleotides long, although shorter or longer oligonucleotides may be used in the method. The exact size will depend on many factors, which in turn depend on the ultimate function or use of the oligonucleotide. The oligonucleotide may be generated in any manner, including, for example, chemical synthesis, DNA replication, reverse transcription, PCR, or a combination thereof. The oligonucleotide may be modified. For example, the oligonucleotide may be labeled with an agent that produces a detectable signal (e.g., a fluorophore). Oligonucleotides can be used as primers or probes for specifically amplifying (i.e., amplifying a particular target nucleic acid sequence) or specifically detecting (i.e., detecting a particular target nucleic acid sequence) a target nucleic acid generally are capable of specifically hybridizing to the target nucleic acid.

As used herein, the term "primer" refers to an nucleic acid that is capable of acting as a point of initiation of synthesis when placed under conditions in which primer extension is initiated (e.g., primer extension associated with an application such as PCR). The primer is complementary to a target nucleotide sequence and it hybridizes to a substantially complementary sequence in the target and leads to addition of nucleotides to the 3"-end of the primer in the presence of a DNA or RNA polymerase. The 3'-nucleotide of the primer should generally be complementary to the target sequence at a corresponding nucleotide position for optimal expression and amplification. An oligonucleotide "primer" may occur naturally, as in a purified restriction digest or may be produced synthetically. The term "primer" includes all forms of primers that may be synthesized including peptide nucleic acid primers, locked nucleic acid primers, phosphorothioate modified primers, labeled primers, and the like. Primers are typically between about 10 and about 100 nucleotides in length, preferably between about 15 and about 60 nucleotides in length, more preferably between about 20 and about 50 nucleotides in length, and most preferably between about 25 and about 40 nucleotides in length. In some examples, primers can be at least 8, at least 12, at least 16, at least 20, at least 25, at least 30, at least 35, at least 40, at least 45, at least 50, at least 55, at least 60 nucleotides in length. An optimal length for a particular primer application may be readily determined in the manner described in H. Erlich, PCR Technology, Principles and Application for DNA Amplification (1989).

As used herein, the term "probe" refers to nucleic acid that interacts with a target nucleic acid via hybridization. A probe may be fully complementary to a target nucleic acid sequence or partially complementary. The level of complementarity will depend on many factors based, in general, on the function of the probe. A probe or probes can be used, for example to detect the presence or absence of a mutation in a nucleic acid sequence by virtue of the sequence characteristics of the target. Probes can be labeled or unlabeled, or modified in any of a number of ways well known in the art. A probe may specifically hybridize to a target nucleic acid. Probes may be DNA, RNA or a RNA/DNA hybrid. Probes may be oligonucleotides, artificial chromosomes, fragmented artificial chromosome, genomic nucleic acid, fragmented genomic nucleic acid, RNA, recombinant nucleic acid, fragmented recombinant nucleic acid, peptide nucleic acid (PNA), locked nucleic acid, oligomer of cyclic heterocycles, or conjugates of nucleic acid. Probes may comprise modified nucleobases, modified sugar moieties, and modified internucleotide linkages. A probe may be fully complementary to a target nucleic acid sequence or partially complementary. A probe may be used to detect the presence or absence of a target nucleic acid. Probes are typically at least about 10, 15, 20, 25, 30, 35, 40, 50, 60, 75, 100 nucleotides or more in length.

As used herein, the term "detectable label" refers to a molecule or a compound or a group of molecules or a group of compounds used to identify a nucleic acid or protein of interest. In some cases, the detectable label may be detected directly. In other cases, the detectable label may be a part of a binding pair, which can then be subsequently detected. Signals from the detectable label may be detected by various means and will depend on the nature of the detectable label. Detectable labels may be isotopes, fluorescent moieties, colored substances, and the like. Examples of means to detect detectable label include but are not limited to spectroscopic, photochemical, biochemical, immunochemical, electromagnetic, radiochemical, or chemical means, such as fluorescence, chemifluoresence, or chemiluminescence, or any other appropriate means.

As used herein, the term "promoter" refers to a segment of DNA that controls transcription of polynucleotide to which it is operatively linked. Promoters, depending upon the nature of the regulation, may be constitutive or regulated. Exemplary eukaryotic promoters contemplated for use include the SV40 early promoter, the cytomegalovirus (CMV) promoter, the mouse mammary tumor virus (MMTV) steroid-inducible promoter, Moloney murine leukemia virus (MMLV) promoter. Exemplary promoters suitable for use with prokaryotic hosts include T7 promoter, beta-lactamase promoter, lactose promoter systems, alkaline phosphatase promoter, a tryptophan (trp) promoter system, and hybrid promoters such as the tac promoter.

As used herein, the term "antibody" refers to a polypeptide, at least a portion of which is encoded by at least one immunoglobulin gene, or fragment thereof, and that can bind specifically to a desired target molecule. The term includes naturally-occurring forms, as well as fragments and derivatives. Fragments within the scope of the term "antibody" include those produced by digestion with various proteases, those produced by chemical cleavage and/or chemical dissociation, and those produced recombinantly, so long as the fragment remains capable of specific binding to a target molecule. Among such fragments are Fab, Fab', Fv, F(ab)'$_2$, and single chain Fv (scFv) fragments. Derivatives within the scope of the term include antibodies (or fragments thereof) that have been modified in sequence, but remain capable of specific binding to a target molecule, including: interspecies chimeric and humanized antibodies; antibody fusions; heteromeric antibody complexes and antibody fusions, such as diabodies (bispecific antibodies), single-chain diabodies, and intrabodies (see, e.g., Marasco (ed.), Intracellular Antibodies: Research and Disease Applications, Springer-Verlag New York, Inc. (1998) (ISBN: 3540641513). As used herein, antibodies can be produced by any known technique, including harvest from cell culture of native B lymphocytes, harvest from culture of hybridomas, recombinant expression systems, and phage display.

As used herein, the term "specifically binds to an epitope" in the context of an antibody refers to an antibody that specifically binds to BCR-ABL truncation mutants of BCR-ABL protein and does not bind to BCR-ABL proteins without such truncation mutation and thus can distinguish between BCR-ABL proteins with and without truncation mutation. In some examples, the antibodies specific for BCR-ABL truncation mutants binds to an amino acid sequence comprising SEQ ID NO: 6, 10, 15 or 19. In one example, the antibodies specific for BCR-ABL truncation mutants binds to an epitope comprising SEQ ID NO's 11, 16, or 20. In one example, the antibodies specific for BCR-ABL truncation mutants binds to BCR-ABL proteins having amino acid sequences of SEQ ID NO: 5, 9, 14 or 19.

As used herein, the term "myeloproliferative disease" or "myeloproliferative disorder" or "MPD" is meant to include non-lymphoid dysplastic or neoplastic conditions arising from a hematopoietic stem cell or its progeny. "MPD patient" or "myeloproliferative disease patient" refers to a patient diagnosed with a myeloproliferative disease or suspected of having a myeloproliferative disease. One of ordinary skill in the art is capable of diagnosing a myeloproliferative disease using suitable diagnostic criteria. "Myeloproliferative disease" is meant to encompass the specific, classified types of myeloproliferative diseases including chronic myelogenous leukemia (CML), acute myelogenous leukemia (AML), acute lymphoblastic leukemia (ALL), polycythemia vera (PV), essential thrombocythemia (ET) and idiopathic myelofibrosis (IMF). Also included in the definition are hypereosinophilic syndrome (HES), chronic neutrophilic leukemia (CNL), myelofibrosis with myeloid metaplasia (MMM), chronic myelomonocytic leukemia (CMML), juvenile myelomonocytic leukemia, chronic basophilic leukemia, chronic eosinophilic leukemia, and systemic mastocytosis (SM). "Myeloproliferative disease" is also meant to encompass any unclassified myeloproliferative diseases (UMPD or MPD-NC).

As used herein, the term "kinase domain" refers to a portion of a polypeptide or nucleic acid that encodes a portion of the polypeptide, where the portion is required for kinase activity of the polypeptide (e.g., tyrosine kinase activity).

As used herein, the term "diagnose" or "diagnosis" or "diagnosing" refer to distinguishing or identifying a disease, syndrome or condition or distinguishing or identifying a person having a particular disease, syndrome or condition. Usually, a diagnosis of a disease or disorder is based on the evaluation of one or more factors and/or symptoms that are indicative of the disease. That is, a diagnosis can be made based on the presence, absence or amount of a factor which is indicative of presence or absence of the disease or condition. Each factor or symptom that is considered to be indicative for the diagnosis of a particular disease does not need be exclusively related to the particular disease; i.e. there may be differential diagnoses that can be inferred from a diagnostic factor or symptom. Likewise, there may be instances where a factor or symptom that is indicative of a particular disease is present in an individual that does not have the particular disease.

As used herein, the term "treatment," "treating," or "treat" refers to care by procedures or application that are intended to relieve illness or injury. Although it is preferred that treating a condition or disease will result in an improvement of the condition, the term treating as used herein does not indicate, imply, or require that the procedures or applications are at all successful in ameliorating symptoms associated with any particular condition. Treating a patient may result in adverse side effects or even a worsening of the condition which the treatment was intended to improve.

As used herein, the term "altering the treatment" in reference to a patient includes, but is not limited to, adding a new drug to treatment regime, removing a drug from the treatment regime, changing dosage of a drug. In one example, the term refers to ceasing the use of imatinib in a myeloproliferative disease patient undergoing imatinib therapy. In other examples, the term refers to bone marrow transplant.

The term "prognosis" as used herein refers to a prediction of the probable course and outcome of a clinical condition or disease. A prognosis is usually made by evaluating factors or symptoms of a disease that are indicative of a favorable or unfavorable course or outcome of the disease. There are many ways that prognosis can be expressed. For example prognosis can be expressed in terms of complete remission rates (CR), overall survival (OS) which is the amount of time from entry to death, remission duration, which is the amount of time from remission to relapse or death.

The phrase "determining the prognosis" as used herein refers to the process by which the practitioner can predict the course or outcome of a condition in an individual. The term "prognosis" does not refer to the ability to predict the course or outcome of a condition with 100% accuracy. Instead, the skilled artisan will understand that the term "prognosis" refers to an increased probability that a certain course or outcome will occur; that is, that a course or outcome is more likely to occur in a patient exhibiting a given condition, when compared to those individuals not exhibiting the condition. A prognosis may be expressed as the amount of time a patient can be expected to survive. Alternatively, a prognosis may refer to the likelihood that the disease goes into remission or to the amount of time the disease can be expected to remain in remission. Prognosis can be expressed in various ways; for example prognosis can be expressed as a percent chance that a patient will survive after one year, five years, ten years or the like. Alternatively prognosis may be expressed as the number of years, on average that a patient can expect to survive as a result of a condition or disease. The prognosis of a patient may be considered as an expression of relativism, with many factors affecting the ultimate outcome. For example, for patients with certain conditions, prognosis can be appropriately expressed as the likelihood that a condition may be treatable or curable, or the likelihood that a disease will go into remission, whereas for patients with more severe conditions prognosis may be more appropriately expressed as likelihood of survival for a specified period of time.

As used herein, the term "poor prognosis" refers a the prognosis determined for a patient having a myeloproliferative disease which is worse (i.e., has a less favorable outcome) than the prognosis for a reference patient or group of patients with the same disease. For example, a patient with a poor prognosis may be expected to exhibit a reduced remission duration or survival time relative to reference patients (e.g., patients without one of the BCR-Abl truncation mutations described herein).

As used herein, the term "isolated" when referring to a nucleic acid or protein molecule means that the molecule is apart from its natural environment and/or is substantially separated from other cellular components which naturally accompany such molecule. For example, any nucleic acid or protein that has been produced synthetically (e.g., by serial base condensation) is considered to be isolated. Likewise, nucleic acids or proteins that are recombinantly expressed, cloned, produced by a synthetic in vitro reaction are considered to be isolated. An isolated nucleic acid or protein is at least 25% free, preferably at least 30% free, preferably at least 40% free, preferably at least 50% free, preferably at least 60% free, more preferably at least 75% free, and most preferably at least 90% free from other components with which it is naturally associated.

The term "substantially all" as used herein means at least about 60%, about 70%, about 80%, about 90%, about 95%, about 99%, or 100%.

"Substantially pure" as used herein in the context of nucleic acid represents at least 50%, at least 60%, at least 70%, at least 80%, at least 90%, at least 95% or at least 99% of the nucleic acid in a sample. The nucleic acid sample may exist in solution or as a dry preparation. As used herein, the term "including" has the same meaning as the term comprising.

As used herein, the term "about" means in quantitative terms, plus or minus 10%.

As used herein "portions of" in the context of nucleic acid means at least about 10, 20, 30, 40, 50, 60, 75, 100, 200, 500, 1000, 2000, 3000 or more nucleotides.

BRIEF DESCRIPTION OF FIGURES

FIG. 2A: Del 2595-2779, FIG. 2B: Del 2596-2597, FIG. 2C: 2417insCAGG, FIG. 2D: C2506T.

DETAILED DESCRIPTION OF THE INVENTION

Provided herein are methods and compositions related to mutations that encode a C-terminal truncated BCR-ABL protein that renders cells resistant to treatment with kinase domain inhibitors such as imatinib. In some examples, increasing amounts of the truncation mutant correlate directly with resistance. The inventions described herein include nucleic acid which encode all or portions of the truncation variant and cells that express all or portions of the truncation variant. Methods for predicting likelihood for responsiveness to kinase inhibitor therapy are included along with methods, compositions and reagents for detecting the truncation variant.

Variants of the BCR-ABL mRNA

Several variants of BCR-ABL mRNA have been reported. Many of the known sequences are full length cDNA sequences and some are partial cDNA sequences. Exemplary BCR-ABL mRNA sequences include but are not limited to: NCBI GenBank accession numbers: EU 216060, EU216072, EU216071, EU216070, EU216069, EU216068, EU216067, EU216066, EU216065, EU216064, EU216063, EU216062, EU216061, EU216060, EU216059, EU216058, EU236680, DQ912590, DQ912589, DQ912588, DQ898315, DQ898314, DQ898313, EF423615, EF158045, 572479, 572478, AY789120, AB069693, AF487522, AF113911, AF251769, M30829, M30832, M17542, M15025, and M17541. The nucleic acid sequences are incorporated herein by reference. An exemplary cDNA sequence of BCR-ABL cDNA is listed as SEQ ID NO: 1.

Variants of BCR-ABL Protein

Several variation of BCR-ABL protein sequence is known in the art. Some of the amino acid sequences are for full length protein and some are amino acid sequences for a fragment of BCR-ABL protein. Exemplary BCR-ABL protein sequence include but not limited to the NCBI protein database accession numbers: ABX82708, ABX82702, AAA35594, ACA62749, ABX82713, CAM33013, CAA10377, CAA10376, AAL99544, AAA88013, CAM33009, ABX82714, ABX82712, ABX82711, ABX82710, ABX82709, ABX82707, ABX82706, ABX82705, ABX82704, ABX82703, ABX82701, ABX82700, ABZ01959, ABW90981, AAL05889, AAA87612, CAM33011, CAP08044, ABM21758, AAD04633, AAF89176, ABZ01958, AB009836, ABZ01957, ABK56838, ABK56837, ABK56836, ABK19807, ABK19806, ABK19805, AAA35596, AAF61858, AAA35595, AAA35592. Sequences of the above proteins are incorporated herein by reference.

Figure 1:
FIG. 1. shows a schematic diagram of BCR-ABL protein. Different domains of BCR-ABL protein are indicated. BCR: portions of BCR protein, SH2 and SH3: Src homology domains 2 and 3 respectively, P: proline rich region, NLS: nuclear localization signal, DB: DNA-binding domain, AB: Actin-binding domain.

Exemplary amino acid sequence of full length BCR-ABL protein without any insertion or truncation mutation is listed in SEQ ID NO: 2. A schematic diagram of BCR-ABL protein showing the different domains is shown in FIG. 1. The domains include a portion of BCR protein, Src homology domains 2 and 3 (SH2 and SH3), proline rich regions (P), nuclear localization signal (NLS), and DNA- and Actin-binding domains DB and AB respectively.

Truncation Mutant of BCR-ABL Protein:

In some examples, myeloproliferative disease patients undergoing BCR-ABL tyrosine kinase inhibitor therapy (for example, imatinib, nilotinib, Bosutinib (SKI-606) and Aurora kinase inhibitor VX-680, or dasatinib), may subsequently acquire a mutation that affects the effectiveness of the tyrosine kinase inhibitor. The mutation may be a large deletion of nucleotides 2595-2779 of SEQ ID NO: 1, or an insertion of tetranucleotide CAGG at nucleotide position immediately after nucleotide 2417 of SEQ ID NO: 1, or a deletion of "GA" at position 2596-2597 of SEQ ID NO: 1, or a C to T substitution at position 2506 of SEQ ID NO: 1. These mutations cause truncation of a portion of kinase domain, abolish regulatory element in the ABL kinase domain and the downstream C-terminal region (such as, NLS, P, AB, DB domains) and confer resistance to kinase inhibitors such as imatinib, nilotinib, dasatinib, Bosutinib (SKI-606) and Aurora kinase inhibitor VX-680. Deletion of actin-binding domain or the entire C-terminal domain induces CIVIL-like myeloproliferative disorder in mice (Wertheim et al. Blood. 2003; 102: 2220-2228). The truncated proteins resulting from premature translation termination are expected to possess leukomogenic activity and to induce conformational change to confer drug resistance to kinase inhibitors.

Del 2595-2779

The deletion of nucleotides 2595-2779 results in a truncated BCR-ABL protein with a new C-terminal region for the BCR-ABL protein. Exemplary nucleic acid sequence of BCR-ABL Del 2595-2779 is listed as SEQ ID NO: 3. In some examples, the nucleic acid encoding the BCR-ABL Del 2595-2779 mRNA or cDNA, its fragments and complements thereof may include the deletion junction "GC" (nucleotides 2594 and 2595 of SEQ ID NO: 3) that is at least 95%, at least 99% identical or identical to at least 25, at least 26, at least 27, at least 28, or 29 contiguous nucleotides of SEQ ID NO: 4. Sequence of SEQ ID NO: 4 is shown below.

```
                                        (SEQ ID NO: 4)
        AACTTCATCCACAGCATTTGGAGTATTGC
```

The truncated BCR-ABL protein includes BCR portion of BCR-ABL protein, SH3 and SH2 domains and a portion of kinase domain. However the truncated protein lacks the P, NLS, DB and AB domains. Additionally, the C-terminus of the truncated BCR-ABL protein will comprise new amino acids. Exemplary amino acid sequence of the truncation mutant of BCR-ABL protein is listed as SEQ ID NO: 5. In preferred examples, C-terminal region of the BCR-ABL protein encoded by the BCR-ABL Del 2595-2779 mRNA may comprise a sequence of at least 75%, at least 80%, at least 85%, at least 90%, at least 99%, or identical to at least 15 contiguous amino acids of SEQ ID NO: 6. Sequence of SEQ ID NO: 6 is shown below.

```
                                        (SEQ ID NO: 6)
        EYLEKKNFIHSIWSIALGNCYLWHVPLPGN
```

In one example, the new amino acid sequence generated at the C-terminus of the truncated protein encoded by BCR-ABL Del 2595-2779 mRNA is:

```
                                        (SEQ ID NO: 20)
             SIWSIALGNCYLWHVPLPGN
```

Del 2596-2597

The Del 2596-2597 mutation is a deletion of 2 nucleotides "GA" at position 2597-2597 of the BCR-ABL gene resulting in a truncated BCR-ABL protein with a new C-terminal region for the BCR-ABL protein. Exemplary nucleic acid sequence of BCR-ABL Del 2596-2597 is listed as SEQ ID NO: 7. In some examples, the nucleic acid encoding the BCR-ABL Del 2596-2597 mRNA or cDNA, its fragments and complements thereof may include the deletion junction "AT" (nucleotides 2595 and 2596 of SEQ ID NO: 7) that is at least 95%, at least 99% identical or identical to at least 20, at least 25, or 30 contiguous nucleotides of SEQ ID NO: 8. Sequence of SEQ ID NO: 8 is shown below.

```
                                        (SEQ ID NO: 8)
        AACTTCATCCACAGATCTTGCTGCCCGAAA
```

The truncated BCR-ABL protein includes BCR portion of BCR-ABL protein, SH3 and SH2 domains and a portion of kinase domain. However the truncated protein lacks the P, NLS, DB and AB domains. Additionally, the C-terminus of the truncated BCR-ABL protein will comprise new amino acids. Exemplary amino acid sequence of the truncation mutant of BCR-ABL protein is listed as SEQ ID NO: 9. In preferred examples, C-terminal region of the BCR-ABL protein encoded by the BCR-ABL Del 2596-2597 mRNA may comprise a sequence of at least 85%, at least 90%, at least 95%, at least 99%, or identical to at least 20 contiguous amino acids of SEQ ID NO: 10. Sequence of SEQ ID NO: 10 is shown below.

(SEQ ID NO: 10)
SSAMEYLEKKNFIHRSCCPKLPGRGEPLGEGS

In one example, the new amino acid sequence generated at the C-terminus of the truncated protein encoded by BCR-ABL Del 2596-2597 mRNA is:

(SEQ ID NO: 11)
SCCPKLPGRGEPLGEGS

2417insCAGG

The 2417insCAGG mutation is an insertion of tetranucleotide CAGG immediately after nucleotide position 2417 of SEQ ID NO: 1 resulting in a truncated BCR-ABL protein with a new C-terminal region for the BCR-ABL protein. Exemplary nucleic acid sequence of BCR-ABL 2417insCAGG is listed as SEQ ID NO: 12. In some examples, the nucleic acid encoding BCR-ABL 2417insCAGG mRNA or cDNA, its fragments and complements thereof may include the CAGG insert that is at least 95%, at least 99% identical or identical to at least 25 or 30 contiguous nucleotides of SEQ ID NO: 13. Sequence of SEQ ID NO: 13 is shown below.

(SEQ ID NO: 13)
CTGGTGCAGCTCCTTGGCAGGGGTCTGCAC

The truncated BCR-ABL protein encoded by BCR-ABL 2417insCAGG mRNA includes BCR portion of BCR-ABL protein, SH3 and SH2 domains and a portion of kinase domain. However the truncated protein lacks the P, NLS, DB and AB domains. Additionally, the C-terminus of the truncated BCR-ABL protein will comprise new amino acids. Exemplary amino acid sequence of the truncation mutant of BCR-ABL protein is listed as SEQ ID NO: 14. In some examples, C-terminal region of the BCR-ABL protein encoded by the BCR-ABL 2417insCAGG mRNA may comprise a sequence of at least 75%, at least 80%, at least 85%, at least 90%, at least 95%, at least 99%, or identical to least 20 contiguous amino acids of SEQ ID NO: 15. Sequence of SEQ ID NO: 15 is shown below.

(SEQ ID NO: 15)
AVMKEIKHPNLVQLLGRGLHPGAPVLYHEI

In one example, the new amino acid sequence generated at the C-terminus of the truncated protein encoded by BCR-ABL 2417insCAGG mRNA is:

(SEQ ID NO: 16)
RGLHPGAPVLYHH

C2506T

The C2506T mutation is a single base substitution at position 2506 of SEQ ID NO: 1 resulting in a truncated BCR-ABL protein with a new C-terminal region for the BCR-ABL protein. Exemplary nucleic acid sequence of BCR-ABL C2506T is listed as SEQ ID NO: 17. In some examples, the nucleic acid encoding the BCR-ABL C2506T mRNA or cDNA, its fragments and complements thereof may include a "C" to "T" at nucleotide position 2506 of SEQ ID NO: 1 that is at least 95%, at least 99% identical or identical to at least 20 or 30 contiguous nucleotides of SEQ ID NO: 18. Sequence of SEQ ID NO: 18 is shown below.

(SEQ ID NO: 18)
AGGGAGTGCAACCGGTAGGAGGTGAACGCC

The truncated BCR-ABL protein encoded by BCR-ABL C2506T mRNA includes BCR portion of BCR-ABL protein, SH3 and SH2 domains and a portion of kinase domain. However the truncated protein lacks the P, NLS, DB and AB domains. Exemplary amino acid sequence of the truncation mutant of BCR-ABL protein is listed as SEQ ID NO: 19. In preferred examples, C-terminal region of the BCR-ABL protein encoded by the BCR-ABL C2506T mRNA may comprise a sequence of at least 75%, at least 80%, at least 85%, at least 90%, at least 95%, at least 99%, or identical to least 20 contiguous amino acids of SEQ ID NO: 19.

In some examples, CML patients undergoing kinase inhibitor therapy may develop two kinds of mutations: a) an truncation mutant of BCR-ABL protein such as Del 2595-2779, Del 2596-2597, 2417insCAGG, C2506T and b) one or more point mutations in the kinase domain of Abl. Exemplary point mutations in the Abl kinase domain include: Q252H, G250E, H396R, F359V, M244V, E255K, Y253H, E255V, T315I (Position numberings of these mutants are based on the wild type ABL protein, GenBank accession number AAA51561).

In some examples, the truncation variant of BCR-ABL mRNA can be detected simultaneously with the detection of mutations in ABL portion of BCR-ABL mRNA. In another example, the mutations in the ABL portion of BCR-ABL mRNA can be detected separately. Several methods are known in the art for detection of the presence or absence of such mutations. Non limiting examples include, DNA sequencing, detection by hybridization of a detectably labeled probe, detection by size, allele specific PCR, ligation amplification reaction (LAR), detection by oligonucleotide arrays.

Biological Sample Collection and Preparation

The methods provided herein may be performed using any biological sample. Biological samples may be obtained by standard procedures and may be used immediately or stored (e.g., the sample may be frozen between about −15° C. to about −100° C.) for later use. The presence of nucleic acids having BCR-ABL truncation mutation in a sample can be determined by amplifying all portions of BCR-ABL nucleic acid. Thus, any liquid or solid material believed to contain BCR-ABL nucleic acids can be an appropriate sample. Preferred the sample is blood. More preferably the sample is plasma. In one example, the sample may be obtained from an individual who is suspected of having a disease, or a genetic abnormality. In another example sample may be obtained from a healthy individual who is assumed of having no disease, or a genetic abnormality. In preferred examples, the sample may be obtained from myeloproliferative disease patients undergoing kinase inhibitor therapy. In another example, sample may be obtained from myeloproliferative disease patients not undergoing kinase inhibitor therapy.

In another example, nucleic acid may be mRNA or cDNA generated from mRNA or total RNA may be used. RNA is isolated from cells or tissue samples using standard techniques, see, e.g., Sambrook, et al., Molecular Cloning: A Laboratory Manual, Second Edition (1989), Cold Spring Harbor Press, Plainview, N.Y. In addition, reagents and kits for isolating RNA from any biological sample such as whole blood, plasma, serum, buffy coat, bone marrow, other body fluids, lymphocytes, cultured cells, tissue, and forensic specimens are commercially available e.g., RNeasy Protect Mini kit, RNeasy Protect Cell Mini kit, QIAamp RNA Blood Mini kit, RNeasy Protect Saliva Mini kit, Paxgene Blood RNA kit from Qiagen; MELT™, RNaqueous®, ToTALLY RNA™, RiboPure™-Blood, Poly(A)Purist™ from Applied Biosystems; TRIZOL® reagent, Dynabeads® mRNA direct kit from Invitrogen.

Nucleic Acid Amplification

Nucleic acids may be amplified by various methods known to the skilled artisan. Nucleic acid amplification may be linear or exponential. Amplification is generally carried out using polymerase chain reaction (PCR) technologies known in the art. See e.g., Mullis and Faloona, Methods Enzymol. (1987), 155:335, U.S. Pat. Nos. 4,683,202, 4,683,195 and 4,800,159.

Alternative methods to PCR include for example, isothermal amplification methods, rolling circle methods, Hot-start PCR, real-time PCR, Allele-specific PCR, Assembly PCR or Polymerase Cycling Assembly (PCA), Asymmetric PCR, Colony PCR, Emulsion PCR, Fast PCR, Real-Time PCR, nucleic acid ligation, Gap Ligation Chain Reaction (Gap LCR), Ligation-mediated PCR, Multiplex Ligation-dependent Probe Amplification, (MLPA), Gap Extension Ligation PCR (GEXL-PCR), quantitative PCR (Q-PCR), Quantitative real-time PCR (QRT-PCR), multiplex PCR, Helicase-dependent amplification, Intersequence-specific (ISSR) PCR, Inverse PCR, Linear-After-The-Exponential-PCR (LATE-PCR), Methylation-specific PCR (MSP), Nested PCR, Overlap-extension PCR, PAN-AC assay, Reverse Transcription PCR (RT-PCR), Rapid Amplification of cDNA Ends (RACE PCR), Single molecule amplification PCR (SMA PCR), Thermal asymmetric interlaced PCR (TAIL-PCR), Touchdown PCR, long PCR, nucleic acid sequencing (including DNA sequencing and RNA sequencing), transcription, reverse transcription, duplication, DNA or RNA ligation, and other nucleic acid extension reactions known in the art. The skilled artisan will understand that other methods may be used either in place of, or together with, PCR methods, including enzymatic replication reactions developed in the future. See, e.g., Saiki, "Amplification of Genomic DNA" in PCR Protocols, Innis et al., eds., Academic Press, San Diego, Calif., 13-20 (1990); Wharam, et al., 29(11) Nucleic Acids Res, E54-E54 (2001); Hafner, et al., 30(4) Biotechniques, 852-6, 858, 860 passim (2001).

Nucleic Acid Detection

Amplification of nucleic acids can be detected by any of a number of methods well-known in the art such as gel electrophoresis, column chromatography, hybridization with a probe, or sequencing.

Detectable labels can be used to identify the probe hybridized to a genomic nucleic acid or reference nucleic acid. Detectable labels include but are not limited to fluorophores, isotopes (e.g., $^{32}P$, $^{33}P$, $^{35}S$, $^{3}H$, $^{14}C$, $^{125}I$, $^{131}I$) electron-dense reagents (e.g., gold, silver), nanoparticles, enzymes commonly used in an ELISA (e.g., horseradish peroxidase, beta-galactosidase, luciferase, alkaline phosphatase), chemiluminiscent compound, colorimetric labels (e.g., colloidal gold), magnetic labels (e.g., Dynabeads™), biotin, digoxigenin, haptens, proteins for which antisera or monoclonal antibodies are available, ligands, hormones, oligonucleotides capable of forming a complex with the corresponding oligonucleotide complement.

One general method for real time PCR uses fluorescent probes such as the TaqMan® probes (Heid, et al., Genome Res 6: 986-994, 1996), molecular beacons, and Scorpions™. Real-time PCR quantifies the initial amount of the template with more specificity, sensitivity and reproducibility, than other forms of quantitative PCR, which detect the amount of final amplified product. Real-time PCR does not detect the size of the amplicon. The probes employed in Scorpion™ and TaqMan® technologies are based on the principle of fluorescence quenching and involve a donor fluorophore and a quenching moiety.

In a preferred example, the detectable label is a fluorophore. The term "fluorophore" as used herein refers to a molecule that absorbs light at a particular wavelength (excitation frequency) and subsequently emits light of a longer wavelength (emission frequency). The term "donor fluorophore" as used herein means a fluorophore that, when in close proximity to a quencher moiety, donates or transfers emission energy to the quencher. As a result of donating energy to the quencher moiety, the donor fluorophore will itself emit less light at a particular emission frequency that it would have in the absence of a closely positioned quencher moiety.

The term "quencher moiety" as used herein means a molecule that, in close proximity to a donor fluorophore, takes up emission energy generated by the donor and either dissipates the energy as heat or emits light of a longer wavelength than the emission wavelength of the donor. In the latter case, the quencher is considered to be an acceptor fluorophore. The quenching moiety can act via proximal (i.e., collisional) quenching or by Förster or fluorescence resonance energy transfer ("FRET"). Quenching by FRET is generally used in TaqMan® probes while proximal quenching is used in molecular beacon and Scorpion™ type probes.

Suitable fluorescent moieties include but are not limited to the following fluorophores working individually or in combination:
4-acetamido-4'-isothiocyanatostilbene-2,2'disulfonic acid; acridine and derivatives: acridine, acridine isothiocyanate; Alexa Fluors: Alexa Fluor® 350, Alexa Fluor® 488, Alexa Fluor® 546, Alexa Fluor® 555, Alexa Fluor® 568, Alexa Fluor® 594, Alexa Fluor® 647 (Molecular Probes); 5-(2'-aminoethyl)aminonaphthalene-1-sulfonic acid (EDANS); 4-amino-N-[3-vinylsulfonyl)phenyl]naphthalimide-3,5 disulfonate (Lucifer Yellow VS); N-(4-anilino-1-naphthyl)maleimide; anthranilamide; Black Hole Quencher™ (BHQ™) dyes (biosearch Technologies); BODIPY dyes: BODIPY® R-6G, BOPIPY® 530/550, BODIPY® FL; Brilliant Yellow; coumarin and derivatives: coumarin, 7-amino-4-methylcoumarin (AMC, Coumarin 120), 7-amino-4-trifluoromethylcouluarin (Coumarin 151); Cy2®, Cy3®, Cy3.5®, Cy5®, Cy5.5®; cyanosine; 4',6-diaminidino-2-phenylindole (DAPI); 5', 5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); Eclipse™ (Epoch Biosciences Inc.); eosin and derivatives: eosin, eosin isothiocyanate; erythrosin and derivatives: erythrosin B, erythrosin isothiocyanate; ethidium; fluorescein and derivatives: 5-carboxyfluorescein (FAM), 5-(4,6-dichlorotriazin-2-yl)aminofluorescein (DTAF), 2',7'-dimethoxy-4'5'-dichloro-6-carboxyfluorescein (JOE), fluorescein, fluorescein isothiocyanate (FITC), hexachloro-6-carboxyfluorescein (HEX), QFITC (XRITC), tetrachlorofluorescein (TET); fluorescamine; IR144; IR1446;

lanthamide phosphors; Malachite Green isothiocyanate; 4-methylumbelliferone; ortho cresolphthalein; nitrotyrosine; pararosaniline; Phenol Red; B-phycoerythrin, R-phycoerythrin; allophycocyanin; o-phthaldialdehyde; Oregon Green®; propidium iodide; pyrene and derivatives: pyrene, pyrene butyrate, succinimidyl 1-pyrene butyrate; QSY® 7; QSY® 9; QSY® 21; QSY® 35 (Molecular Probes); Reactive Red 4 (Cibacron® Brilliant Red 3B-A); rhodamine and derivatives: 6-carboxy-X-rhodamine (ROX), 6-carboxyrhodamine (R6G), lissamine rhodamine B sulfonyl chloride, rhodamine (Rhod), rhodamine B, rhodamine 123, rhodamine green, rhodamine X isothiocyanate, riboflavin, rosolic acid, sulforhodamine B, sulforhodamine 101, sulfonyl chloride derivative of sulforhodamine 101 (Texas Red); terbium chelate derivatives; N,N,N',N'-tetramethyl-6-carboxyrhodamine (TAMRA); tetramethyl rhodamine; tetramethyl rhodamine isothiocyanate (TRITC).

Other fluorescent nucleotide analogs can be used, see, e.g., Jameson, Meth. Enzymol. (1997), 278:363-390; Zhu et al., Nucleic Acids Res. (1994), 22:3418-3422. U.S. Pat. Nos. 5,652,099 and 6,268,132 also describe nucleoside analogs for incorporation into nucleic acids, e.g., DNA and/or RNA, or oligonucleotides, via either enzymatic or chemical synthesis to produce fluorescent oligonucleotides. U.S. Pat. No. 5,135,717 describes phthalocyanine and tetrabenztriazaporphyrin reagents for use as fluorescent labels.

The detectable label can be incorporated into, associated with or conjugated to a nucleic acid. Label can be attached by spacer arms of various lengths to reduce potential steric hindrance or impact on other useful or desired properties. See, e.g., Mansfield, Mol. Cell. Probes (1995), 9:145-156.

Detectable labels can be incorporated into nucleic acid probes by covalent or non-covalent means, e.g., by transcription, such as by random-primer labeling using Klenow polymerase, or nick translation, or, amplification, or equivalent as is known in the art. For example, a nucleotide base is conjugated to a detectable moiety, such as a fluorescent dye, e.g., Cy3™ or Cy5™ and then incorporated into nucleic acid probes during nucleic acid synthesis or amplification. Nucleic acid probes can thereby be labeled when synthesized using Cy3™- or Cy5™-dCTP conjugates mixed with unlabeled dCTP.

Nucleic acid probes can be labeled by using PCR or nick translation in the presence of labeled precursor nucleotides, for example, modified nucleotides synthesized by coupling allylamine-dUTP to the succinimidyl-ester derivatives of the fluorescent dyes or haptens (such as biotin or digoxigenin) can be used; this method allows custom preparation of most common fluorescent nucleotides, see, e.g., Henegariu et al., Nat. Biotechnol. (2000), 18:345-348, Nucleic acid probes may be labeled by non-covalent means known in the art. For example, Kreatech Biotechnology's Universal Linkage System® (ULS®) provides a non-enzymatic labeling technology, wherein a platinum group forms a co-ordinative bond with DNA, RNA or nucleotides by binding to the N7 position of guanosine. This technology may also be used to label proteins by binding to nitrogen and sulfur containing side chains of amino acids. See, e.g., U.S. Pat. Nos. 5,580,990; 5,714,327; and 5,985,566; and European Patent No. EP 0539466.

Labeling with a detectable label also can include a nucleic acid attached to another biological molecule, such as a nucleic acid, e.g., an oligonucleotide, or a nucleic acid in the form of a stem-loop structure as a "molecular beacon" or an "aptamer beacon". Molecular beacons as detectable moieties are well known in the art; for example, Sokol (Proc. Natl. Acad. Sci. USA (1998), 95:11538-11543) synthesized "molecular beacon" reporter oligodeoxynucleotides with matched fluorescent donor and acceptor chromophores on their 5' and 3' ends. In the absence of a complementary nucleic acid strand, the molecular beacon remains in a stem-loop conformation where fluorescence resonance energy transfer prevents signal emission. On hybridization with a complementary sequence, the stem-loop structure opens increasing the physical distance between the donor and acceptor moieties thereby reducing fluorescence resonance energy transfer and allowing a detectable signal to be emitted when the beacon is excited by light of the appropriate wavelength. See also, e.g., Antony (Biochemistry (2001), 40:9387-9395,), describing a molecular beacon consist of a G-rich 18-mer triplex forming oligodeoxyribonucleotide. See also U.S. Pat. Nos. 6,277,581 and 6,235,504.

Aptamer beacons are similar to molecular beacons; see, e.g., Hamaguchi, Anal. Biochem. (2001), 294:126-131; Poddar, Mol. Cell. Probes (2001), 15:161-167; Kaboev, Nucleic Acids Res. (2000), 28:E94. Aptamer beacons can adopt two or more conformations, one of which allows ligand binding. A fluorescence-quenching pair is used to report changes in conformation induced by ligand binding. See also, e.g., Yamamoto et al., Genes Cells (2000), 5:389-396; Smirnov et al., Biochemistry (2000), 39:1462-1468.

The nucleic acid probe may be indirectly detectably labeled via a peptide. A peptide can be made detectable by incorporating predetermined polypeptide epitopes recognized by a secondary reporter (e.g., leucine zipper pair sequences, binding sites for secondary antibodies, transcriptional activator polypeptide, metal binding domains, epitope tags). A label may also be attached via a second peptide that interacts with the first peptide (e.g., S-S association).

As readily recognized by one of skill in the art, detection of the complex containing the nucleic acid from a sample hybridized to a labeled probe can be achieved through use of a labeled antibody against the label of the probe. In a preferred example, the probe is labeled with digoxigenin and is detected with a fluorescent labeled anti-digoxigenin antibody. In another example, the probe is labeled with FITC, and detected with fluorescent labeled anti-FITC antibody. These antibodies are readily available commercially. In another example, the probe is labeled with FITC, and detected with anti-FITC antibody primary antibody and a labeled anti-anti FITC secondary antibody.

Detection of Nucleic Acid by Size:

Methods for detecting the presence or amount of nucleic acid are well known in the art and any of them can be used in the methods described herein so long as they are capable of separating individual nucleic acid by the difference in size of the amplicons. The separation technique used should permit resolution of nucleic acid as long as they differ from one another by at least one nucleotide. The separation can be performed under denaturing or under non-denaturing or native conditions—i.e., separation can be performed on single- or double-stranded nucleic acids. It is preferred that the separation and detection permits detection of length differences as small as one nucleotide. It is further preferred that the separation and detection can be done in a high-throughput format that permits real time or contemporaneous determination of amplicon abundance in a plurality of reaction aliquots taken during the cycling reaction. Useful methods for the separation and analysis of the amplified products include, but are not limited to, electrophoresis (e.g., agarose gel electrophoresis, capillary electrophoresis (CE)), chromatography (HPLC), and mass spectrometry.

DNA Sequencing:

In some examples, detection of nucleic acid is by DNA sequencing. Sequencing may be carried out by the dideoxy chain termination method of Sanger et al. (Proceedings of the National Academy of Sciences USA (1977), 74, 5463-5467) with modifications by Zimmermann et al. (Nucleic Acids Res. (1990), 18:1067). Sequencing by dideoxy chain termination method can be performed using Thermo Sequenase (Amersham Pharmacia, Piscataway, N.J.), Sequenase reagents from US Biochemicals or Sequatherm sequencing kit (Epicenter Technologies, Madison, Wis.). Sequencing may also be carried out by the "RR dRhodamine Terminator Cycle Sequencing Kit" from PE Applied Biosystems (product no. 403044, Weiterstadt, Germany), Taq DyeDeoxy™ Terminator Cycle Sequencing kit and method (Perkin-Elmer/Applied Biosystems) in two directions using an Applied Biosystems Model 373A DNA or in the presence of dye terminators CEQ™ Dye Terminator Cycle Sequencing Kit, (Beckman 608000). Alternatively, sequencing can be performed by a method known as Pyrosequencing (Pyrosequencing, Westborough, Mass.). Detailed protocols for Pyrosequencing can be found in: Alderborn et al., Genome Res. (2000), 10:1249-1265.

Detection of BCR-ABL Truncation Mutation by Hybridization of a Nucleic Acid Probe BCR-ABL truncation mutation may be detected by hybridization of a nucleic acid probe to genomic DNA or to a portion of amplified nucleic acid comprising the mutation. Probes may encompass the deletion junction (for Del 2595-2779: nucleotides 2594 and 2595 of SEQ ID NO: 3; for del 2596-2597: nucleotides 2595 and 2596 of SEQ ID NO: 7; for 2417insCAGG: nucleotides 2418-2421 of SEQ ID NO: 12) or mutation site (nucleotide position 2506 of SEQ ID NO: 17) of BCR-ABL nucleic acid where a first portion of the probe may be specific for a portion of BCR-ABL nucleic acid in the 5'-end of the deletion junction or mutation site and a second portion of the probe may be specific 3'-end of the deletion junction or mutation site.

Cloning

The nucleic acid (e.g., cDNA or genomic DNA) encoding at least a portion of BCR-ABL or its variants may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art, see Sambrook, et al., Molecular Cloning: A Laboratory Manual (1989), Second Edition, Cold Spring Harbor Press, Plainview, N.Y.

Prokaryotic Vectors:

Prokaryotic transformation vectors are well-known in the art and include pBlueskript and phage Lambda ZAP vectors (Stratagene, La Jolla, Calif.), and the like. Other suitable vectors and promoters are disclosed in detail in U.S. Pat. No. 4,798,885, issued Jan. 17, 1989, the disclosure of which is incorporated herein by reference in its entirety.

Other suitable vectors for transformation of E. coli cells include the pET expression vectors (Novagen, see U.S. Pat. No. 4,952,496), e.g., pET11a, which contains the T7 promoter, T7 terminator, the inducible E. coli lac operator, and the lac repressor gene; and pET 12a-c, which contain the T7 promoter, T7 terminator, and the E. coli ompT secretion signal. Another suitable vector is the pIN-IIIompA2 (see Duffaud et al., Meth. in Enzymology, 153:492-507, 1987), which contains the lpp promoter, the lacUV5 promoter operator, the ompA secretion signal, and the lac repressor gene.

Eukaryotic Vectors:

Exemplary, eukaryotic transformation vectors, include the cloned bovine papilloma virus genome, the cloned genomes of the murine retroviruses, and eukaryotic cassettes, such as the pSV-2 gpt system [described by Mulligan and Berg, Nature Vol. 277:108-114 (1979)] the Okayama-Berg cloning system [Mol. Cell. Biol. Vol. 2:161-170 (1982)], and the expression cloning vector described by Genetics Institute (Science. 1985; 228: 810-815), pCMV Sport, pCDNA™ 3.3 TOPO®, BaculoDirect™ Baculovirus Expression System (Invitrogen Corp., Carlsbad, Calif., USA), StrataClone™ (Stratagene, CA, USA), pBAC vectors (EMD Chemicals Inc, NJ, USA).

Vector Components:

Vector components generally include, but are not limited to, one or more of a regulatory elements such as an enhancer element, a promoter, and a transcription termination sequence, an origin of replication, one or more selection marker genes, and a cloning site.

Figure 3A:
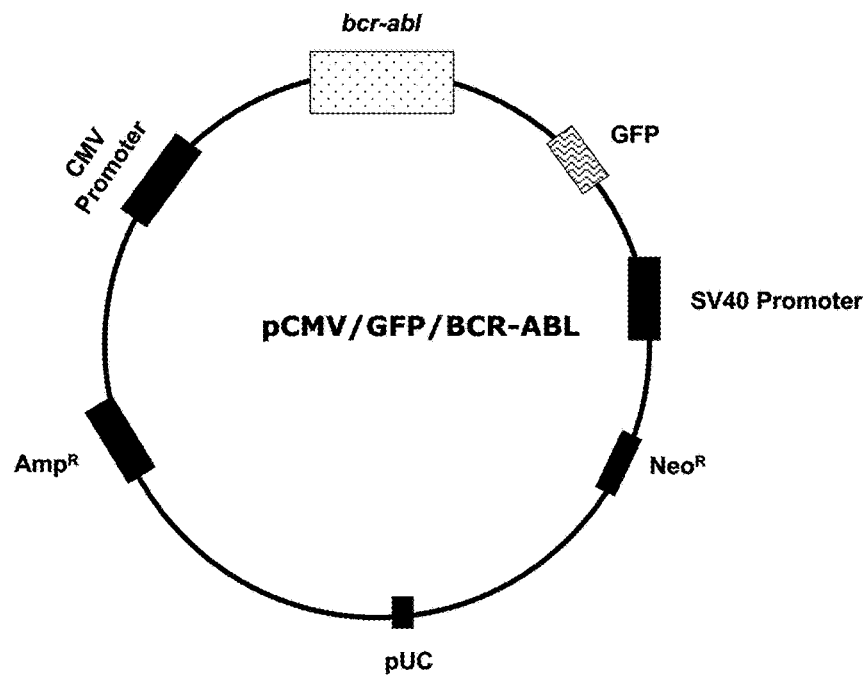
FIGS. 3A-3B show maps of expression vectors comprising BCR-ABL wild type and its truncation mutation variants.
Figure 3B:
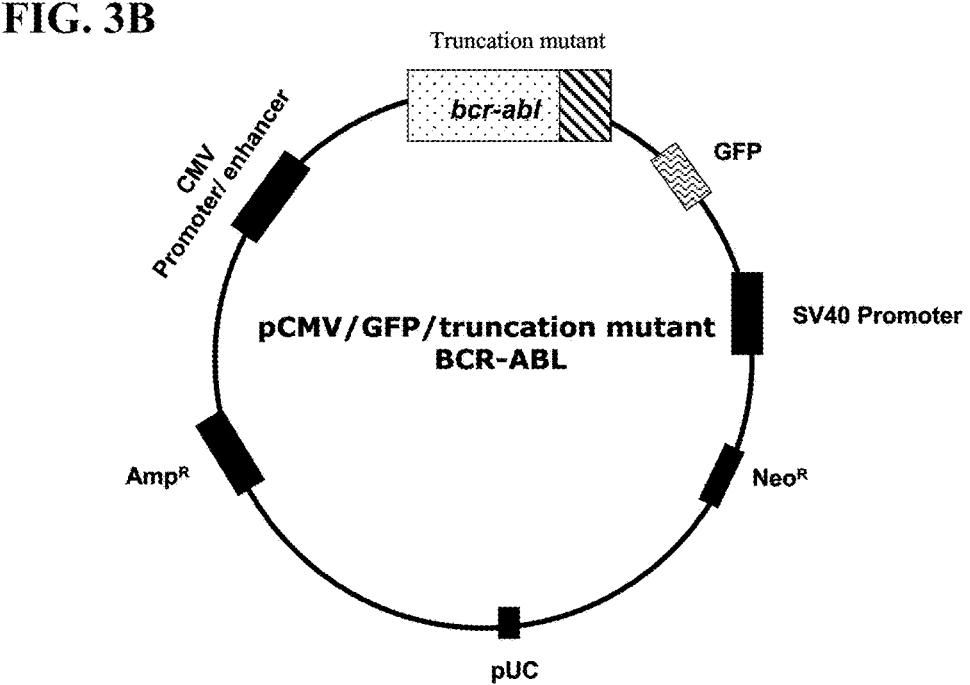

Vectors encoding BCR-ABL nucleic acid sequence and its variants may further comprise non-BCR-ABL nucleic acid sequence which may be co-expressed with BCR-ABL and its variants either as a fusion product or as a co-transcript. Non limiting examples of such non-BCR-ABL nucleic acid sequence include His-tag (a stretch of poly histidines), FLAG-tag, and Green Fluorescent Protein (GFP). His-tag and FLAG-tag can be used to in many different methods, such as purification of BCR-ABL protein and or truncation mutant of BCR-ABL protein fused to such tags. The tags can also serve as an important site for antibody recognition. This is particularly important in detecting BCR-ABL proteins and or truncation mutant of BCR-ABL protein fused to such tags. GFP may be used as a reporter of expression (Phillips G. J. FEMS Microbiol. Lett. 2001; 204 (1): 9-18), such as the expression of BCR-ABL and the truncation variant of BCR-ABL. Exemplary design of vectors encoding BCR-ABL and the truncation variant of BCR-ABL sequence is shown in FIGS. 3A and 3B respectively.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNA or cDNA. These regions contain nucleotide segments transcribed as polyadenylated fragments in the untranslated portion of the mRNA encoding BCR-ABL.

Still other methods, vectors, and host cells suitable for adaptation to the synthesis of BCR-ABL in recombinant vertebrate cell culture are described in Gething et al., Nature (1981), 293:620-625; Mantei et al., Nature. 1979; 281:40-46; EP 117,060; and EP 117,058.

Genetically Modifying Host Cells by Introducing Recombinant Nucleic Acid

The recombinant nucleic acid (e.g., cDNA or genomic DNA) encoding at least a portion of BCR-ABL or its variants may be introduced into host cells thereby genetically modifying the host cell. Host cells may be used for cloning and/or for expression of the recombinant nucleic acid. Host cells can be also be prokaryotic, for example bacteria. Host cell can be also be eukaryotic which includes but not limited to yeast, fungal cell, insect cell, plant cell and animal cell. In preferred example, the host cell can be a mammalian cell. In another preferred example host cell can be human cell. In one preferred example, the eukaryotic host cell may be K562 cell. K562 cells were the first human immortalized myelogenous leukemia line to be established and are a BCR-ABL positive erythroleukemia line derived from a CIVIL patient in blast crisis (Lozzio & Lozzio, Blood. 1975; 45(3): 321-334; Drexler, H. G. The Leukemia-Lymphoma Cell Line Factsbook. (2000), Academic Press.

Host cells may comprise wild-type genetic information. The genetic information of the host cells may be altered on purpose to allow it to be a permissive host for the recombinant DNA. Examples of such alterations include mutations, partial or total deletion of certain genes, or introduction of non-host nucleic acid into host cell. Host cells may also comprise mutations which are not introduced on purpose.

Several methods are known in the art to introduce recombinant DNA in bacterial cells that include but are not limited to transformation, transduction, and electroporation, see Sambrook, et al., Molecular Cloning: A Laboratory Manual (1989), Second Edition, Cold Spring Harbor Press, Plainview, N.Y. Non limiting examples of commercial kits and bacterial host cells for transformation include NovaBlue Singles™ (EMD Chemicals Inc, NJ, USA), Max Efficiency® DH5α™, One Shot® BL21 (DE3) *E. coli* cells, One Shot® BL21 (DE3) pLys *E. coli* cells (Invitrogen Corp., Carlsbad, Calif., USA), XL1-Blue competent cells (Stratagene, CA, USA). Non limiting examples of commercial kits and bacterial host cells for electroporation include Zappers™ electrocompetent cells (EMD Chemicals Inc, NJ, USA), XL1-Blue Electroporation-competent cells (Stratagene, CA, USA), ElectroMAX™ *A. tumefaciens* LBA4404 Cells (Invitrogen Corp., Carlsbad, Calif., USA).

Several methods are known in the art to introduce recombinant nucleic acid in eukaryotic cells. Exemplary methods include transfection, electroporation, liposome mediated delivery of nucleic acid, microinjection into to the host cell, see Sambrook, et al., Molecular Cloning: A Laboratory Manual (1989), Second Edition, Cold Spring Harbor Press, Plainview, N.Y. Non limiting examples of commercial kits and reagents for transfection of recombinant nucleic acid to eukaryotic cell include Lipofectamine™ 2000, Optifect™ Reagent, Calcium Phosphate Transfection Kit (Invitrogen Corp., Carlsbad, Calif., USA), GeneJammer® Transfection Reagent, LipoTAXI® Trasfection Reagent (Stratagene, CA, USA). Alternatively, recombinant nucleic acid may be introduced into insect cells (e.g. sf9, sf21, High Five™) by using baculo viral vectors.

In one preferred example, an exemplary vector comprising the cDNA sequence of BCR-ABL truncation variant (pCMV/GFP/truncation mutant BCR-ABL, shown in FIG. 2B) may be transfected into K562 cells. Stable transfected K 562 cells may be developed by transfecting the cells with varying amounts of the pCMV/GFP/truncation mutant vector (0 ng-500 ng) using various methods known in the art. In one exemplary method, The ProFection® Mammalian Transfection System—Calcium Phosphate (Promega Corporation, WI, USA) may be used. This is a simple system containing two buffers: CaCl2 and HEPES-buffered saline. A precipitate containing calcium phosphate and DNA is formed by slowly mixing a HEPES-buffered phosphate solution with a solution containing calcium chloride and DNA. These DNA precipitates are then distributed onto eukaryotic cells and enter the cells through an endocytic-type mechanism. This transfection method has been successfully used by others (Hay et al. J. Biol. Chem. 2004; 279: 1650-58). The transfected K562 cells can be selected from the non-transfected cells by using the antibiotics Neomycin and Ampicillin. Expression of the truncation variant of BCR-ABL can assessed from the co-expression of the reporter gene GFP.

Alternatively, in a 24-well format complexes are prepared using a DNA (µg) to Lipofectamine™ 2000 (Invitrogen Corporation, Carlsbad, Calif., USA) (pi) ratio of 1:2 to 1:3. Cells are transfected at high cell density for high efficiency, high expression levels, and to minimize cytotoxicity. Prior to preparing complexes, $4-8 \times 10^5$ cells are plated in 500 µl of growth medium without antibiotics. For each transfection sample, complexes are prepared as follows: a. DNA is diluted in 50 µl of Opti-MEM® I Reduced Serum Medium without serum (Invitrogen Corporation, Carlsbad, Calif., USA) or other medium without serum and mixed gently. b. Lipofectamine™ 2000 is mixed gently before use and the mixture is diluted to appropriate amount in 50 µl of Opti-MEM® I Medium. The mixture is incubated for 5 minutes at room temperature. c. After 5 minute incubation, the diluted DNA is combined with diluted Lipofectamine™ 2000 (total volume=100 µl) and is mixed gently. The mixture is incubated for 20 minutes at room temperature. 100 µl of complexes is added to each well containing cells and medium. The contents are mixed gently by rocking the plate back and forth. Cells are incubated at 37° C. in a CO2 incubator for 18-48 hours prior to testing for transgene expression. Medium may be changed after 4-6 hours. Cells are passaged at a 1:10 (or higher dilution) into fresh growth medium 24 hours after transfection. Selective medium (containing Neomycin and Ampicillin) is added the following day.

Isolation of BCR-ABL Polypeptide

BCR-ABL proteins with and without truncation mutation may be recovered from biological sample from an individual, culture medium or from host cell lysates. If membrane-bound, it can be released from the membrane using a suitable detergent solution (e.g., Triton-X 100) or by enzymatic cleavage. Cells employed in the expression of BCR-ABL protein can be disrupted by various physical or chemical means, such as freeze-thaw cycling, sonication, mechanical disruption, or cell lysing agents.

It may be desired to purify BCR-ABL protein from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the BCR-ABL. Various methods of protein purification may be employed and such methods are known in the art and described for example in Deutscher, Methods in Enzymology (1990), 182:83-89; Scopes, Protein Purification: Principles and Practice, Springer-Verlag, New York (1982). The purification step(s) selected will depend, for example, on the nature of the production process, source of BCR-ABL used and the particular BCR-ABL produced.

Detection of BCR-ABL Polypeptide

Several methods for detection of proteins are well known in the art. Detection of the proteins could be by resolution of the proteins by SDS polyacrylamide gel electrophoresis (SDS PAGE), followed by staining the proteins with suitable stain for example, Coomassie Blue. The BCR-ABL proteins with and without the truncation mutation can be differentiated from each other and also from other proteins based on their molecular weight and migration on SDS PAGE. BCR-ABL proteins with and without the truncation mutation can be differentiated from each other and from other proteins and also can be identified by Western blot analysis. Methods of Western blot are well known in the art and described for example in W. Burnette W. N. Anal. Biochem. 1981; 112 (2): 195-203. Briefly, BCR-ABL proteins can be subjected to SDS PAGE. Following the gel electrophoresis, the proteins can be transferred on nitrocellulose or polyvinylidene fluoride (PVDF) membrane. The membranes are blocked with suitable blocking agents to prevent non-specific binding of antibody to the membrane. Suitable blocking agents include bovine serum albumin, non-fat dry milk. After blocking and several washes with suitable buffer, antibodies that specifically bind to the BCR-ABL protein without any truncation mutation and antibodies that specifically bind to BCR-ABL protein with truncation mutation are allowed to bind to the protein of interest. Following the binding of primary antibody to the protein of interest, the excess antibodies are washed away with suitable buffer. A suitable secondary antibody that is able to bind to the primary antibody is applied. The secondary antibody is detectably labeled. Excess secondary antibody is washed away with suitable buffer and the detectable label of the secondary antibody is detected. Detection of the detectable label of the secondary antibody indicates the presence of the protein of interest. If primary antibodies specific for the truncation mutant of BCR-ABL protein is used, then the truncation mutant of BCR-ABL protein can be identified.

In preferred examples, Flow Cytometry may be applied to detect the truncation mutant of BCR-ABL protein with or without truncation mutation. Antibodies specific for the wild-type or truncation mutant of BCR-ABL protein can be coupled to beads and can be used in the Flow Cytometry analysis.

In some examples, protein microarrays may be applied to identify truncation mutant of BCR-ABL protein and can be used to differentiate from BCR-ABL protein without such mutation. Methods of protein arrays are well known in the art. In one example, antibodies specific for each protein may be immobilized on the solid surface such as glass or nylon membrane. The proteins can then be immobilized on the solid surface through the binding of the specific antibodies. Antibodies may be applied that bind specifically to a second epitope of the BCR-ABL proteins with and without truncation mutation. The first antibody/protein/second antibody complex can then be detected using a detectably labeled secondary antibody. The detectable label can be detected as discussed for nucleic acid.

Antibody Production and Screening

Various procedures known in the art may be used for the production of antibodies to epitopes of the BCR-ABL protein and the truncation mutants of BCR-ABL protein. Such antibodies include but are not limited to polyclonal, monoclonal, chimeric, single chain, Fab fragments and fragments produced by a Fab expression library. Antibodies that specifically bind to an epitope of SEQ ID NO's: 6, 10, 15, or 19 are useful for detection and diagnostic purposes.

In one examples, the antibodies may bind specifically to an epitope comprising at least 10 contiguous amino acids of SEQ ID NO: 20, 11, 16. Such antibodies are useful for detection and diagnostic purposes.

Monoclonal antibodies that bind BCR-ABL protein and the truncation mutants of BCR-ABL protein may be radioactively labeled allowing one to follow their location and distribution in the body after injection. Radioactivity tagged antibodies may be used as a non-invasive diagnostic tool for imaging de novo cells of tumors and metastases.

Immunotoxins may also be designed which target cytotoxic agents to specific sites in the body. For example, specific monoclonal antibodies with high affinity for BCR-ABL protein and truncation mutants of BCR-ABL protein may be covalently complexed to bacterial or plant toxins, such as diphtheria toxin, abrin or ricin. A general method of preparation of antibody/hybrid molecules may involve use of thiol-crosslinking reagents such as SPDP, which attack the primary amino groups on the antibody and by disulfide exchange, attach the toxin to the antibody. The hybrid antibodies may be used to specifically eliminate BCR-ABL protein and truncation mutants of BCR-ABL protein expressing cells.

For the production of antibodies, various host animals may be immunized by injection with the full length or fragment of BCR-ABL protein and the truncation mutants of BCR-ABL protein including but not limited to rabbits, mice, rats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette-Guerin) and *Corynebacterium parvum*.

Monoclonal antibodies to BCR-ABL protein and the truncation mutant of BCR-ABL protein may be prepared by using any technique which provides for the production of antibody molecules by continuous cell lines in culture. These include but are not limited to the hybridoma technique originally described by Kohler and Milstein, (Nature (1975), 256:495-497), the human B-cell hybridoma technique (Kosbor et al., Immunology Today (1983), 4:72; Cote et al. Proc. Natl. Acad. Sci. (1983), 80:2026-2030) and the EBV-hybridoma technique (Cole et al., Monoclonal Antibodies and Cancer Therapy (1985), Alan R. Liss, Inc., pp. 77-96). In addition, techniques developed for the production of "chimeric antibodies" (Morrison et al., Proc. Natl. Acad. Sci. USA (1984), 81:6851-6855; Neuberger et al., Nature (1984), 312:604-608; Takeda et al., Nature (1985), 314:452-454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce BCR-ABL protein and truncation mutant of BCR-ABL protein-specific single chain antibodies.

Antibody fragments which contain specific binding sites of BCR-ABL protein and truncation mutants of BCR-ABL protein may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., Science. 1989; 246: 1275-1281) to allow rapid and easy identification of monoclonal Fab fragments with the desired specificity to BCR-ABL protein and truncation mutant of BCR-ABL protein.

Kits

Kits for diagnostic are provided. A diagnostic system may include a kit which contains, in an amount sufficient for at least one assay, any of the hybridization assay probes, amplification primers, and/or antibodies against BCR-ABL wild type and truncation mutant in a packaging material. Typically, the kits will also include instructions recorded in a tangible form (e.g., contained on paper or an electronic medium) for using the packaged probes, primers, and/or antibodies in a detection assay for determining the presence or amount of BCR-ABL variant mRNA or BCR-ABL truncation mutant protein in a test sample.

The various components of the diagnostic systems may be provided in a variety of forms. For example, the required enzymes, the nucleotide triphosphates, the probes, primers, and/or antibodies may be provided as a lyophilized reagent. These lyophilized reagents may be pre-mixed before lyophilization so that when reconstituted they form a complete mixture with the proper ratio of each of the components ready for use in the assay. In addition, the diagnostic systems may contain a reconstitution reagent for reconstituting the lyophilized reagents of the kit. In preferred kits for amplifying target nucleic acid derived from a CIVIL patients, the enzymes, nucleotide triphosphates and required cofactors for the enzymes are provided as a single lyophilized reagent that, when reconstituted, forms a proper reagent for use in the present amplification methods.

In one example, the kit may comprise at least three lyophilized oligonucleotides: a primer pair to amplify a portion of BCR-ABL mRNA comprising exons 8 and 9, and a detectably labeled probe capable of hybridizing to the amplicon generated. In some preferred kits, at least three lyophilized oligonucleotides are the primers for amplification of at least a portion of BCR-ABL mRNA by semi-nested PCR. The primers may have sequences of SEQ ID NO: 21, SEQ ID NO: 22, SEQ ID NO: 23. or complements and fragments thereof respectively. In some preferred kits at least five lyophilized oligonucleotide reagents may be of provided having sequences of SEQ ID NOs: 21-25 or complements and fragments thereof. In some examples, SEQ ID NOs: 22-25 may be used for sequencing the PCR product.

Some preferred kits may further comprise to a solid support for anchoring the nucleic acid of interest on the solid support. The target nucleic acid may be anchored to the solid support directly or indirectly through a capture probe anchored to the solid support and capable of hybridizing to the nucleic acid of interest. Examples of such solid support include but are not limited to beads, microparticles (for example, gold and other nano particles), microarray, microwells, multiwell plates. The solid surfaces may comprise a first member of a binding pair and the capture probe or the target nucleic acid may comprise a second member of the binding pair. Binding of the binding pair members will anchor the capture probe or the target nucleic acid to the solid surface. Examples of such binding pairs include but are not limited to biotin/streptavidin, hormone/receptor, ligand/receptor, antigen/antibody.

In other preferred kits, lyophilized antibodies against BCR-ABL wild type and truncation mutant protein are provided. In some preferred kits a primary/secondary antibody pair may be provided. Some preferred kits may further comprise to a solid support for anchoring the BCR-ABL wild type and truncation mutant proteins. Such anchoring of the BCR-ABL wild type and truncation mutant proteins may be through biotin/streptavidin, antigen/antibody interactions.

Typical packaging materials would include solid matrices such as glass, plastic, paper, foil, micro-particles and the like, capable of holding within fixed limits hybridization assay probes, and/or amplification primers. Thus, for example, the packaging materials can include glass vials used to contain sub-milligram (e.g., picogram or nanogram) quantities of a contemplated probe, primer, or antibodies or they can be microtiter plate wells to which probes, primers, or antibodies have been operatively affixed, i.e., linked so as to be capable of participating in an amplification and/or detection methods.

The instructions will typically indicate the reagents and/or concentrations of reagents and at least one assay method parameter which might be, for example, the relative amounts of reagents to use per amount of sample. In addition, such specifics as maintenance, time periods, temperature, and buffer conditions may also be included.

The diagnostic systems contemplate kits having any of the hybridization assay probes, amplification primers, or antibodies described herein, whether provided individually or in one of the preferred combinations described above, for use in determining the presence or amount of BCR-ABL variant mRNA or BCR-ABL truncation mutant protein in a test sample.

Identifying a Compound for Treating CML Patients

In one preferred example, cell lines expressing BCR-ABL (both wild-type and/or mutant) proteins may be utilized to screen compounds for treating CML patients. In preferred examples, the compounds may be targeting BCR-ABL protein. In some examples, the compounds may be inhibitor of ABL kinase activity. Non-limiting examples of kinase inhibitors include but not limited to imatinib, dasatinib, nilotinib, Bosutinib (SKI-606) and Aurora kinase inhibitor VX-680. In other examples, the compounds may not be an inhibitor of ABL kinase activity.

The effect of the compounds on the cells may be assessed. Several parameters may be assessed for identifying the compounds that may be beneficial for treatment of CML patients. Non-limiting examples of the parameters that may be assessed includes cell viability, cell proliferation, apoptosis, kinase activity of BCR-ABL protein, additional mutations in BCR-ABL protein, additional mutation in ABL protein.

In one example, human chronic myeloid leukemia (CML) cell lines expressing BCR-ABL (both wild-type and/or mutant) proteins may be used to study the effect of such compounds on their effect on the cells. Non-limiting examples of human chronic myeloid leukemia (CIVIL) cell lines include BV173, K562, KCL-22, and KYO-1, LAMA84, EM2, EM3, BV173, AR230, and KU812 (Mahon, F. X., Blood. 2000; 96: 1070-1079; Lerma et al. Mol. Cancer Ther. 2007; 6(2): 655-66).

In other examples, non-CML cells may be transfected with expression vectors comprising BCR-ABL gene or variants of BCR-ABL gene including truncation variants of BCR-ABL gene resulting in genetically modified cells comprising the recombinant polynucleotide. Thus, the transfected cells will be able to express BCR-ABL protein or its variants. The genetically modified cells can be used to screen compounds for treating CML patients.

In yet other examples, CML cell lines, for example BV173, K562, KCL-22, and KYO-1, LAMA84, EM2, EM3, BV173, AR230, and KU812 may be transfected with expression vectors comprising variants of BCR-ABL gene (such as, Del 2595-2779, Del 2596-2597, 2417insCAGG, C2506T) resulting in genetically modified cells comprising the recombinant polynucleotide. The gene product of the variants of BCR-ABL gene, the truncation mutant of BCR-ABL may impart partial or total resistance to ABL kinase inhibitors to these genetically modified cells. The genetically modified cells may be used to screen compounds for treating CML. The compounds may be inhibitors of ABL kinase activity or these compounds may have other mechanism of action.

The CIVIL cell lines and the genetically modified cell lines as discussed above may be grown in appropriate growth medium and using appropriate selective antibiotics. Methods for cell culture is well known in the art (Sambrook, et al., Molecular Cloning: A Laboratory Manual (1989), Second Edition, Cold Spring Harbor Press, Plainview, N.Y.). Several growth media for cell culture are commercially available. Non-limiting examples include GIBCO® RPMI Media 1640, Dulbecco's Modified Eagle Medium (DMEM), DMEM: Nutrient Mixture F-12 (DMEM/F12), Minimum Essential Media (Invitrogen Corp., Carlsbad, Calif., USA), RF-10 medium. Non-limiting examples of selective antibiotics include ampicillin, neomycin, Geneticin®, Hygromycin B.

In one preferred example, K562 cells (ATCC catalog no: CCL-243) may be genetically modified by transfecting with different amounts of the expression vector pCMV/GFP comprising the BCR-ABL gene variants (such as, Del 2595-2779, Del 2596-2597, 2417insCAGG, C2506T). In one example, the amount the expression vector pCMV/GFP comprising the BCR-ABL gene variants used for transfection can be 0 ng, or can be at least about: 1 ng, 2 ng, 5 ng, 7.5 ng, 10 ng, 12.5 ng, 15 ng, 20 ng, 25 ng, 30 ng, 40 ng, 50 ng, 60 ng, 75 ng, 100 ng, 125 ng, 200 ng, 500 ng, 750 ng, or 1 µg. The transfected cells may be grown in RF-10 medium with neomycin/and or ampicillin.

Assessing the Effect of a Compound for Treatment of CML on Genetically Modified Cells Several parameters may be assessed for identifying the compounds that may be beneficial for treatment of CML patients. Non-limiting examples of the parameters that may be assessed includes cell viability, cell proliferation, apoptosis, kinase activity of BCR-ABL protein, additional mutations in BCR-ABL protein, additional mutation in ABL protein.

Cell Viability:

Cells can be plated at a density of 2 to $2.5 \times 10^5$ cells/mL in RF-10 with varying amounts of the compound or without the compound. Aliquots are taken out at 24-hour intervals for assessment of cell viability by tryphan blue exclusion. Alternatively, cell viability can be measured by colorimetric assay such as MTT assay (Mosman et al. J. Immunol. Meth. 1983; 65: 55-63). Commercial kits for MTT assay are available. For example, CellTiter 96® Non-Radioactive Cell Proliferation Assay (MTT) (Promega Corporation, WI, USA), Vybrant® MTT Cell Proliferation Assay Kit (Invitrogen Corp., Carlsbad, Calif., USA).

Cell Proliferation:

Proliferation of the genetically modified cells in presence of a compound for treatment of CIVIL patient can be measured in several ways. The proliferation of the cells can be indicative of the effectiveness of the compound for CML therapy.

In one such method, cell proliferation assay can performed using MTS tetrazolium such as Cell Titer96 Aqueous (Promega corporation, WI, USA), which measures numbers of viable cells. Between $2 \times 10^3$ and $2 \times 10^4$ cells are washed twice in RF-10 and plated in quadruplicate into microtiterplate wells in 100 µL RF-10 plus various doses of the compound. Controls using the same concentrations of compound without cells are set up in parallel. Twenty microliters MTS is added to the wells at daily intervals. Two hours after MTS is added, the plates are read in a microplate auto reader (Dynex Technologies, Billingshurst, UK) at 490-nm wavelength. Results are expressed as the mean optical density for each dose of the compound. All experiments are repeated at least 3 times.

In another method, cell proliferation assay can be performed by monitoring the incorporation bromo-deoxyuracil (BrdU) into newly synthesized DNA. Amount of BrdU incorporated into the DNA will be proportional to the amount of DNA synthesis and will be indicative of the proliferating cells. In one such method, detectably labeled anti-BrdU antibody can be used to measure the amount of BrdU incorporated into the cells treated with various amounts of the compound. In one example, the detectable label can be FITC. The amount of signal from FITC-labeled anti-BrdU bound to the DNA can be measured by Flow Cytometry. Commercially available kits for flow cytometry based cell proliferation assays are available. Such as, Click-iT® EdU (Invitrogen Corp., Carlsbad, Calif., USA). ELISA based assays for measuring BrdU incorporation by proliferating cells care commercially available examples include BrdU Cell Proliferation Assay kit (Calbiochem, EMD Chemicals Inc, NJ, USA).

In another method, proliferation of cells treated with various amounts of the compound can be measured by monitoring the incorporation of radioactively labeled deoxynucleotides (Sun et al. Cancer Res. 1999; 59: 940-946).

Kinase Activity of BCR-ABL:

The effect of a compound on the kinase activity of the BCR-ABL is assessed by monitoring tyrosine phosphorylation profile of the cellular proteins. CrlkL is a substrate of BCR-ABL tyrosine kinase (Ren et al. Genes Dev. 1994; 8(7): 783-95). Genetically modified cells comprising recombinant BCR-ABL or variant so of BCR-ABL including the truncation variant are grown in presence of various amounts of a compound for treating CIVIL patients. In a preferred example, the compounds are ABL tyrosine kinase inhibitors. Non-limiting examples of kinase inhibitors include imatinib, nilotinib, dasatinib, Bosutinib (SKI-606) and Aurora kinase inhibitor VX-680. Amount of phosphorylated CrkL protein can be measured by using detectably labeled anti-phospho CrkL antibody. In one example, the detectable label is phycoerythrin. The signal can be detected by Flow cytometer. Alternatively, the signal can be detected by Fluorescent Microtiter plate reader.

Sequencing of the ABL Kinase Domain:

To further investigate the reason for some cells that do not overexpress BCR-ABL but that have higher resistance to a compound that target the ATP-binding site of the ABL kinase domain (such as imatinib, nilotinib, dasatinib, and Aurora kinase inhibitor VX-680) than their sensitive counterparts, the entire kinase domain of K562-sensitive and -resistant cells can be sequenced. Sequencing can be performed using ABI prism 377 automated DNA sequencer (PE Applied Biosystems; USA). Sequence analysis can performed using the GCG version 10 software.

Example 1

Sample Collection

Patients:

Peripheral blood samples were collected from CML patients with or without imatinib resistance. Some of imatinib resistant patients were also resistant to nilotinib and dasatinib. The diagnosis of CIVIL was established based on the examination of bone marrow morphology, cytogenetic, FISH, and molecular studies. The majority of tested samples were fresh, but a significant number used cells frozen in freezing mix and stored at −70° C.

Peripheral Blood Samples:

Venous blood (5-8 ml) were collected from patients diagnosed with CML using BD Vacutainer™ CPT™ tubes (Beckton Dickenson, NJ, USA, Catalog number: 362760) by venous puncture. Peripheral mononuclear cells and platelets were isolated using manufacturer's protocol. Briefly, venous blood collected into the CPT™ tube was mixed with the anticoagulant present in the tube by inversion. The blood sample was centrifuged at 1500-1800 RCF for 20 min at room temperature (18° C.-25° C.). Plasma was removed from the top by aspiration without disturbing the white cell layer containing peripheral mononuclear cells and platelets. The peripheral mononuclear cells and platelets were carefully removed with a Pasteur pipette and collected in a separate tube.

RNA Extraction:

Total RNA was isolated from the isolated peripheral mononuclear blood cells and platelets using MagNA Pure Compact RNA Isolation Kit (Roche Applied Sciences, Indianapolis, Ind., Catalog number: 04802993001). Briefly, the prefilled cartridges provided in the kit were penetrated by the disposable piercing tool. Samples are lysed by incubation in lysis buffer containing chaotropic salt and Proteinase K. RNA was bound to the surfaces of the added Magnetic Glass Particles and DNA was degraded by incubation with DNase. After several washing steps to remove unbound substances, the purified RNA is eluted and was transferred to the Elution Tubes. RNA was dissolved in 50 μl of water and is used in subsequent RT/PCR reaction.

cDNA Synthesis:

One (1) to five (5) micrograms of RNA in 13 μl of DEPC-treated water was added to a clean microcentrifuge tube. One microliter of either oligo (dT)$_{18}$ (0.5 μg/μl) or random hexamer solution (50 ng/μl) was added and mixed gently. The mixture was heated to 70° C. for 10 min, followed by incubation on ice for one minute. The reaction mixture was centrifuged briefly, followed by the addition of 2 μl of 10× Synthesis buffer (200 mM Tris-HCl, pH 8.4, 500 mM KCl, 25 mM Magnesium chloride, 1 mg/ml of BSA), one μl of 10 mM each of dNTP mix, 2 μl of 0.1 M DTT, one μl of SuperScript II RT (200 U/μl) (Life Technologies, GIBCO BRL, Gaithersburg, Md.). After gentle mixing, the reaction mixture was subjected to brief centrifugation, and was incubated at room temperature for 10 min. The reaction mixture was further incubated at 42° C. for 50 minutes. The reaction was terminated by incubating at 70° C. for 15 min, and then placing it on ice. The reaction mixture is briefly centrifuged, and 1 μl of RNase H (2 Units) was added followed by incubation at 37° C. for 20 min.

Example 2

BCR-ABL Mutation Detection and Analysis

Amplification of the Kinase Domain of BCR-ABL Gene:

The kinase domain of the BCR-ABL gene was amplified by semi-nested polymerase chain reaction (PCR) using the cDNA derived from CML patient's mRNA as template. Semi-nested PCR was carried out with outer forward, inner forward primer and reverse PCR primers, sequences of which shown below:

```
Outer forward primer (BCR-F):
                                    (SEQ ID NO: 21)
TGACCAACTCGTGTGTGAAACTC Reverse primer (ABL-R2):
                                    (SEQ ID NO: 22)
TCCACTTCGTCTGAGATACTGGATT Inner forward primer (ABL-F1):
                                    (SEQ ID NO: 23)
CGCAACAAGCCCACTGTCT
```

Outer forward primer SEQ ID NO: 21 anneals to BCR exon b2 and the reverse primer SEQ ID NO: 22 anneals to the junction of ABL exon 9 and 10. This ensures that un-translocated ABL gene will not be amplified. The second round of PCR (semi-nested PCR) was carried out with using an inner forward primer that anneals to ABL exon 4 (SEQ ID NO: 23) and reverse primer SEQ ID NO: 22. The semi-nested PCR generated a 863 bp amplicon.

The reaction mixture included cDNA (2 μg), 8 μl of 10× synthesis buffer (200 mM Tris-HCl, pH 8.4, 500 mM KCl, 25 mM magnesium chloride, 1 mg/ml of BSA), 68 μl sterile double-distilled water, 1 μl of reverse amplification primer SEQ ID NO: 22 (10 μM), 1 μl of outer of inner forward amplification primers SEQ ID NO: 21 or 23 (10 μM) respectively, 1 μl Taq DNA polymerase (2-5 U/μl) were added. The reaction mixture is mixed gently and the reaction mixture is overlayed with mineral oil. The reaction mixture is heated to 94° C. for 5 minutes to denature remaining RNA/cDNA hybrids. PCR amplification is then performed in an automated thermal-cycler for 15-50 cycles, at 94° C. for 1 minute, 55° C. for 30 to 90 seconds, and 72° C. for 2 minutes.

Sequencing of PCR Products:

The 863 bp PCR product was extracted from gel, purified was sequenced using the ABI Prism BigDye® Terminator v3.1 Cycle Sequencing Kit and detected by ABI PRISM® 3730 Genetic Analyzer (Applied Biosystems, Foster City, Calif., USA). Sequencing of the PCR product was performed using 2 sets of forward and reverse primer pairs. Sequences of the primers are shown below:

```
(ABL-F1):
                                    (SEQ ID NO: 23)
CGCAACAAGCCCACTGTCT (ABL-R2):
                                    (SEQ ID NO: 22)
TCCACTTCGTCTGAGATACTGGATT
```

Figure 2:
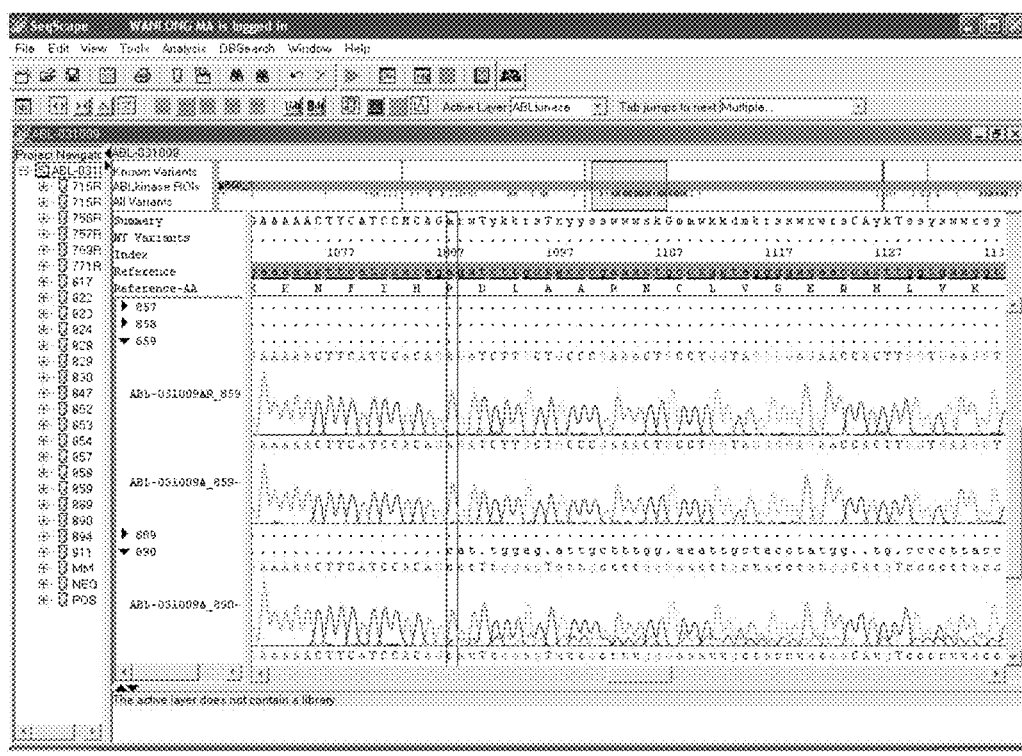
FIGS. 2A-2D show the chromatograms of sequencing BCR-ABL cDNA variants.
FIG. 2E shows an exemplary sequence analysis of Del 2595-2779 sequence by ABI Prism® SeqScape software.
Figure 2:
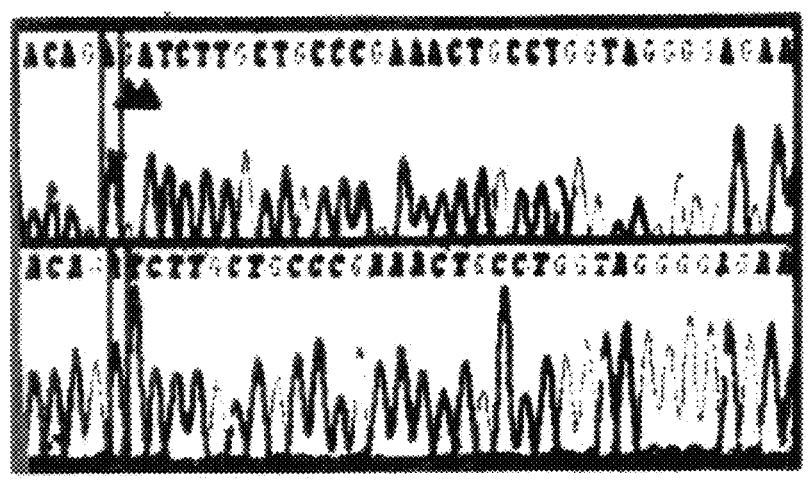

-continued (ABL-R1):
(SEQ ID NO: 24)
CAAGTGGTTCTCCCCTACCA (ABL-F2):
(SEQ ID NO: 25)
TGGTAGGGGAGAACCACTTG Sequence data was then analyzed by ABI Prism® SeqScape software (Applied Biosystems, Foster City, Calif., USA) using the ABL sequence (accession number M14752) as a reference. Sequencing indicated four unique mutations in the BCR-ABL gene: a large deletion of nucleotides 2595-2779, a dinucleotide deletion of GA at position 2596-2597, a tetranucleotide insertion of CAGG immediately after nucleotide position 2417, or a substitution of C to T at position 2506 of SEQ ID NO: 1. Chromatogram of the sequencing results are shown in FIGS. 2 A-D. Exemplary results of the analysis of the nucleotide sequences of Del 2595-2779 mutation by ABI Prism® SeqScape software is shown in FIG. 2 E.

The instant application contains a Sequence Listing which is submitted along with this application via EFS-Web and is hereby incorporated by reference in its entirety. The ASCII copy, created on Nov. 4, 2009, is named 03482707.txt.

Unless otherwise defined, all technical and scientific terms used herein have the same meaning as commonly understood by one of ordinary skill in the art to which this invention belongs. All nucleotide sequences provided herein are presented in the 5' to 3' direction.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred examples and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred examples, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other examples are set forth within the following claims.

What is claimed is:

1. A method for determining the prognosis of a patient diagnosed as having a myeloproliferative disease comprising:

(a) assaying a nucleic acid sample comprising a BCR-ABL nucleic acid obtained from the patient to determine the presence of one or more BCR-ABL truncation mutations selected from the group consisting of 2417insCAGG, Del 2596-2597, and C2506T, wherein assaying comprises:

(i) performing a nucleic acid amplification reaction on the BCR-ABL nucleic acid sample with at least one primer pair comprising a forward primer that binds to ABL exon 4 and a reverse primer that binds to the junction of ABL exon 9 and exon 10;

(ii) contacting the amplified BCR-ABL nucleic acid with a detectably labeled nucleic acid probe that specifically hybridizes to a mutant BCR-ABL nucleic acid comprising the mutation, if present, but not to a wild-type BCR-ABL nucleic acid comprising SEQ ID NO: 1, wherein:

(1) the detectably labeled nucleic acid probe for detecting the 2417insCAGG mutation comprises at least 20 contiguous nucleotides of SEQ ID NO: 13;

(2) the detectably labeled nucleic acid probe for detecting the Del 2596-2597 mutation comprises at least 20 contiguous nucleotides of SEQ ID NO: 8; and (3) the detectably labeled nucleic acid probe for detecting the C2506T mutation comprises at least 20 contiguous nucleotides of SEQ ID NO: 18; and (iii) detecting the BCR-ABL truncation mutation when a hybrid is formed between the detectably labeled nucleic acid probe and the BCR-ABL nucleic acid; and (b) identifying said patient as having poor prognosis when said one or more mutations are present.

2. The method of claim 1, wherein said myeloproliferative disease is CML.

3. The method of claim 1, wherein said myeloproliferative disease is ALL.

4. A method for predicting the likelihood for resistance to treatment with a tyrosine kinase inhibitor in a patient diagnosed as having a myeloproliferative disease, comprising:
(a) assaying a nucleic acid sample comprising a BCR-ABL nucleic acid obtained from the patient to determine the presence of one or more BCR-ABL truncation mutations selected from the group consisting of 2417insCAGG, Del 2596-2597, and C2506T, wherein assaying comprises:
(i) performing a nucleic acid amplification reaction on the BCR-ABL nucleic acid sample with at least one primer pair comprising a forward primer that binds to ABL exon 4 and a reverse primer that binds to the junction of ABL exon 9 and exon 10;
(ii) contacting the amplified BCR-ABL nucleic acid with a detectably labeled nucleic acid probe that specifically hybridizes to a mutant BCR-ABL nucleic acid comprising the mutation, if present, but not to a wild-type BCR-ABL nucleic acid comprising SEQ ID NO: 1, wherein:
(1) the detectably labeled nucleic acid probe for detecting the 2417insCAGG mutation comprises at least 20 contiguous nucleotides of SEQ ID NO: 13;
(2) the detectably labeled nucleic acid probe for detecting the Del 2596-2597 mutation comprises at least 20 contiguous nucleotides of SEQ ID NO: 8; and
(3) the detectably labeled nucleic acid probe for detecting the C2506T mutation comprises at least 20 contiguous nucleotides of SEQ ID NO: 18; and
(iii) detecting the BCR-ABL truncation mutation when a hybrid is formed between the detectably labeled nucleic acid probe and the BCR-ABL nucleic acid; and
(b) identifying said patient as having a likelihood of resistance to a tyrosine kinase inhibitor when one or more said mutations are present.

5. The method of claim 4, wherein said tyrosine kinase inhibitor is one or more selected from the group consisting of imatinib, nilotinib and dasatinib.

6. The method of claim 4, wherein said tyrosine kinase inhibitor is imatinib.

7. The method of claim 4, wherein said myeloproliferative disease is CML.

8. The method of claim 4, wherein said myeloproliferative disease is ALL.

9. The method of claim 4, wherein said patient is being administered a tyrosine kinase inhibitor.

10. The method of claim 9, wherein said tyrosine kinase inhibitor is one or more selected from the group consisting of imatinib, nilotinib and dasatinib.

11. The method of claim 10, wherein the treatment regimen of the patient is modified when at least one of said mutations is identified.

12. The method of claim 1, wherein the treatment regimen of the patient is modified when at least one of said mutations is identified.

13. The method of claim 1, wherein nucleic acid amplification comprises real-time polymerase chain reaction (RT-PCR).

14. The method of claim 4, wherein nucleic acid amplification comprises real-time polymerase chain reaction (RT-PCR).

15. A method for detecting one or more BCR-ABL truncation mutations selected from the group consisting of 2417insCAGG, Del 2596-2597, and C2506T, comprising:
(a) contacting a nucleic acid sample comprising a BCR-ABL nucleic acid from a human patient or a BCR-ABL nucleic acid isolated therefrom with a detectably labeled nucleic acid probe that specifically hybridizes to a mutant BCR-ABL nucleic acid comprising the mutation, if present, but not to a wild-type BCR-ABL nucleic acid comprising SEQ ID NO: 1, wherein:
(i) performing a nucleic acid amplification reaction on the BCR-ABL nucleic acid sample with at least one primer pair comprising a forward primer that binds to ABL exon 4 and a reverse primer that binds to the junction of ABL exon 9 and exon 10;
(ii) the detectably labeled nucleic acid probe for detecting the 2417insCAGG mutation comprises at least 20 contiguous nucleotides of SEQ ID NO: 13;
(iii) the detectably labeled nucleic acid probe for detecting the Del 2596-2597 mutation comprises at least 20 contiguous nucleotides of SEQ ID NO: 8; and
(iv) the detectably labeled nucleic acid probe for detecting the C2506T mutation comprises at least 20 contiguous nucleotides of SEQ ID NO: 18; and
(b) detecting the BCR-ABL truncation mutation when a hybrid is formed between the detectably labeled nucleic acid probe and the BCR-ABL nucleic acid.

16. The method of claim 15, wherein nucleic acid amplification comprises real-time polymerase chain reaction (RT-PCR).

17. The method of claim 15, wherein the nucleic acid sample is obtained from a patient diagnosed as having a myeloproliferative disease.

18. The method of claim 17, wherein said myeloproliferative disease is CIVIL or ALL.

19. The method of claim 17, wherein said patient is being administered a tyrosine kinase inhibitor.

20. The method of claim 19, wherein said tyrosine kinase inhibitor is one or more imatinib, nilotinib and dasatinib.

21. The method of claim 1, wherein the forward primer comprises SEQ ID NO: 23.

22. The method of claim 1, wherein the reverse primer comprises SEQ ID NO: 22.

23. The method of claim 4, wherein the forward primer comprises SEQ ID NO: 23.

24. The method of claim 4, wherein the reverse primer comprises SEQ ID NO: 22.

25. The method of claim 15, wherein the forward primer comprises SEQ ID NO: 23.

26. The method of claim 15, wherein the reverse primer comprises SEQ ID NO: 22.

* * * * *